US008812093B2

(12) United States Patent
Gutfinger et al.

(10) Patent No.: US 8,812,093 B2
(45) Date of Patent: Aug. 19, 2014

(54) SYSTEMS AND METHODS FOR EXPLOITING NEAR-FIELD IMPEDANCE AND ADMITTANCE FOR USE WITH IMPLANTABLE MEDICAL DEVICES

(75) Inventors: Dan E. Gutfinger, Agoura Hills, CA (US); Fujian Qu, Sunnyvale, CA (US); Alex Soriano, Ventura, CA (US); Ryan Rooke, Redondo Beach, CA (US); Yelena Nabutovsky, Sunnyvale, CA (US); Riddhi Shah, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 840 days.

(21) Appl. No.: 13/007,424

(22) Filed: Jan. 14, 2011

(65) Prior Publication Data
US 2012/0035495 A1     Feb. 9, 2012

Related U.S. Application Data

(63) Continuation-in-part of application No. 12/853,130, filed on Aug. 9, 2010, now Pat. No. 8,670,820.

(51) Int. Cl.
*A61B 5/053*    (2006.01)
*A61B 5/04*     (2006.01)
*A61B 5/0452*   (2006.01)
*A61N 1/365*    (2006.01)

(52) U.S. Cl.
CPC ............. *A61B 5/04011* (2013.01); *A61B 5/053* (2013.01); *A61B 5/0452* (2013.01); *A61N 1/36521* (2013.01)
USPC ........... 600/513; 600/508; 600/509; 600/512; 607/24; 607/28

(58) Field of Classification Search
CPC .. A61B 5/04011; A61B 5/053; A61B 5/0452; A61N 1/36521
USPC ............... 600/508, 509, 512, 513; 607/24, 28
See application file for complete search history.

(56) References Cited

U.S. PATENT DOCUMENTS

| 4,674,518 | A  | 6/1987  | Salo            |
|-----------|----|---------|-----------------|
| 6,249,705 | B1 | 6/2001  | Snell           |
| 6,328,699 | B1 | 12/2001 | Eigler et al.   |
| 6,438,408 | B1 | 8/2002  | Mulligan et al. |

(Continued)

OTHER PUBLICATIONS

Bini, G.C. et. al. "A Method to Calculate Tissue Impedance through a Standard Bipolar Pacing Lead," Cardiovasc Eng. 2006;6:45-52.

(Continued)

*Primary Examiner* — Carl H Layno
*Assistant Examiner* — Eugene Wu

(57) ABSTRACT

Various techniques are provided for use with an implantable medical device for exploiting near-field impedance/admittance. Examples include techniques for assessing heart chamber disequilibrium, detecting chamber volumes and pressures, calibrating near-field-based left atrial pressure (LAP) estimation procedures and for assessing the recovery from injury at the electrode-tissue interface. In one particular example, the implantable device assesses the degree of concordance between the left ventricle (LV) and the right ventricle (RV) by quantifying a degree of scatter between LV and RV near-field admittance values. An increase in RV admittance is indicative of RV failure, an increase in LV admittance is indicative of LV failure, and an increase in both LV and RV admittance is indicative of biventricular failure.

28 Claims, 42 Drawing Sheets

(56) References Cited

U.S. PATENT DOCUMENTS

| | | | |
|---|---|---|---|
| 6,480,733 | B1 | 11/2002 | Turcott |
| 6,512,949 | B1 | 1/2003 | Combs et al. |
| 6,512,952 | B2 | 1/2003 | Stahmann et al. |
| 6,572,557 | B2 | 6/2003 | Tchou et al. |
| 6,628,988 | B2 | 9/2003 | Kramer et al. |
| 6,643,546 | B2 | 11/2003 | Mathis et al. |
| 6,643,548 | B1 | 11/2003 | Mai et al. |
| 6,645,153 | B2 | 11/2003 | Kroll et al. |
| 6,741,885 | B1 | 5/2004 | Park et al. |
| 6,748,261 | B1 | 6/2004 | Kroll et al. |
| 6,829,503 | B2 | 12/2004 | Alt |
| 6,970,742 | B2 | 11/2005 | Mann et al. |
| 7,115,095 | B2 | 10/2006 | Eigler et al. |
| 7,139,609 | B1 | 11/2006 | Min et al. |
| 7,272,443 | B2 | 9/2007 | Min et al. |
| 7,437,192 | B2 | 10/2008 | Gill et al. |
| 7,483,743 | B2 | 1/2009 | Mann et al. |
| 7,502,644 | B2 | 3/2009 | Gill et al. |
| 7,505,814 | B2 | 3/2009 | Bornzin et al. |
| 7,794,404 | B1* | 9/2010 | Gutfinger et al. ............. 600/486 |
| 8,135,468 | B2* | 3/2012 | Gutfinger et al. ............... 607/28 |
| 2008/0262361 | A1* | 10/2008 | Gutfinger et al. ............. 600/486 |
| 2009/0018597 | A1 | 1/2009 | Wenzel et al. |
| 2010/0023069 | A1* | 1/2010 | Moffitt et al. ...................... 607/2 |
| 2011/0009927 | A1* | 1/2011 | Parker et al. ...................... 607/62 |
| 2012/0035493 | A1* | 2/2012 | Gutfinger et al. ............. 600/547 |
| 2012/0035495 | A1* | 2/2012 | Gutfinger et al. ............. 600/547 |
| 2012/0165692 | A1* | 6/2012 | Hollmark et al. ............. 600/518 |

OTHER PUBLICATIONS

Braunwald, Eugene MD, "Mitral Regurgitation: Physiological, Clinical and Surgical Considerations," from Seminars in Medicine of the Beth Israel Hospital, Boston, reprinted from N Engl J Med. Aug. 21, 1969; 281:425-433.

Burch, G.E. MD et al, "The syndrome of papillary muscle dysfunction," Am Heart J. 1968;75:399-415.

Cheng, Tsung O. MD, "Some New Observations on the Syndrome of Papillary Muscle Dysfunction," Am J Med. 1969;47:924-945.

De Busk, robert F. MD et al., "The clinical spectrum of papillary muscle disease," in Medical Progress reprinted from N Engl J Med. 1969;281:1458-1467.

Khoury, Dirar S. PhD et al., "Ambulatory Monitoring of Congestive Heart Failure by Multiple Bioelectric Impedance Vectors," J Am Coll Cardiol, 2009; 53(12):1075-1081.

Levine, Robert A. MD et al., "Ischemic Mitral Regurgitation on the Threshold of a Solution From Paradoxes to Unifying Concepts," Circulation. 2005;112:745-758.

Ritzema, Jay MRCP et al. "Physician-Directed Patient Self-Management of Left Atrial Pressure in Advanced Chronic Heart Failure," Circulation. 2010;121:1086-1095.

Schlant, Robert C. MD, "The Management of Chronic Mitral Regurgitation," Council on Clinical Cardiology Newletter, editted by Beller. 1986;12(1)::1-9.

* cited by examiner

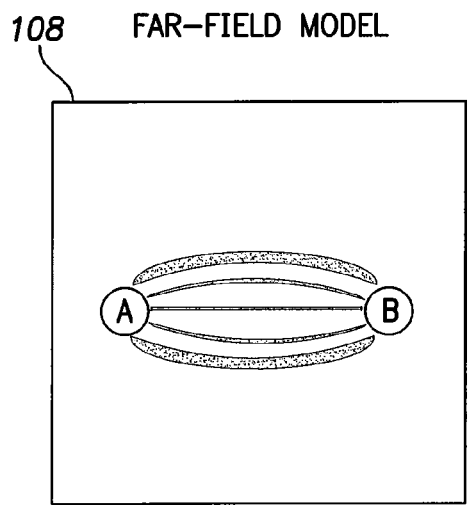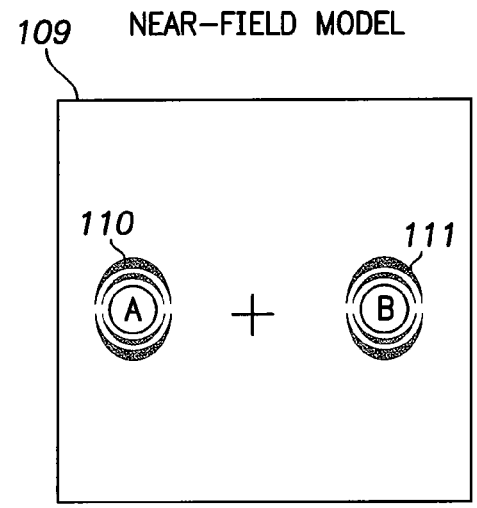
FIG. 3A
PRIOR ART
FIG. 3B

IMPEDANCE TRIANGLE
THREE ELECTRODE EXAMPLE
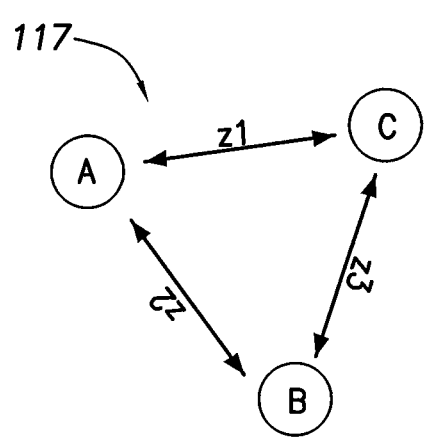
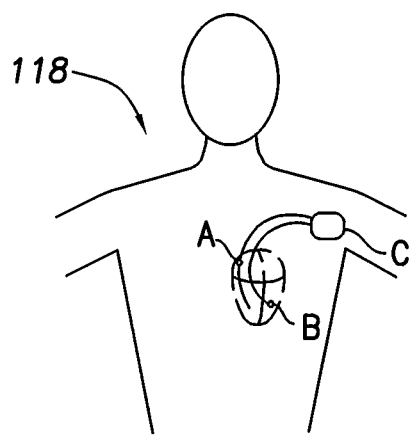
z1 = A + C
z2 = A + B
z3 = B + C
z1 + z2 − z3 = 2A
z2 + z3 − z1 = 2B
z1 + z3 − z2 = 3C
FIG. 5

ANALYTIC SOLUTION

```
v1 = LVr+Case
v2 = RVr+Case
v3 = RAr+Case
v4 = RVc+Case
v5 = LVr+RAr
v6 = LVr+RVr
```
— 216

```
e1 = [(v1−v2) + v6 + (v1−v3) + v5]/4 =
     [(LVr−RVr) + (LVr+RVr) + (LVr−RAr) + (LVr+RAr)]/4 = LVr
e2 = [(v2−v1) + v6]/2 = [(RVr−LVr) + (LVr+RVr)]/2 = RVr
e3 = [(v3−v1) + v5]/2 = [(RAr−LVr) + (LVr+RAr)]/2 = RAr
e4 = [(v1−e1) + (v2−e2) + (v3−e3)]/3 = Case
e5 = v4 − e4 = RVc
```
— 218

SOLUTION IN MATRIX FORM

— 219

$$\begin{pmatrix} LVr \\ RVr \\ RAr \\ Case \\ RVc \end{pmatrix} = \begin{bmatrix} 0.5 & -0.25 & -0.25 & 0 & 0.25 & 0.25 \\ -0.5 & 0.5 & 0 & 0 & 0 & 0.5 \\ -0.5 & 0 & 0.5 & 0 & 0.5 & 0 \\ 0.5 & 0.25 & 0.25 & 0 & -0.25 & -0.25 \\ -0.5 & -0.25 & -0.25 & 1 & 0.25 & 0.25 \end{bmatrix} \times \begin{pmatrix} V1 \\ V2 \\ V3 \\ V4 \\ V5 \\ V6 \end{pmatrix}$$

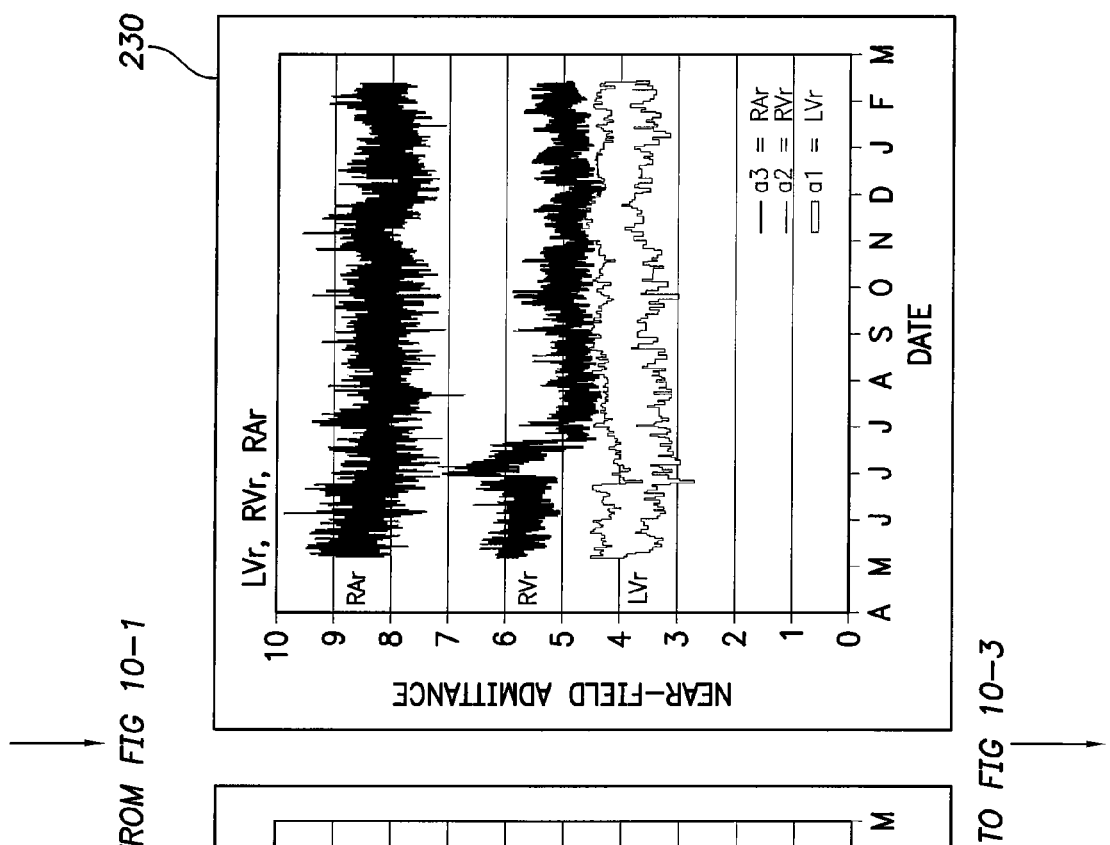
FIG. 10-2
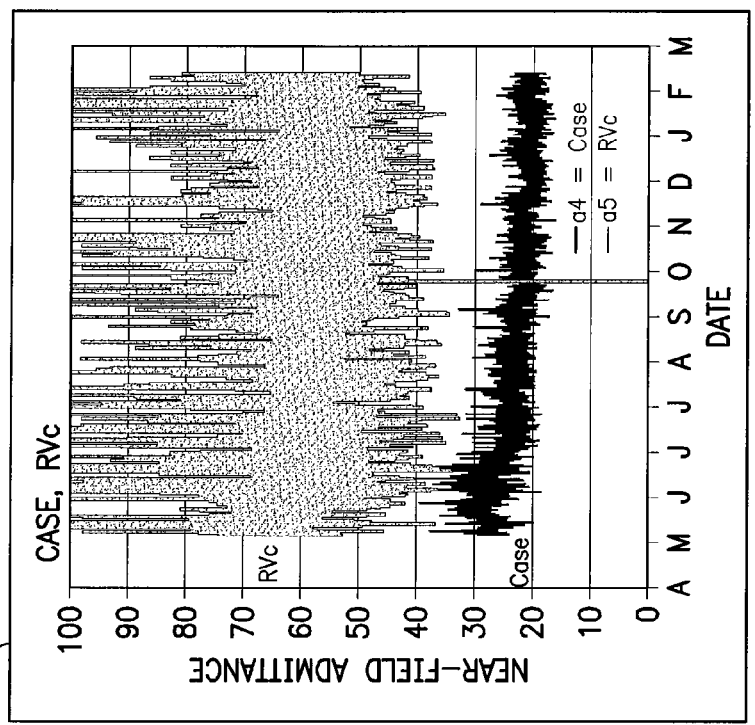

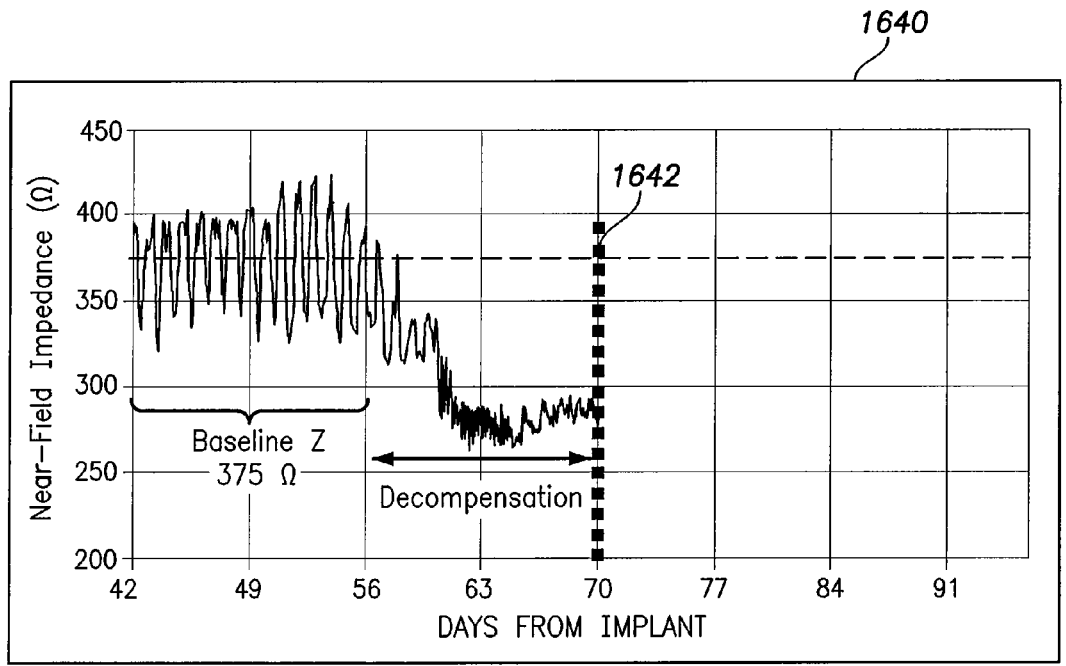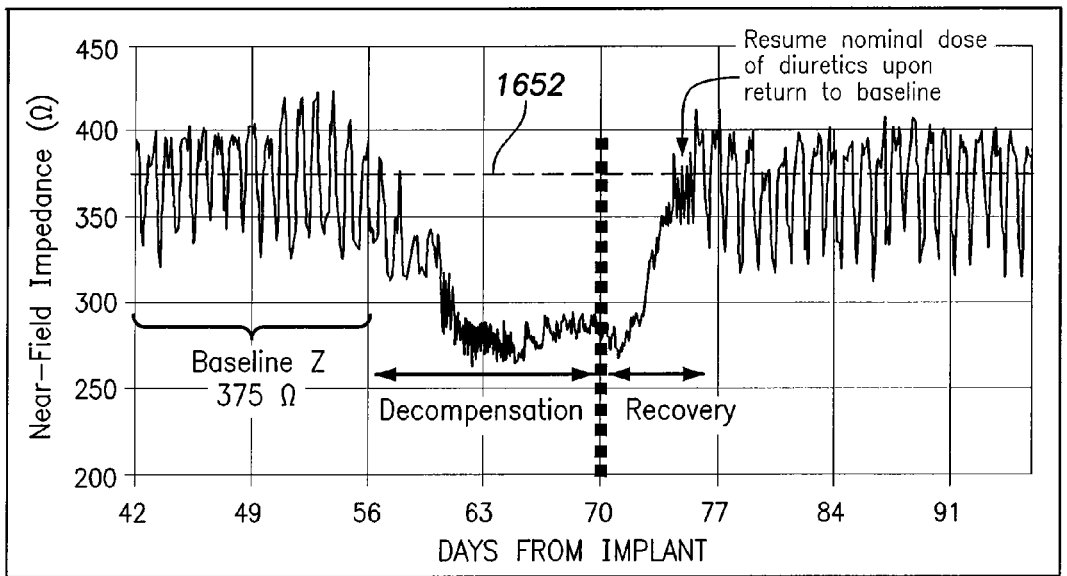
FIG. 39

SYSTEMS AND METHODS FOR EXPLOITING NEAR-FIELD IMPEDANCE AND ADMITTANCE FOR USE WITH IMPLANTABLE MEDICAL DEVICES

RELATED APPLICATIONS

This application is a Continuation-in-Part of U.S. patent application Ser. No. 12/853,130 now U.S. Pat. No. 8,670,820, filed Aug. 9, 2010, entitled "Near Field-Based Systems and Methods for Assessing Impedance and Admittance for Use with an Implantable Medical Device" and claims priority therefrom. This application is also related to 1) U.S. patent application Ser. No. 12/853,157, also filed Aug. 9, 2010, entitled "Systems and Methods for Estimating Left Atrial Pressure (LAP) in Patients with Acute Mitral Valve Regurgitation for Use by an Implantable Medical Device"; and 2) U.S. patent application Ser. No. 13/007,364, filed Jun. 14, 2011, entitled "Systems and Method for Corroborating Impedance-Based Left Atrial Pressure (LAP) Estimates for Use by an Implantable Medical Device". All applications are fully incorporated by reference herein.

FIELD OF THE INVENTION

The invention relates to implantable medical devices such as pacemakers, implantable cardioverter defibrillators (ICDs) and cardiac resynchronization therapy (CRT) devices and in particular to techniques for exploiting impedance and/or admittance parameters measured by such devices.

BACKGROUND OF THE INVENTION

State-of-the-art implantable medical devices are often equipped to measure impedance (or related electrical parameters such as admittance) between various pairs of electrodes implanted within the patient. Examples include intracardiac impedance measurements made between pairs of electrodes mounted to leads implanted on or within the various chambers of the heart. Other examples include intrathoracic impedance measurements made between the housing of the device (or "can" electrode) and electrodes implanted on or within the heart. Traditionally, such impedance measurements were deemed to be representative of the electrical impedance along a vector between the electrodes. That is, impedance measurements were associated with a particular pair of electrodes or some combination of three or more electrodes. Herein, these measurements are generally referred to as "vector-based" impedance measurements because the measurements are associated with at least one pair of electrodes and the vectors therebetween. In terms of analyzing and interpreting the measured impedance data, the interpretation typically relied on a conceptual model wherein the measured impedance was deemed to be representative of the impedance of the field between the electrodes pairs, including far-field contributions to that impedance. This traditional model is referred to herein as the "far-field model" of impedance. Under the far-field model, impedance measured along a vector between a pair of electrodes A and B is deemed to be representative of the field between A and B.

As one example of the far-field model, intrathoracic impedance measurements made between the device housing and a cardiac electrode implanted within the heart are deemed to represent the impedance to electrical flow spanning a field extending through the lungs between the device and the cardiac electrode. This intrathoracic vector-based impedance measurement is then used, for example, to assess pulmonary fluid congestion to detect pulmonary edema (PE) or heart failure (HF). Although this traditional interpretation of the impedance measurements can be useful, the present inventors have recognized that an alternative interpretation of impedance measurements based on a "near-field model" can provide a more useful means for understanding, analyzing and interpreting impedance measurements.

Briefly, with the near-field model, impedance parameters (or related electrical parameters such as admittance or immittance) are measured by an implantable medical device along vectors extending through tissues of the patient between various pairs of electrodes. The device then converts the vector-based impedance measurements into near-field individual electrode-based impedance values. This is accomplished, in at least some examples, by converting the vector-based impedance measurements into a set of linear equations to be solved while ignoring far-field contributions to the impedance measurements. The device solves the linear equations to determine the near-field impedance values for the individual electrodes, which are representative of the impedance of tissues in the vicinity of the electrodes. The device then performs or controls a variety of device functions based on the near-field values, such as analyzing trends in near-field values to detect HF or PE.

The present invention is directed to providing various additional systems and methods that exploit near-field measurements to, for example, assess heart chamber disequilibrium, electrode-tissue interface issues, etc. Various techniques are also set forth for calibrating near-field-based techniques.

SUMMARY OF THE INVENTION

In accordance with an exemplary embodiment of the invention, a method is provided for use with an implantable medical device—such as a pacemaker, ICD or CRT device—for exploiting near-field immittance values (wherein "immittance" broadly refers to impedance, admittance or other generally equivalent electrical values or parameters) associated with individual electrodes in accordance with the near-field model that associates immittance values with individual electrodes rather than with pairs of electrodes or with the vectors therebetween. In one example, the device detects vector-based immittance measurements within tissues of the patient using a plurality of electrodes coupled to the device. The device converts the vector-based immittance measurements into relative near-field individual electrode-based immittance values. The device then estimates cardiac parameters and/or device operational parameters based on the individual electrode-based immittance values. Various device functions can then be controlled based on the cardiac parameters and/or device operational parameters, such as the delivery of therapy, the generation of warning signals or the storage of diagnostic data. It should be understood that any function that the device can perform or control, alone or in combination with other devices, is a "device function." This includes, but is not limited to, detecting medical conditions such a PE or HF, assessing tissue injury, controlling CRT, generating and transmitting diagnostic information to an external system, etc.

Briefly, the near-field model is based on the recognition that the impedance along a vector between a pair of electrodes (A and B) can be modeled as a superposition of the near-field impedance values that are associated with the individual electrodes (i.e. A+B). That is:

Traditional Model: Impedance=A to B=Field between A and B

New Model Impedance=A+B=Near-Field A+Near-Field B

More generally, the near-field model transforms multiple vector-based or pair-based immittance measurements into a set of individual electrode-based near-field immittance values representative of the immittance of tissues and fluid in sufficiently close proximity to the electrode to exclude substantially all far-field immittance contributions. The near-field impedance associated with the electrode "A" reflects the impedance associated with the electrode-tissue interface, which may be modeled as the summation of the impedance associated with the bare electrode in combination with the impedance associated with the various tissues and fluid surrounding the electrode. The greatest contribution to the measured near-field immittance is from the tissues and fluid that are in direct contact with the electrode. The contribution of tissues and fluid to the near-field immittance decreases with the square of the distance from the electrode. For a typical ring-electrode the contribution beyond a distance of approximately 1 to 2 centimeters may be ignored for all practical purposes. For larger size electrodes such as the RV defibrillation coil (herein RVcoil or RVc or Coil) or the device case (herein Case) the distance for which surrounding tissues and fluid may significantly impact the measured near-field immittance is larger (~2 to 5 centimeters). Substantially any process that causes the surrounding tissues, fluid and/or electrode characteristics to change will produce a change in the measured near-field immittance. A wide variety of techniques are provided herein for exploiting near-field parameters acquired based on this model.

In one implementation example, the device detects cardiac parameters representative of disequilibrium among the chambers of the heart from the near-field immittance values. This may be achieved, for example, by deriving relative near-field admittance values from the individual electrode-based immittance values corresponding to chambers of the heart, assessing a degree of concordance between the relative near-field admittance measurements, and then identifying a poor degree of concordance as being indicative of disequilibrium between the heart chambers. In one particular embodiment, the device assesses the degree of concordance between the left ventricle (LV) and the right ventricle (RV) by quantifying a degree of scatter between the LVring and RVring near-field admittance measurements. A significant increase in the RVring near-field admittance is indicative of RV failure, a significant increase in the LVring near-field admittance is indicative of LV failure, and a significant increase in both the LVring and the RVring near-field admittances is indicative of biventricular failure.

In another implementation example, the device estimates chamber pressure or volume, such as LV end diastolic volume (LV EDV), LV end systolic volume (LV ESV) and left atrial pressure (LAP) from the near-field immittance values acquired at a high sampling rate (128 Hz). LV EDV may be estimated, for example, by converting near-field impedance values corresponding to the LV ring electrode (herein LVring or LVr) into corresponding near-field admittance values, tracking the near-field admittance values over at least one cardiac cycle to identify a peak admittance (Ymax), and associating the peak admittance as corresponding to LV EDV. LV ESV may be estimated, for example, by associating the minimum near-field admittance (Ymin) within the cardiac cycle with LV ESV. LAP may be estimated based on the LV EDV obtained from the near-field impedance values by, for example, exploiting an exponential conversion formula expressed as $a*e^{kx}$ where a and k are constants and wherein "x" represents LV EDV.

In yet another implementation example, rather than estimate LAP from LV EDV, LAP is directly estimated from the near-field impedance and/or admittance values by, for example, applying conversion coefficients directly to near-field immittance values to obtain LAP estimates. The conversion procedure may be calibrated in advance by simultaneously acquiring pulmonary capillary wedge pressure (PCWP) measurements in combination with multiple vector-based impedance measurements that are used to derive near-field impedance measurements under various physiological conditions, such as different postures and levels of fluid volume. In one particular example, in-clinic recordings of near-field immittance measurements for the RV ring electrode (herein RVring or RVr) in combination with PCWP measurements are used to derive conversion coefficients for obtaining LAP estimates from the RVr near-field impedance. The concordance between the near-field impedance of the RVr and LVr electrodes is then utilized to derive corresponding conversion coefficients that may be used to convert the near-field LVr impedance into LAP estimates. The benefit of this approach is that conversion coefficients for the RVr electrode may sometimes be easier to derive in an in-clinic setting in comparison to conversion coefficients for the LVr electrode because changes in the RVr near-field impedance may occur faster and with minimal lag in comparison to changes in the LVr near-field impedance following a change in physiologic state. This is because the RVr electrode is located within the intra-vascular space permitting instantaneous detection of changes in RV volume, whereas the LVr electrode is located outside the heart on the epicardial surface of the LV where changes in the LV volume may potentially be detected with some lag.

In still another implementation example, the device operates to assess trends in the near-field immittance measurements with the objective of assessing the recovery from tissue injury at the electrode-tissue interface. In one embodiment, the near-field impedance associated with the electrode-tissue interface is utilized to track the recovery of the tissue injury at the implant site and to detect physical disturbances at the electrode-tissue interface, such as a lead dislodgement, perforation, and/or infection.

In yet another example, the device operates to assess the recovery of the heart following a HF exacerbation episode. The near-field impedance associated with the RVr electrode is utilized to track the recovery of RV volume, which parallels closely the recovery in filling pressures, whereas the impedance associated with the LVr electrode is utilized to track the recovery of the LV myocardium, which may lag relative to the recovery in filling pressures. The recovery pattern is utilized to guide the intensity and extent of therapy along with the required follow-up duration.

A wide variety of other applications and methods may be performed in accordance with the general invention. These are just some examples.

BRIEF DESCRIPTION OF THE DRAWINGS

Further features and advantages of the invention may be more readily understood by reference to the following description taken in conjunction with the accompanying drawings, in which:

FIG. 5 is a graphical illustration of an impedance triangle corresponding to a simplified three electrode example of the near-field impedance technique exploited by the method of FIG. 2;

FIG. 8 is a diagram illustrating aspects of the procedure of FIG. 7, and particularly illustrating the calculation of near-field impedance values for a six vector and a five electrode example, both in analytic and matrix form;

FIG. 39 illustrates graphs of the near-field impedance for an electrode-tissue interface during HF decompensation and recovery exploited by the method of FIG. 36;

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System

Figure 1:
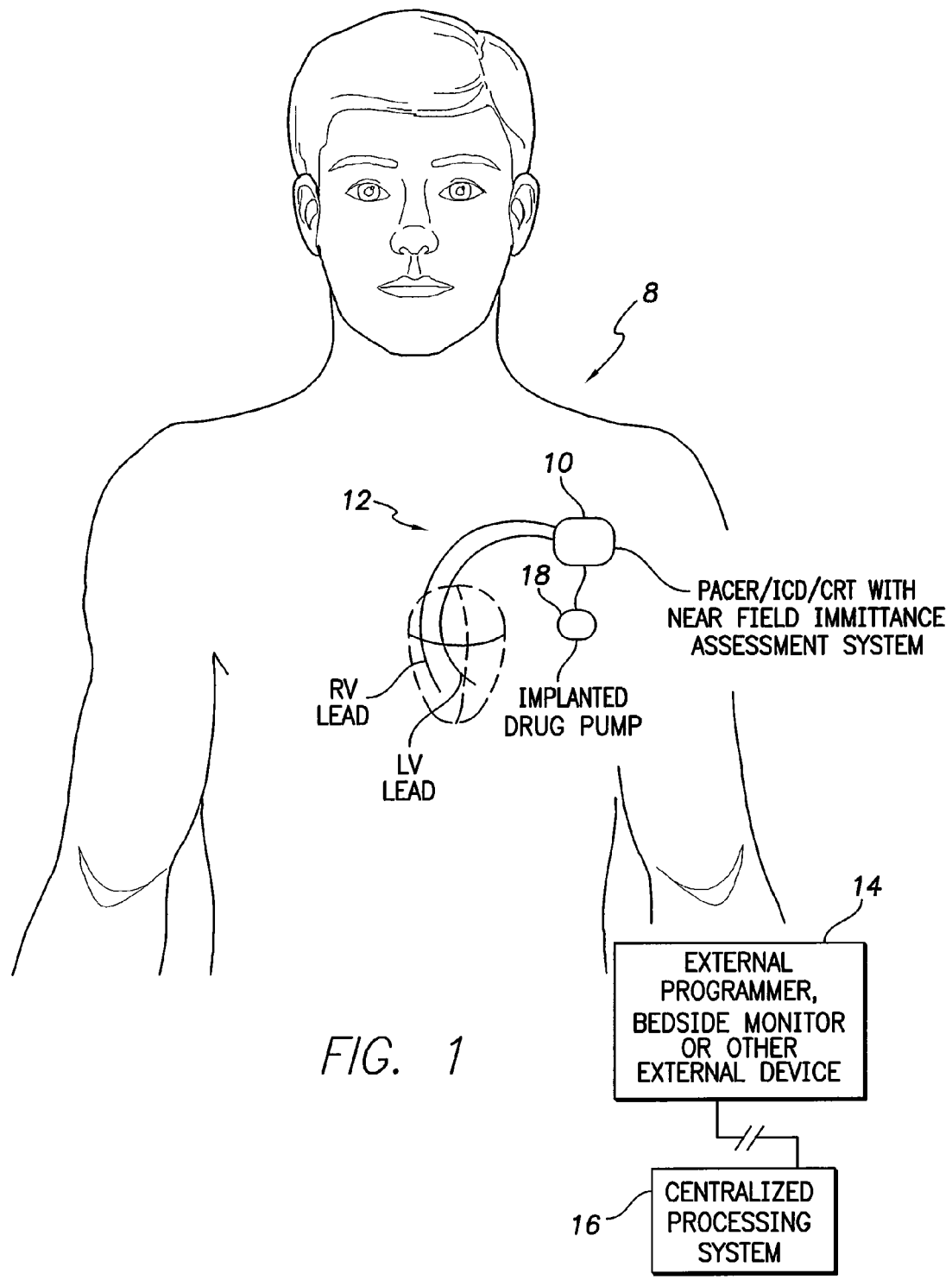
FIG. 1 is a stylized representation of an exemplary implantable medical system equipped with a system for assessing and exploiting near-field immittance values (i.e. impedance and/or admittance values)

FIG. 1 provides a stylized representation of an exemplary implantable pacing medical system 8 capable of assessing the near-field immittance of individual electrodes, i.e. the impedance, admittance or equivalent electrical parameters (such as conductance) associated with a near-field zone surrounding a given electrode. The system is further capable of estimating various cardiac parameters, such as heart chamber volumes or pressure parameters, based on the near-field immittance values. The pacer/ICD may also be equipped to detect and track HF and/or PE based on the near-field impedance or admittance values. That is, the device is equipped to exploit the aforementioned near-field model to perform various useful detection or estimation functions.

Figure 20:
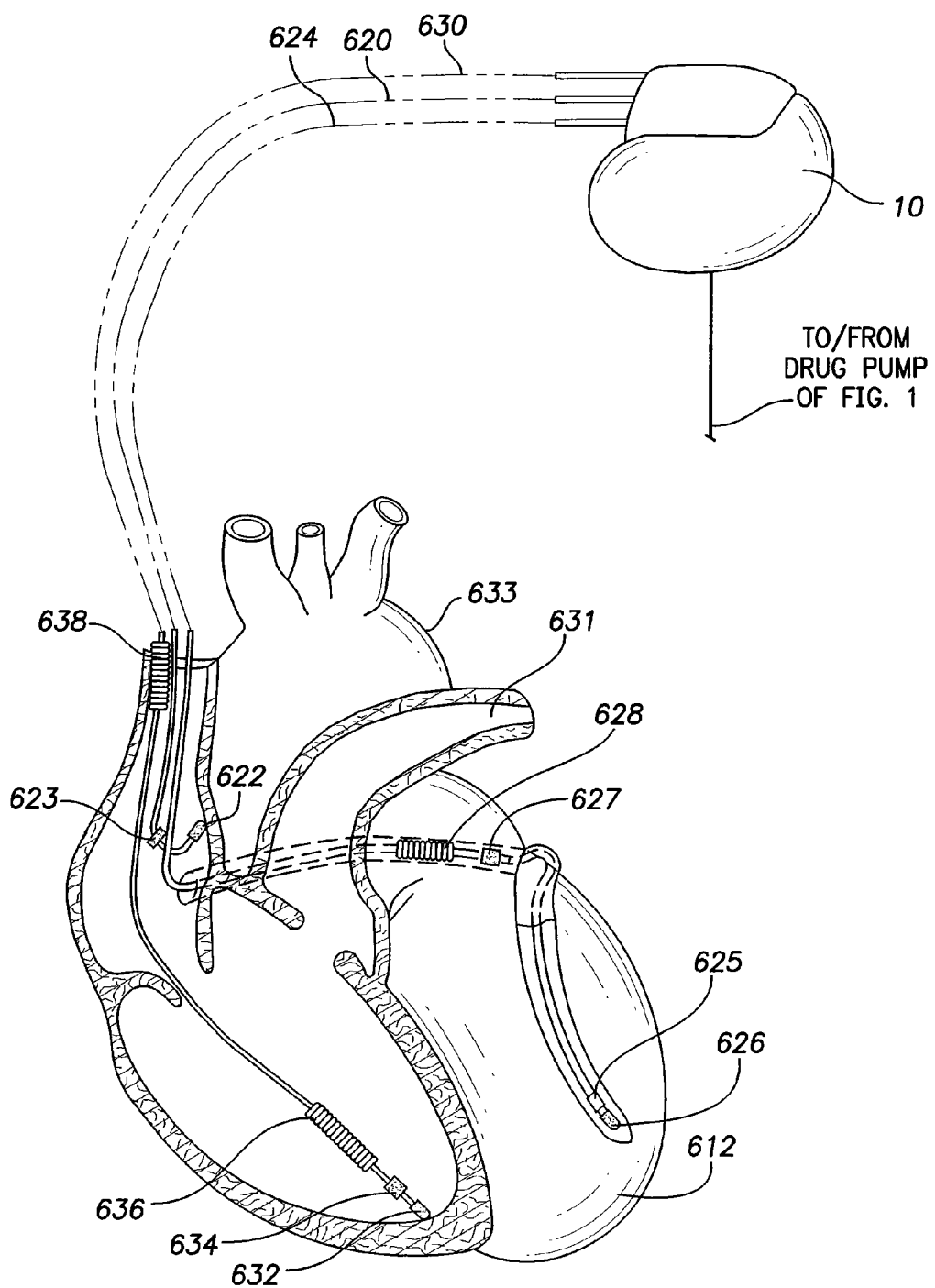
FIG. 20 is a simplified, partly cutaway view, illustrating the pacer/ICD of FIG. 1 along with a set of leads implanted in the heart of the patient.

To these and other ends, implantable medical system 8 includes a pacer/ICD/CRT device 10 or other cardiac stimulation device equipped to detect vector-based impedance measurements along vectors between various pairs of electrodes within a set of leads 12. In the examples described herein, the measurements are impedance measurements but other related parameters might be detected such as admittance. The device is further equipped to convert the vector-based impedance values into relative near-field impedance values corresponding to individual electrodes. Alternatively, the conversion of the vector-based impedance measurements to the corresponding near-field impedance measurements may be performed by an external device or a web-based application following transmission of the vector-based impedance measurements to the external device or an internet-based server. Various cardiac parameters are then determined by the device based on the near-field impedance values, such as LAP or LV EDV. For brevity herein, implantable device 10 will be referred to as a pacer/ICD but it should be understood that other devices such as standalone CRT devices may instead be employed. Note also that in FIG. 1, only two leads are shown. A more complete representation of a set of leads is illustrated in FIG. 20, which is discussed below.

Depending upon the conditions or parameters detected, the pacer/ICD can issue warning signals, if appropriate. For example, if LAP is found to exceed a threshold indicative of HF or is rapidly increasing toward the threshold, warning signals may be generated to warn the patient, either using an internal warning device (which can be part of the pacer/ICD) or using an external bedside monitor/handheld warning device 14. The internal warning device may be a vibrating device or a "tickle" voltage device that, in either case, provides perceptible stimulation to the patient to alert the patient so that the patient may consult a physician. In one example, once the warning is felt, the patient positions an external warning device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this warning/notification technique, see U.S. patent application Ser. No. 11/043,612, filed Jan. 25, 2005, of Kil et al., now U.S. Pat. No. 7,502,644.

If a bedside monitor is provided, the bedside monitor provides audible or visual alarm signals to alert the patient or caregivers, as well as providing textual or graphic displays. In addition, any diagnostic information pertaining to a deteriorating cardiac condition of the patient is transferred to the bedside monitor or is stored within the pacer/ICD for subsequent transmission to an external programmer (not shown in FIG. 1) for review by a physician or other medical professional. The physician may then prescribe therapies to address the condition. The physician may also adjust the operation of the pacer/ICD to activate, deactivate or otherwise control any therapies that are automatically applied. The bedside monitor may be directly networked with an internet network site or a centralized computing system 16 for immediately notifying the physician of any urgent medical condition. The centralized system may include such systems as Merlin.Net of St. Jude Medical, which may be used in conjunction with bedside monitors or similar devices such as the HouseCall™ remote monitoring system or the Merlin@home systems, also of St. Jude Medical.

In response to an increasing and excessive LAP level or in response to the detection of HF or PE, the device can initiate various pacing therapies. One such therapy is CRT, which seeks to normalize asynchronous cardiac electrical activation and the resultant asynchronous contractions by delivering synchronized pacing stimulus to the ventricles. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus And Method For Treatment Of Congestive Heart Failure"; U.S. Pat. No. 6,628,988 to Kramer et al., entitled "Apparatus And Method For Reversal Of Myocardial Remodeling With Electrical Stimulation"; and U.S. Pat. No. 6,512,952 to Stahmann et al., entitled "Method And Apparatus For Maintaining Synchronized Pacing".

In addition to CRT, other forms of therapy may also be controlled by the pacer/ICD in response to the detection of HF and PE or in response to changes in LAP or other cardiac parameters detected using the near-field impedance or admittance values. In this regard, if the implanted system is equipped with a drug pump or drug infusion device 18, appropriate medications may be automatically administered upon detection of a significant increase in LAP due to heart failure or cardiogenic PE. For example, medications may be delivered directly to the patient via the drug pump, if warranted. Alternatively, if a drug pump is not available, the patient may be provided with instructions—generated depending on LAP estimates or other parameters—specifying the dosage of various heart failure medications to be taken. Exemplary heart failure medications include angiotensin-converting enzyme (ACE) inhibitors such as captopril, enalapril, lisinopril and quinapril, diuretics, digitalis, nitrates, beta-blockers, inotropes, and other compounds. Depending upon the particular medication, alternative compounds (e.g., intravenous or subcutaneous agents) may be required for use in connection with an implantable drug pump. Routine experimentation may be employed to identify medications for treatment of heart failure or other conditions that are safe and effective for use in connection with an implantable drug pump. Dosages may be titrated based upon the severity of HF as determined from LAP or other parameters.

Figure 2:
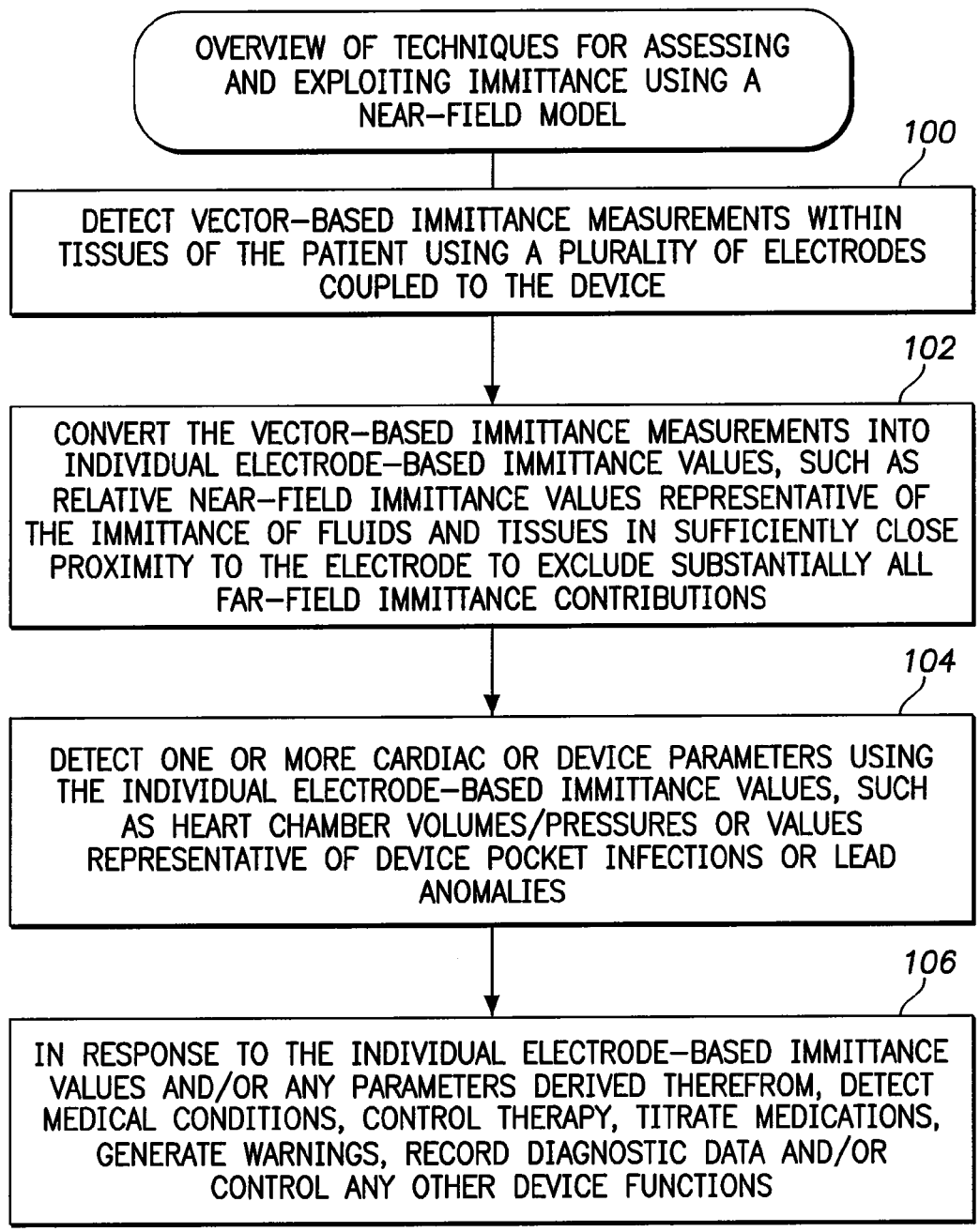
FIG. 2 provides an overview of techniques for assessing and exploiting near-field immittance values that may be performed by the system of FIG. 1.

FIG. 2 broadly summarizes the near-field assessment and exploitation techniques performed by the pacer/ICD of FIG. 1 or other suitably-equipped implantable devices. That is, the figure illustrates a general method that exploits the aforementioned near-field model. At step 100, the device detects vector-based immittance measurements (i.e. impedance and/or admittance values) within tissues of the patient using a plurality of electrode pairs coupled to the device. At step 102, the device converts the vector-based immittance measurements into individual electrode-based immittance values, such as relative near-field immittance values representative of the immittance of fluids and tissues in sufficiently close proximity to the electrode to exclude substantially all far-field immittance contributions.

At step 104, the device detects one or more cardiac parameters or device operation parameters using the individual electrode-based immittance values, such as heart chamber volumes/pressures or values representative of device pocket infections or lead anomalies. At step 106, in response to the individual electrode-based immittance values and/or the various parameters derived therefrom, the device selectively controls therapy, titrates medications, generates warnings, records diagnostic data or controls any other device function. As noted above, it should be understood that any function that the device can perform or control, alone or in combination with other devices, is a "device function." This includes, but is not limited to, detecting medical conditions such as PE or HF, detecting cardiac parameters such as LAP or LV EDV, detecting pacing/defibrillation lead anomalies, detecting infection, controlling pacing, and generating and transmitting diagnostic information, etc.

Hence, FIGS. 1 and 2 provide an overview of an implantable medical system/method for assessing and exploiting impedance and/or admittance values using the near-field model and for controlling numerous device functions in response thereto. Embodiments may be implemented that do not necessarily perform all of the functions described herein. For example, embodiments may be implemented that determine near-field immittance and detect medical conditions in response to changes in near-field immittance but do not automatically initiate or adjust therapies. Moreover, systems provided in accordance with the invention need not include all of the components shown in FIG. 1. In many cases, for example, the system will include only a pacer/ICD and its leads. Implantable drug pumps are not necessarily implanted. These are just a few exemplary embodiments. No attempt is made herein to describe all possible combinations of components that may be provided in accordance with the general principles of the invention. In addition, note that the particular locations of the implanted components shown in FIG. 1 are merely illustrative and may not necessarily correspond to actual implant locations. Although internal signal transmission lines provided are illustrated in FIG. 1 for interconnecting various implanted components, wireless signal transmission may alternatively be employed, where appropriate.

Note that the examples described herein are directed to bipolar impedance rather than quadripolar impedance. In order to measure impedance, the device sends out a current between a pair of electrode (herein "current electrodes") and records voltage from a pair of electrodes (herein "voltage electrodes.") The voltage electrodes may or may not be the same as the current electrodes. In the case where the voltage electrodes are the same as the current electrodes, the impedance collected is called "bipolar impedance." If not the same, then the impedance is called "tripolar or quadripolar impedance" depending on whether one pair of voltage and current electrodes is different ("tripolar") versus two pairs of voltage and current electrodes are different ("quadrapolar"). Although some aspects of the invention are generally and broadly applicable to either bipolar impedance or quadripolar impedance, the interpretation of the resulting "individual electrode-based" impedance values may be unclear, particularly if the current and voltage nodes are not in close proximity to one another. Hence, the invention is primarily intended to be practiced for use with bipolar impedance or for use in quadripolar cases where the current and voltage nodes are in close proximity to one another.

In the following section, additional explanatory information regarding the near-field model is provided so as to expand upon and clarify the brief descriptions of the near-field model discussed above.

The Near-Field Model

The traditional far-field model of impedance characterizes vector-based impedance measurements as representing the impedance to electrical flow between a pair of electrodes, including far-field contributions to that impedance. With the near-field model, a new perspective is provided and exploited wherein the impedance measurements made using a pair of electrodes is deemed to represent the impedance contributions from local tissues and fluids near the electrodes under the assumption that any contribution to the measurement from the far-field of the inter-electrode space can be ignored. For example, for the LVring to case vector, the measured impedance along this vector corresponds to the summation of the near-field impedance associated with the LVring electrode and the near-field impedance associated with the device case (i.e., LVr+Case). The near-field impedance associated with the LVring electrode corresponds to the impedance associated with the bare LVring electrode in combination with the impedance associated with the tissues and fluid surrounding the LVring electrode within the coronary vein and the adjacent left ventricular myocardium, pericardial space, and lung tissue within a short distance from the LVring electrode (~1-2 cm); the near-field impedance associated with the Case electrode corresponds to the impedance associated with the bare device case in combination with the impedance associated with the local tissues and fluid surrounding the device case within the subcutaneous device pocket and adjacent tissues within a short distance from the device case (~2-5 cm).

Figure 3:
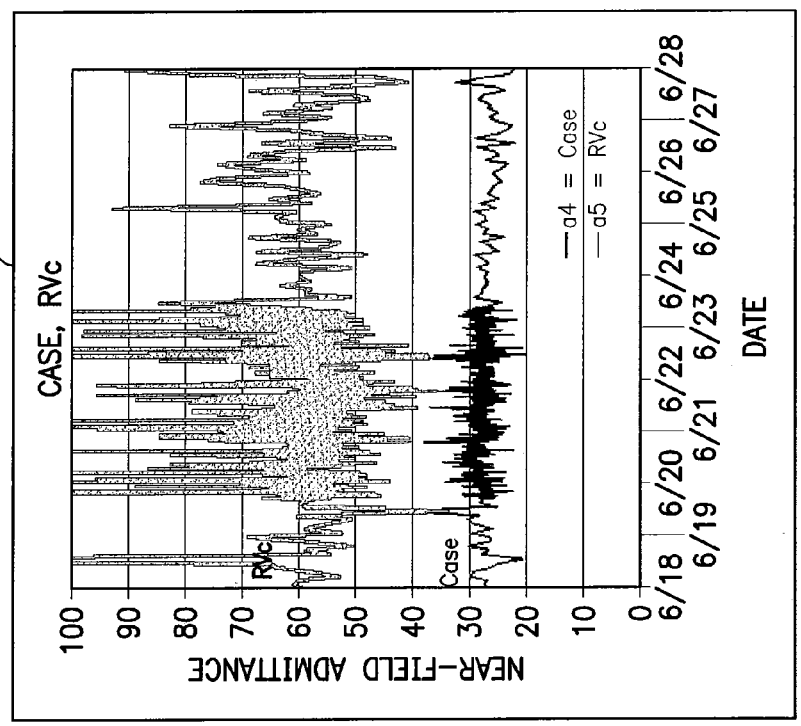
FIG. 3 is a graphical illustration comparing the far-field and near-field models of impedance, the latter of which is exploited by the method of FIG. 2.

That is, with the near-field model, the measured impedance along a vector comprising two electrodes (A and B) is simplified to reflect a superposition (i.e. summation) of the near-field impedance measurements associated with each of the individual electrodes, while assuming that any contribution to the measured vector-based impedance from the far-field inter-electrode space can be ignored. With the near-field model the impedance to current flow along a given vector occurs primarily at the electrode-tissue interface of each of the electrodes (A and B), while the contribution to the measured vector-based impedance from the tissues and fluid in the far-field is minimal and, therefore negligible, because the current finds the path of least resistance once the current is passed the electrode-tissue interface when travelling from electrode A to electrode B. This is generally illustrated in FIG. 3 for an example wherein a bipolar intrathoracic impedance vector consists of two electrodes (A and B) such as the LVring and case housing. The measured vector-based impedance is regarded under the near-field model as being the sum of the near-field impedances associated with each of the electrodes. As noted above, this may be represented as:

Far-field Model: Impedance=A to B=Field between A and B

Near-field Model: Impedance=A+B=Near-Field A+Near-Field B

In FIG. 3, the far-field model is shown via graph 108. The near-field model is shown via graph 109, with local near-field contributions 110 and 111 specifically identified. The near-field concept is, however, not limited to a single pair of electrodes but is also applicable to multi-polar vectors (e.g., tripolar, quadripolar, etc.)

Figures 4A, 4B:
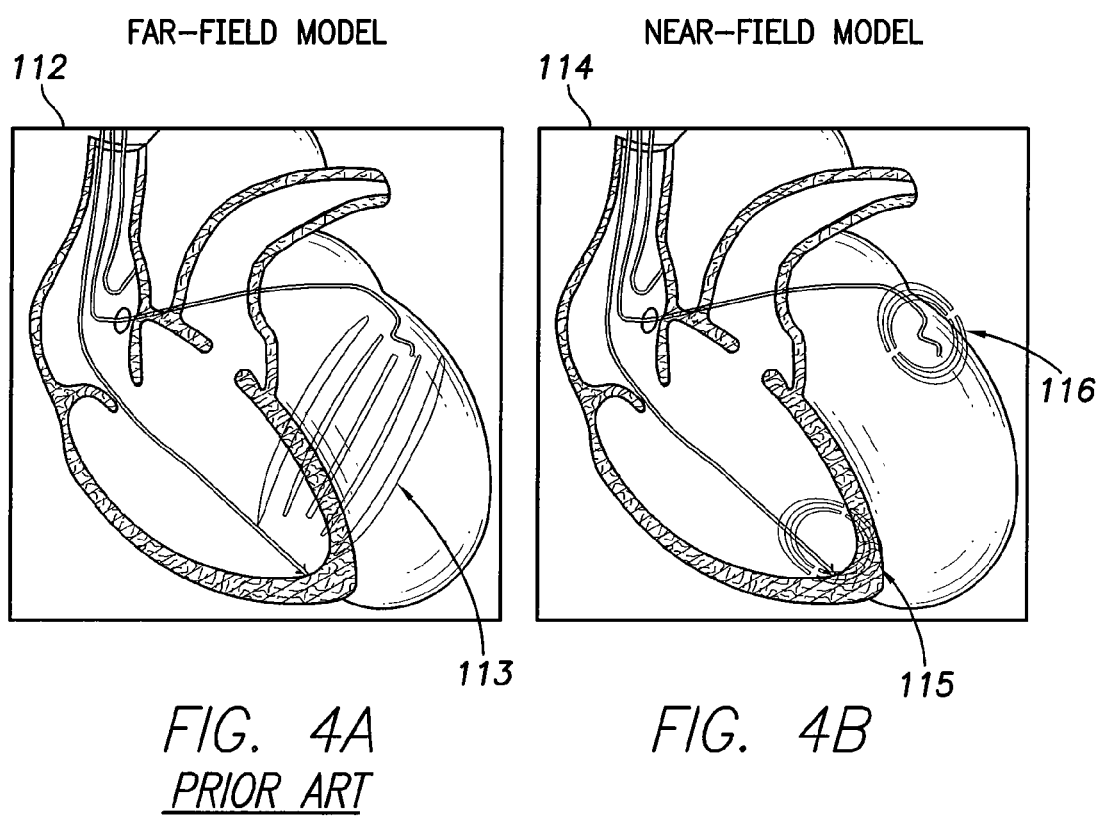
FIG. 4 provides simplified, partly cutaway views, of the heart of a patient along with various leads, and which particularly illustrates a comparison of far-field and near-field impedance zones, the latter of which is exploited by the method of FIG. 2.

In FIG. 4, the far-field model is shown via heart 112 and far-field zone 113. The near-field model is shown via heart 114 and local near-field zones 115 and 116. For the example of a ring electrode of an RV lead implanted within the apex of the RV, the relative near-field generally corresponds to a field localized within the right ventricular apex about 1-2 cm around the ring electrode. This RV apical field is in direct communication with the RV blood volume and contains the scar tissue surrounding the RVr electrode in combination with the adjacent apical myocardial tissue. As previously mentioned, for a ring electrode of an LV lead implanted within a coronary vein, the relative near-field is localized to the coronary vein and the adjacent LV myocardium, pericardial space, and potentially adjacent lung tissue if in close proximity. During each cardiac and respiratory cycle there is a continuous change in the amount of tissue and blood/fluid that is in direct contact with the RVr and LVr electrodes or within the near-field zones of each of the electrodes, which directly influences the measured near-field impedance associated with the RVr and LVr electrodes throughout the cardiac and respiratory cycles. During diastole the myocardium relaxes and the ventricles and coronary veins fill with blood causing more blood to surround the RVr and LVr electrodes and less myocardial tissue to be in direct contact with the electrodes. This increase in surrounding blood volume and resulting decrease in myocardial tissue contact with the electrodes causes the near-field impedance associated with the RVr and LVr electrodes to decrease during diastole. Similarly, during systole there is a decrease in ventricular and coronary venous blood volume as the myocardium squeezes. The decrease in surrounding blood volume and resulting increase in myocardial tissue contact with the electrodes as the ventricles squeeze causes the near-field impedance associated with the RVr and LVr electrodes to increase during systole. During diastole the more filling that occurs the greater the decrease in the near-field impedance. During systole the more squeezing that occurs the greater the increase in the near-field impedance.

The near-field concept is not limited to pairs of electrodes. As shown in FIG. 5, the near-field model is applicable to more generalized embodiments such as those that relate "impedance triangle" measurements Z1, Z2 and Z3 made along three lead configuration vectors (A to C, A to B, and B to C) or more general "impedance polygonal" measurements. In FIG. 5, an impedance triangle model is shown via vector graph 117. Exemplary locations of three such electrodes within a patient are shown on the right via drawing 118. In this regard, an impedance triangle may be defined in which the impedance along each lead configuration vector can be related to the summation of the impedances associated with each of the electrodes forming the vector, and where the addition and subtraction of multiple vectors may be used to derive the near-field impedance associated with an individual electrode.

Note that the blood/fluid volume surrounding a given electrode (e.g., RVr or LVr) is dependent on the degree of scar tissue formation and myocardial tissue surrounding and in direct contact with the electrode, which is dependent on the implant site selected in combination with the resulting healing response. The variability in the pattern of scar tissue and myocardial tissue around an electrode and its implant site produces a variable pattern of blood/fluid washout against the electrode pair (e.g., RVr+LVr) in combination with a variable pattern of electrode and surrounding tissue contact throughout the cardiac and respiratory cycles, such that the continuous vector-based impedance signal recorded during the cardiac and respiratory cycles on a beat-to-beat basis (i.e., the impedance signal acquired at a high sampling rate, e.g., 128 Hz) can vary significantly from patient to patient and becomes complex to interpret. The near-field model makes it possible to derive the near-field impedance signal for a single cardiac electrode (e.g., RVr and LVr) such that the interpretation of the impedance waveform within any given cardiac and respiratory cycle is simplified. This is because the cardiac and respiratory cycle effects are isolated to a single electrode rather than multiple electrodes. This will be explained further below with reference to various examples where the near-field model allows physical phenomena associated with particular electrodes to be easily identified.

Note also that the size of the near-field for each electrode depends on multiple factors, such as the physical size of the electrode, the materials used, the amount of contact with blood/fluid versus tissue, scar tissue thickness, ventricular wall thickness, etc. In general, the size of the near-field is larger for electrodes with larger surface areas, such as the device housing electrode (Case) or coil electrodes (RVcoil or SVCcoil). For the device case electrode, the near-field generally corresponds to a field localized within the entire device pocket and potentially tissues slightly farther away, such as the underlying chest wall and potentially the adjacent lung tissue. The near-field for the case is larger than for an individual lead ring or tip electrode because of the relatively larger surface area of the case electrode. Consider for example the following two impedance "triangles": (a) a triangle with small electrodes: RVring-LVring, LVring-RAring, RAring-RVring and (b) a triangle with large electrodes: RVcoil-Case, SVCcoil-Case, RVcoil-SVCcoil. The near-field impedance associated with the smaller ring electrodes reflect phenomena occurring within tissues very close to the electrode (~1-2 cm), whereas the near-field impedance associated with the larger case or coil electrodes reflect phenomena occurring within tissues both very close to the electrode and somewhat farther away from the electrodes (~2-5 cm). Both are deemed herein to be "relative" near-field phenomena so as to distinguish from true far-field phenomena. Based on experimental data and simulations, the size of the near-field is estimated to be within a close vicinity (<1 to 5 cm) of most electrodes. Otherwise routine experimentation can be employed to more precisely determine the size of the near-field surrounding any given electrode.

In view of these considerations, the term "near-field" as used herein should be interpreted as "relative near-field" since the exact size of the near-field associated with a given electrode depends on various factors. In some descriptions herein, the term "relative" is applied to near-field so as to remind the reader that the near-field impedances are near-field relative to far-field measurements, but it should be understood that, even in cases where the term "relative" is not specifically used, "relative near-field" is intended. It should also be noted that if the electrodes of a given pair are very close to one another there could be overlap between the near-field of one electrode and the near-field of the other. In addition, the term "fluid" as used herein should be interpreted to mean any fluid that may physically be present within the body, such as blood, pericardial fluid, pleural fluid, peritoneal fluid, serous fluid within a device pocket, interstitial fluid, purulent fluid, etc.

As explained above, aspects of the invention are generally and broadly applicable to either bipolar impedance or quadripolar impedance. In this regard, for a quadripole example where three current electrodes A, B and C are used along with three voltage electrodes D, E and F, respectively (that are not in close proximity to corresponding current electrodes), a set of linear equations can be solved for D, E and F, though the interpretation of the results may be unclear, particularly from a clinical standpoint. For a quadripole example where A and D are in close proximity to one another (i.e. within each other's relative near-fields), where B and E are in close proximity, and where C and F are in close proximity, then the quadripolar impedance reduces to a bipolar impedance and the clinical interpretation of the resulting near-field impedances is as discussed herein below. Hence, the techniques described herein are primarily intended to be practiced for use with bipolar impedance or for use in quadripolar cases where the current and voltage nodes are in close proximity to one another, which is typically the case for tip/ring pairs. For example, the RVtip and RVring electrodes are typically in close proximity such that they are within each other's relative near field.

Exemplary Near-Field Impedance-Based Assessment Techniques

Figure 6:
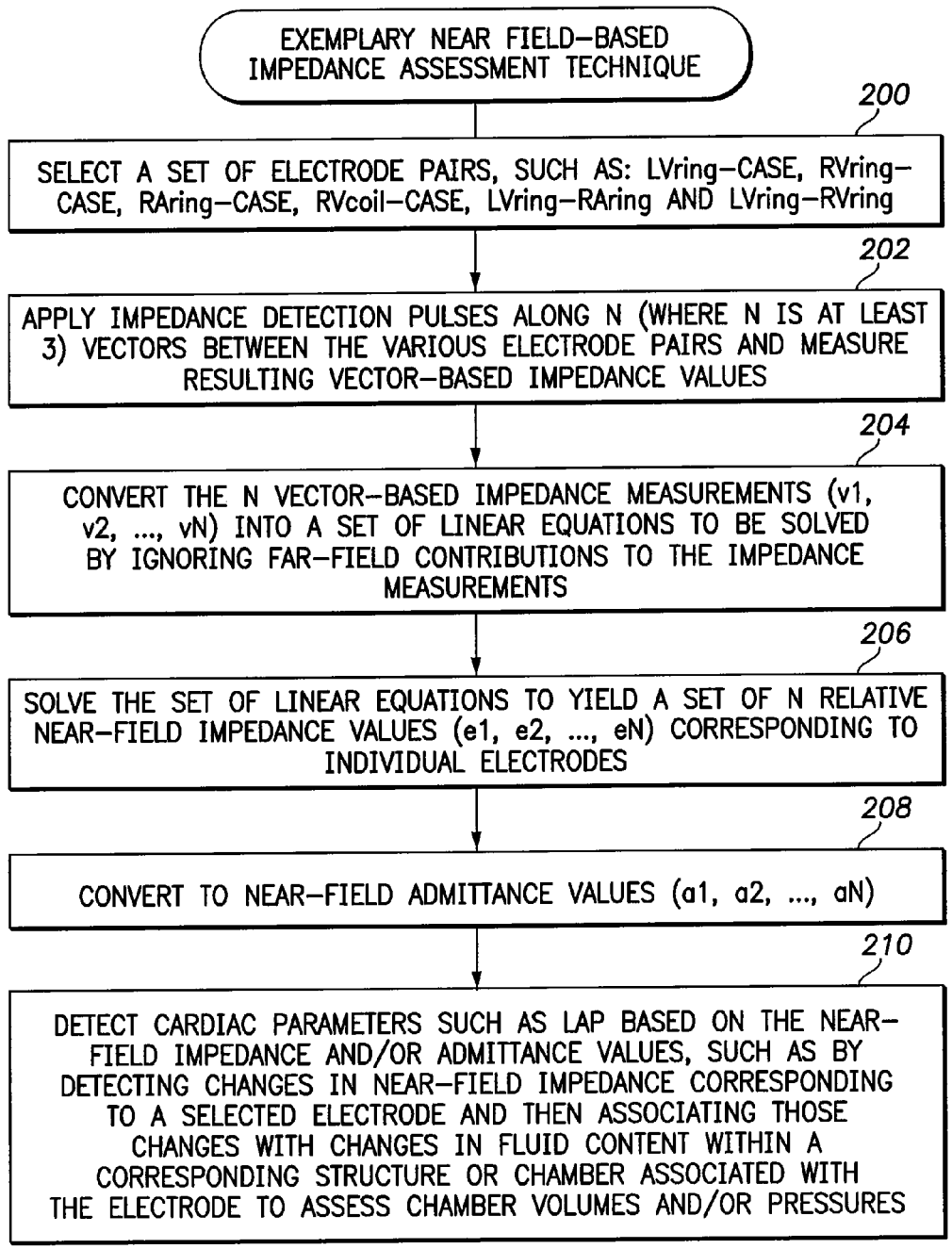
FIG. 6 illustrates an exemplary method performed in accordance with the general technique of FIG. 2, wherein N linear equations are exploited to determine N near-field impedance values from vector-based impedance measurements.

Referring next to FIG. 6, illustrative techniques will be described that exploit the near-field model in connection with an example wherein vector-based impedance is initially detected. Beginning at step 200, the pacer/ICD selects a set of electrode pairs from among a set of available electrodes of an implanted lead system, such as the set consisting of: LVring-case, RVring-case, RAring-case, RVcoil-case, LVring-RAring and LVring-RVring. For a case where there are N individual electrodes, the device, at step 202, applies impedance detection pulses along N vectors (where N is at least 3) between the various electrode pairs and measures N resulting vector-based impedance values. (Note that, although it is sufficient for the device to acquire measurements along N vectors to derive the near-field impedance measurements associated with N electrodes, a greater number of vectors can be used, such as N+1, to determine the near-field impedances of the N electrodes. The use of more vectors (such as N+1) than electrodes (N) can be exploited to validate the solution for N.)

The impedance signals are obtained by transmitting electrical current between a pair of electrodes and subsequently measuring the voltage between the same or another pair of electrodes. The impedance may be calculated as the ratio of the measured voltage to the transmitted current. In some examples, a tri-phasic impedance pulse waveform is employed to sense the impedance signal. The tri-phasic waveform is a frequency-rich, low energy waveform that provides a net-zero charge and a net-zero voltage. An exemplary tri-phasic pulse waveform is described in detail in U.S. patent application Ser. No. 11/558,194, of Panescu et al., filed Nov. 9, 2006, entitled "Closed-Loop Adaptive Adjustment of Pacing Therapy based on Cardiogenic Impedance Signals Detected by an Implantable Medical Device."

At step 204, the device converts the vector-based impedance measurements (v1, v2, . . . , vN) into a set of linear equations to be solved by ignoring far-field contributions to the impedance measurements. That is, the device exploits the near-field model by recognizing that far-field contributions can be advantageously ignored. At step 206, the device then solves the set of linear equations to yield a set of N near-field impedance values (e1, e2, . . . , eN) corresponding to the N individual electrodes. At step 208, the device converts the near-field impedance values to near-field admittance values (a1, a2, . . . , aN) by, for example, taking the reciprocal of each. At step 210, the device then detects cardiac parameters such as LAP based on the near-field admittance values (or on the near-field impedance values), such as by detecting changes in near-field impedance corresponding to a selected electrode and then associating those changes with changes in fluid content within a corresponding structure or chamber associated with the electrode to assess chamber volumes and/or pressures.

As noted, the relative near-field impedance/admittance value for each electrode reflects the degree of tissue contact and fluid volume surrounding the electrode. Each electrode can be uniquely associated with a specific location within the heart or subcutaneous tissues. The importance of this association between each electrode and one corresponding anatomical location/structure is that it becomes simpler to interpret from a clinical perspective any changes that occur within the near-field impedance measurements belonging to an individual electrode. This is because a change observed in the impedance associated with a given electrode (e.g., LVring) may then be used to indicate a change in tissue contact and/or fluid content within the corresponding location/structure (e.g., coronary vein, LV myocardium, pericardial space, and potentially adjacent lung tissue). Such a one-to-one association cannot readily be made when interpreting measurements of vector-based impedance values because each vector measurement reflects a combination of events occurring among the various electrodes that comprise the vector.

Figure 7:
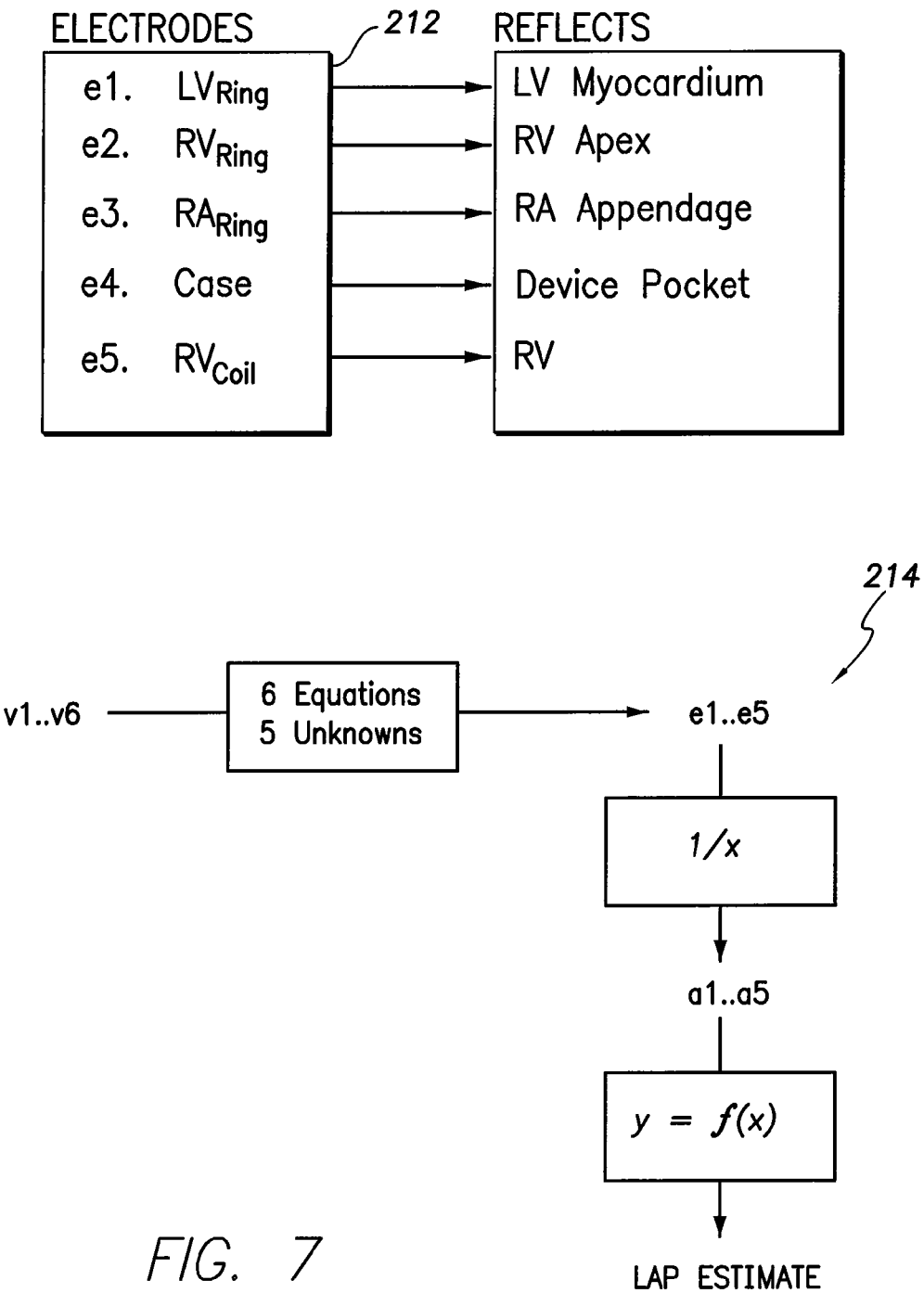
FIG. 7 is a schematic diagram illustrating aspects of the procedure of FIG. 6 for an example where six vectors are used to assess five impedance values, and particularly illustrating the estimation of LAP from near-field admittance.

FIG. 7 schematically illustrates the exemplary procedure of FIG. 6 applied to an example where six impedance vectors (V1 . . . V6) are measured to determine the near-field impedances of five electrodes (e1 . . . e5). That is, FIG. 7 illustrates an example where N+1 vectors are used to determine N near-field impedance values. Block 212 summarizes the relationship between particular electrodes and the corresponding structures to which the near-field impedance values might relate. The association between each electrode and the anatomical structure shown is for illustrative purposes and is not intended to be restrictive in any way. For example, the LVring electrode may be associated with the adjacent coronary vein, LV myocardium, pericardial space, and lung tissue. Similarly, the RVring electrode may be associated with the adjacent RV apical region, the RV septal region, or the RV outflow tract region depending on the chosen implant site. The right atrial (RA) ring electrode (herein RAring or RAr) may be associated with the RA appendage region or the inter-atrial septal region depending on the implant site chosen. The device case electrode may be associated with the subcutaneous pocket containing the device and potentially the underlying chest wall and adjacent lung tissue depending on the thickness of the chest wall and proximity of the lung tissue. The RVcoil electrode may be associated with the RV. For each electrode the greatest contribution to the measured near-field impedance originates from the tissues and fluid that are in direct contact and closest to the electrode, while the contribution to the measured near-field impedance from tissues and fluid slightly farther away is substantially less since the contribution decreases with the square of the distance from the electrode. Flow diagram 214 schematically summarizes the conversion of vector-based impedance measurements (for an example with five electrodes) into near-field impedance values, and then to near-field admittance values, and ultimately to estimated LAP values based, in this particular example, on a linear correlation. In some cases, the LAP estimates are referred to as zLAP values.

FIG. 8 summarizes the conversion of a set of six exemplary vector-based impedance measurements 216 into five individual electrode near-field values via matrix inversion formulae 218. The solution in matrix form 219 is also provided in the figure. The five equations are also included here for reference:

$$e1=[(v1-v2)+v6+(v1-v3)+v5]/4=[(LVr-RVr)+(LVr+RVr)+(LVr-RAr)+(LVr+RAr)]/4=LVr$$

$$e2=[(v2-v1)+v6]/2=[(RVr-LVr)+(LVr+RVr)]/2=RVr$$

$$e3=[(v3-v1)+v5]/2=[(RAr-LVr)+(LVr+RAr)]/2=RAr$$

$$e4=[(v1-e1)+(v2-e2)+(v3-e3)]/3=\text{Case}$$

$$e5=v4-e4=RVc$$

The set of equations provided are not intended to be restrictive in any sense and are used merely as an illustrative example. Other sets of equations may be derived depending on the number of vector measurements available and the number of electrodes utilized, so long as the number of vectors available is greater or equal to the number of electrodes available and so that there is at least one set of equations or more which form an impedance triangle.

Figure 9:
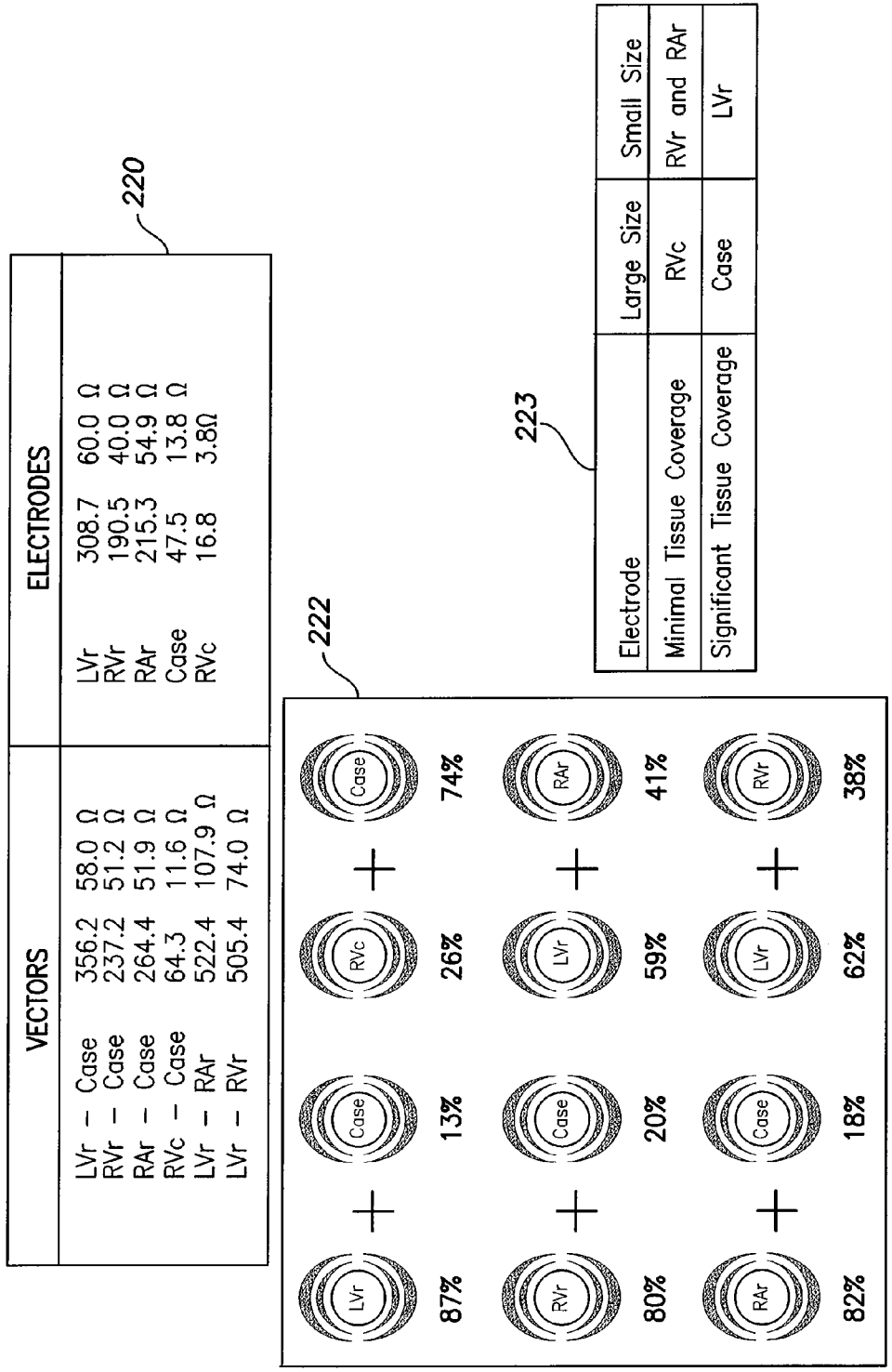
FIG. 9 is a diagram illustrating exemplary near-field impedance values calculated by the procedure of FIG. 6, and particularly illustrating the various near-field contributions to initial vector-based impedance measurements.

FIG. 9 provides exemplary values for the vector-based impedances and the corresponding near-field impedances by way of chart 220 derived from the analysis of data from human subjects. Take, for example, the vector-based impedance of the RVcoil-case pair, which is shown to be about 64.3 ohms. Under the near-field model, this is formed from the combination of the RVcoil near-field impedance (about 16.8 ohms) plus the device case near-field impedance (about 47.5 ohms), which when added together provide the full 64.3 ohms of pair-based impedance. The figure additionally illustrates the relative contribution of the near-field impedances between the various pairs of electrodes for each of the six vectors via graph 222. For the RVcoil-case electrode pair, the majority of the vector-based impedance measurement is originating from the device case tissue interface (74%), while a significantly smaller portion (26%) is originating from the RVcoil tissue interface. As such, a pair-based impedance measurement along that vector primarily represents the impedance near the case electrode within the device pocket rather than near the RVcoil within the RV (or in the far-field region therebetween.) Thus, any significant change in the RVcoil-case impedance vector measurement primarily reflects changes that are occurring within the device pocket and the immediate adjacent region rather than within the RV or the farther located lung tissues located in the region between the RVcoil and the device case. This is to be contrasted with the impedance measurement derived from the LVring-case electrode pair, for which the majority of the vector-based impedance measurement is originating from the LVring electrode-tissue interface (87%), while a significantly smaller portion (13%) is originating from the device case tissue interface. The LVring electrode contributes more to the vector-based impedance measurement than the device case electrode because of the smaller surface area associated with the LVring at the electrode-tissue interface in comparison to the Case electrode. Thus, any significant change in the LVring-case impedance vector measurement primarily reflects changes that are occurring in the coronary vein region where the LVring electrode is implanted, along with the adjacent LV myocardium, pericardial space, and nearby lung tissue if in close proximity. As another example, for the LVring-RAring electrode pair, the amount of near-field impedance originating from the LVring electrode-tissue interface (59%) is of the same order of magnitude as the amount of near-field impedance originating from the RAring electrode-tissue interface (41%.) There is comparatively little difference between the LVring and the RAring near-field impedances in this example because both have similar electrode sizes. However, because of the likely presence of more scar tissue around the LVring electrode within the coronary vein in comparison to the amount of scar tissue around the RAring within the RA appendage the relative contribution from the LVring electrode is slightly greater. The relative contributions to the vector-based impedance measurements illustrated within FIG. 9 represent just one type of useful data that can be obtained by deriving and analyzing near-field impedances.

FIG. 9 also provides a summary block 223 that divides the five electrodes into four groups based on the electrode characteristics of size (large or small) and the expected amount of tissue coverage (minimal or significant) typically encountered in-vivo. The larger the electrode size and the less tissue covers the electrode, the lesser will be the measured near-field impedance. The smaller the electrode size and the more tissue that covers the electrode, the greater will be the measured near-field impedance. The RVcoil was found to have the lowest near-field impedance because it has a relatively large size electrode, which is implanted within the RV cavity where it is surrounded by a large volume of blood with minimal tissue coverage. In contrast the LVring electrode was found to have the highest near-field impedance. This is because the LVring electrode has a relatively small size electrode and is implanted within a coronary vein where part of the electrode is in direct contact with the epicardial tissue. In addition, significant scar tissue is likely to form around the LVring electrode particularly when the distal-end of the lead is wedged far into a coronary vein, such that blood flow around the electrode becomes obstructed.

It has also been found that the integrity of the pericardial space can have a significant impact on the measured near-field impedance associated with the LVring electrode. A patient that has a history of a prior open-heart surgery procedure or a history of pericarditis will typically develop scarring within the pericardial space and the absence of free flowing pericardial fluid around the heart. The presence of a scarred pericardial space and the absence of free-flowing pericardial fluid would typically cause the near-field impedance of the LVring electrode to be larger in comparison to the near-field impedance for the same electrode when implanted in a patient where there is absence of scar tissue within the pericardial space and there is free-flowing pericardial fluid bathing the epicardial surface of the heart. It has also been found that in patients with a scarred pericardium the acute effect of a change in posture has minimal effect on altering the amount of tissue/fluid contacting the LVring electrode because the LVring electrode is relatively fixed to the surrounding tissues and pericardial sac, such that the measured near-field impedance will remain relatively constant until a sufficient amount of time has permitted additional fluid to enter or leave the near-field surrounding the LVring electrode. This is in contrast to a patient with an intact pericardial space where changes in posture may acutely cause the heart to shift position within the pericardial space, such that the pericardial sac may acutely become either in-contact or not in-contact with the LVring electrode. This observation has implications when attempting to interpret changes in the impedance signal and will be explained further below in reference to various examples where the near-field model in combination with a posture-sensor allows changes in impedance following a change in posture to be interpreted more easily.

Figure 10:
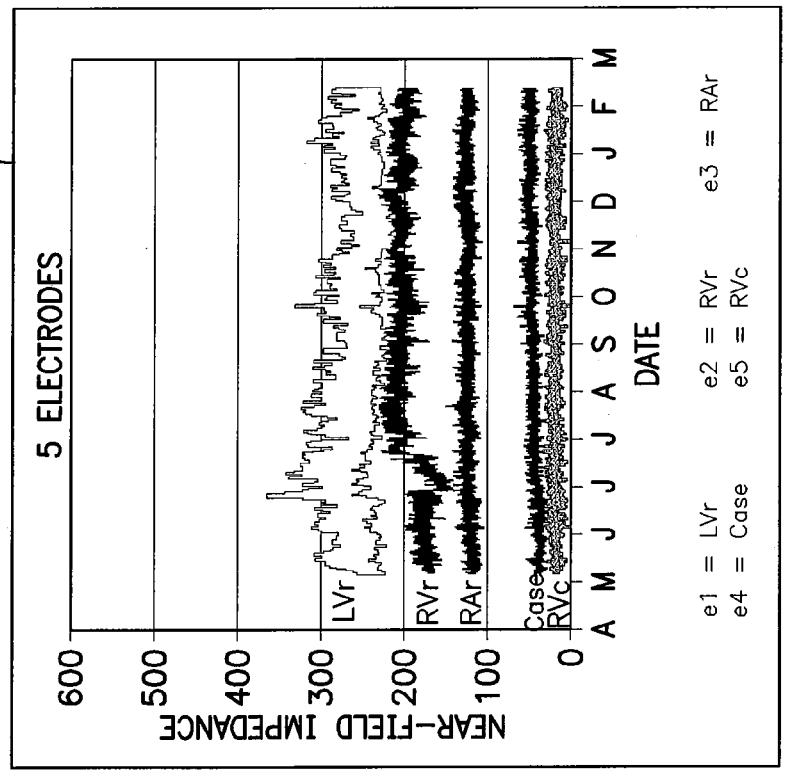
FIG. 10 provides exemplary graphs corresponding to data that can be processed by the procedure of FIG. 6, which particularly illustrate time-varying changes in various near-field impedance or admittance signals derived from vector-based impedance measurements.
Figure 1:
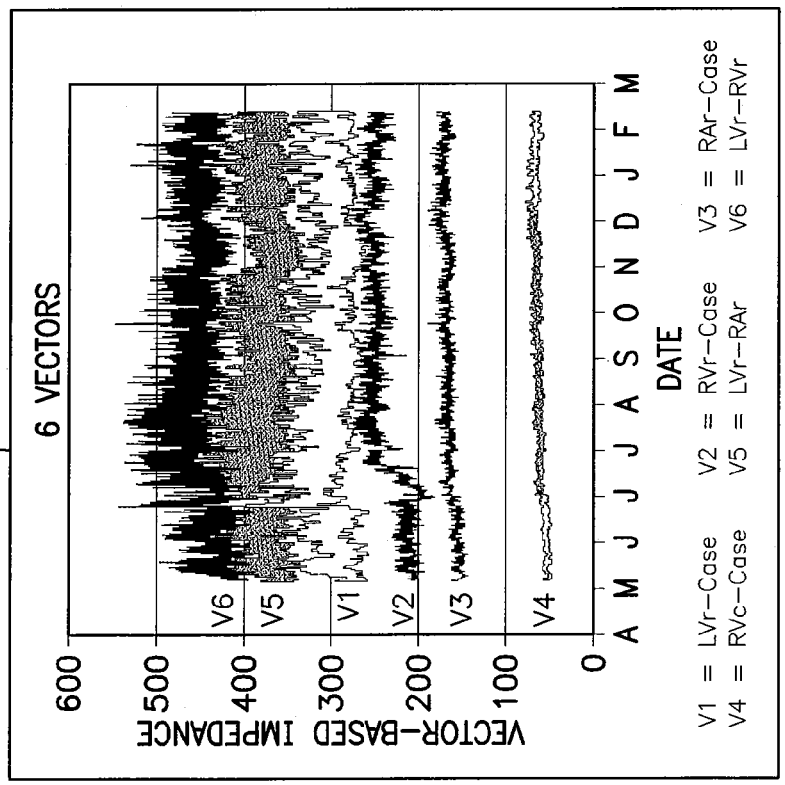
Figure 10:
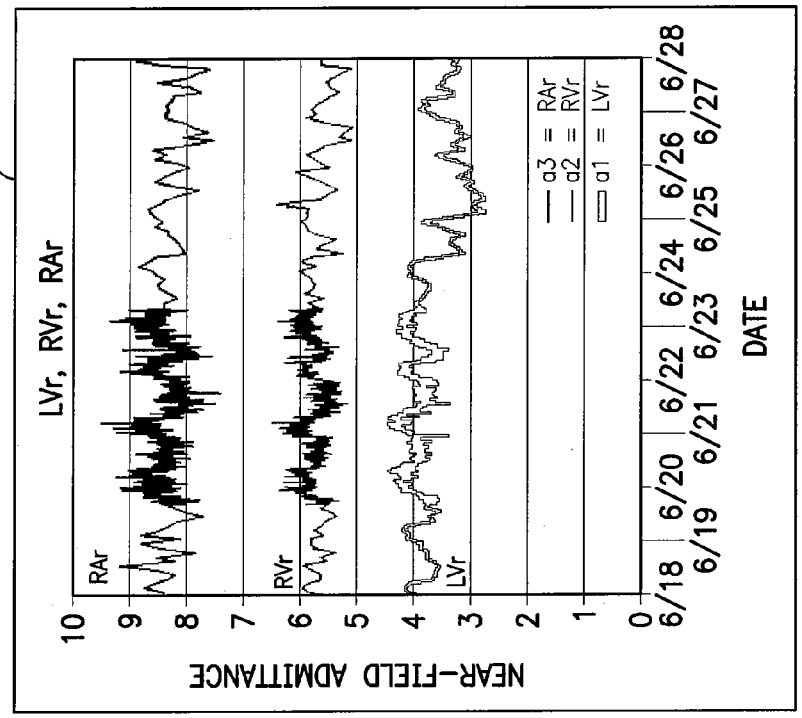

FIG. 10 illustrates time-varying changes in near-field impedance/admittance signals corresponding to various combinations of the individual electrodes from an exemplary human test subject. Referring first to graphs 224 and 226, the relative contribution of each of the electrodes toward each impedance vector can easily be seen as tracked over a nine-month time interval. For example, for the LVring-Case vector, the LVring electrode has a near-field impedance of about 250 ohms, whereas the case electrode has a near-field impedance of about 50 ohms. Thus, the majority of the impedance for this vector is originating from the LVring electrode-tissue interface (250/300=83%). For the RVcoil-Case vector, the RVcoil has a near-field impedance of about 20 ohms, while the device case electrode has a near-field impedance of about 50 ohms. Thus, the majority of the impedance for this vector is originating from the device case tissue interface (50/70=71%).

As already explained, the near-field impedances determined for each of the electrodes can be transformed into near-field admittance values to provide an assessment of the fluid volume surrounding each electrode. Graphs 228 and 230 illustrate the near-field admittance measurements trended over time for the various electrodes. Variable times to stabilization of the near-field admittance measurements following implant can be seen for the various electrodes due to variation in scar tissue maturation times. Immediately following implant edema acutely forms within the tissues around each electrode and causes the near-field admittance to rise. Over the subsequent weeks, the near-field admittance returns back to a baseline as the local edema resolves and tissue healing occurs at the implant site. Depending on the degree of tissue injury at the implant site and the resulting healing response variations in the healing intervals may occur among the various electrodes. This will be addressed further below in reference to various examples.

It can also be seen that the near-field admittance derived for the RVcoil electrode in graph 228 has a significant degree of measurement variability in comparison to the near-field admittance derived for the RVring electrode in graph 230. This is of particular interest because both the RVring and the RVcoil are implanted within the same cardiac chamber. To review this difference further the sampling interval for the acquired impedance signals was increased from a measurement interval of every 2 hours to every 7.5 minutes over a several day period. The near-field admittance data acquired during this higher sampling period is included within a 10-day time window shown in graphs 232 and 234. The near-field admittance for the RVcoil electrode has large magnitude variations (i.e. it is noisy), while the near-field admittance for the RVring electrode has small magnitude variations relative to the average signal level. The near-field admittance signal for the RVcoil is a noisier signal because the larger size coil electrode within the RV is more prone to variability in myocardial tissue contact compared to the smaller size RVring electrode. The importance of this observation is that a vector comprised of the RVcoil and Case electrode pair (RVcoil-Case) essentially only provides useful information from the Case electrode (i.e., Device Pocket) since the RVcoil electrode is too noisy to provide any clinically useful information. Because of the significant degree of noise present within the near-field impedance signal of the RVcoil it is often necessary to average the vector-based impedance signal for the RVcoil-Case vector over multiple measurements (i.e., compute a daily average) in order to extract any clinically meaningful data. The benefit of the near-field model is that less signal averaging may be required when the near-field impedance measurements associated with the device case tissue interface are used to derive the clinical data because the noisy component related to the RVcoil may be subtracted out.

It is also apparent from the data shown in graphs 232 and 234 of FIG. 10 that the near-field admittance signal for the LVring electrode has an excellent signal to noise ratio with clear diurnal variations that may more easily provide clinically useful data. The diurnal variations seen in the near-field admittance signals for the various electrodes are reflective of variations in fluid distribution occurring within the vicinity of each electrode in response to fluid shifts that occur following changes in posture. This diurnal variation may be leveraged for deriving transformation coefficients for an impedance-based LAP estimate (which can also be referred to as zLAP calibration.) zLAP estimation via a linear function (e.g., zLAP=Gain*Admittance+Offset) is discussed more fully below with reference to FIG. 19. The term zLAP is discussed more fully below, with reference to various predecessor patent applications.

Exemplary Near-Field Model-Based Applications

Figure 11:
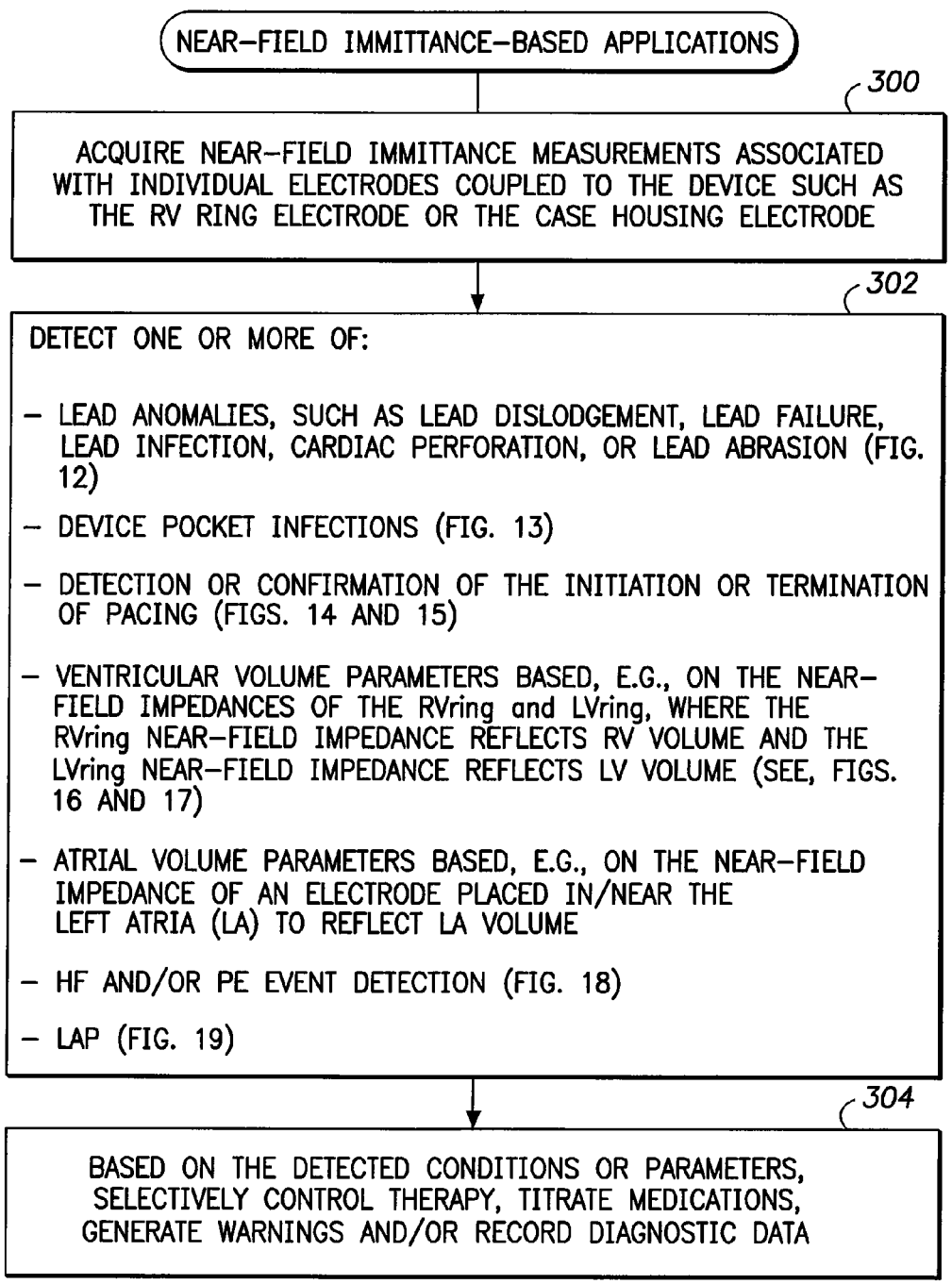
FIG. 11 is flow chart illustrating exemplary applications of the general technique of FIG. 2 wherein near-field impedance measurements associated with particular electrodes are exploited to detect various conditions or parameters, such as to detect lead anomalies or to estimate LAP.
Figure 12:
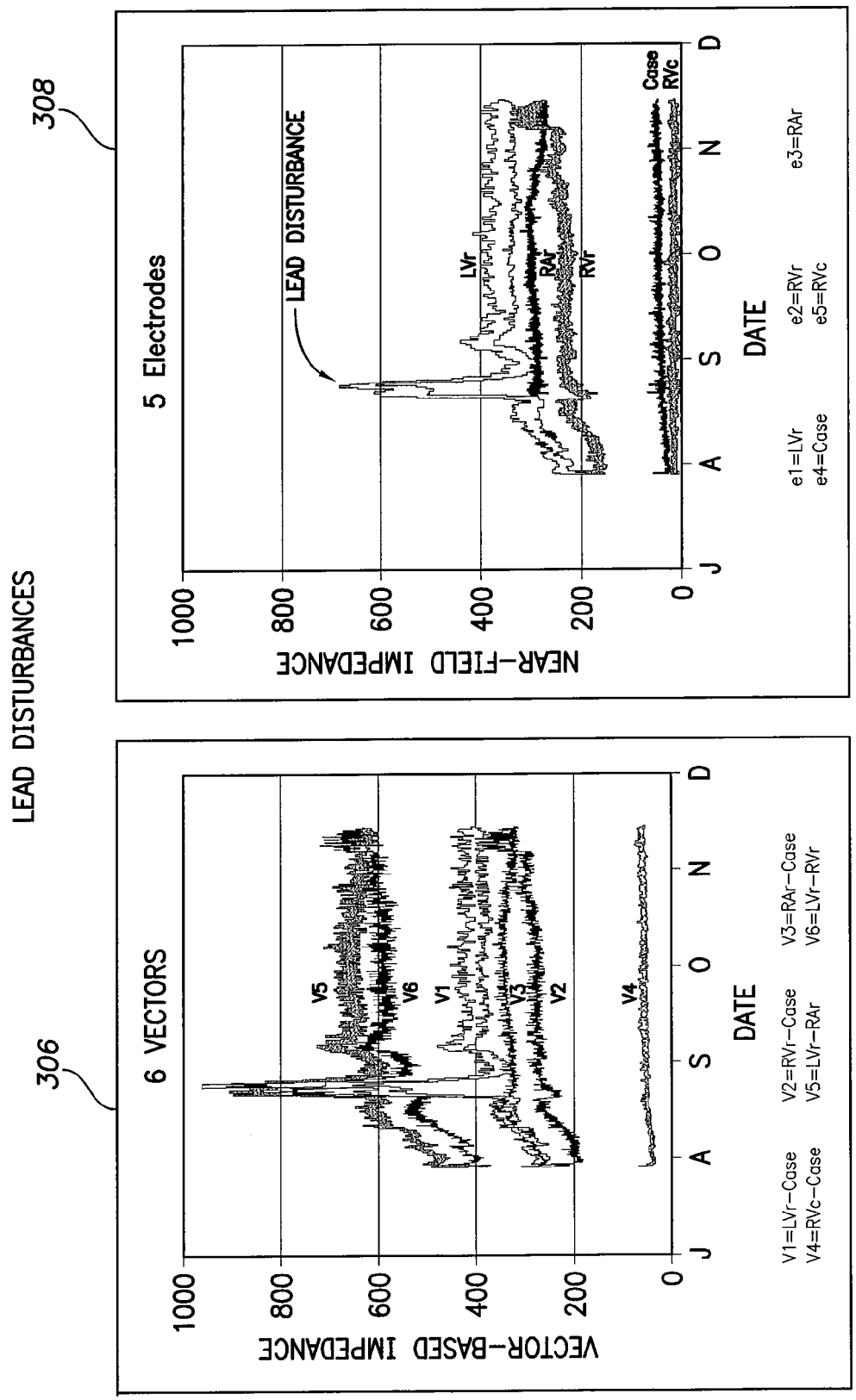
FIG. 12 provides exemplary graphs corresponding to data that can be processed by the procedure of FIG. 11 to detect lead anomalies, which particularly illustrate time-varying changes in various near-field impedance signals representative of a temporary lead disturbance.
Figure 13:
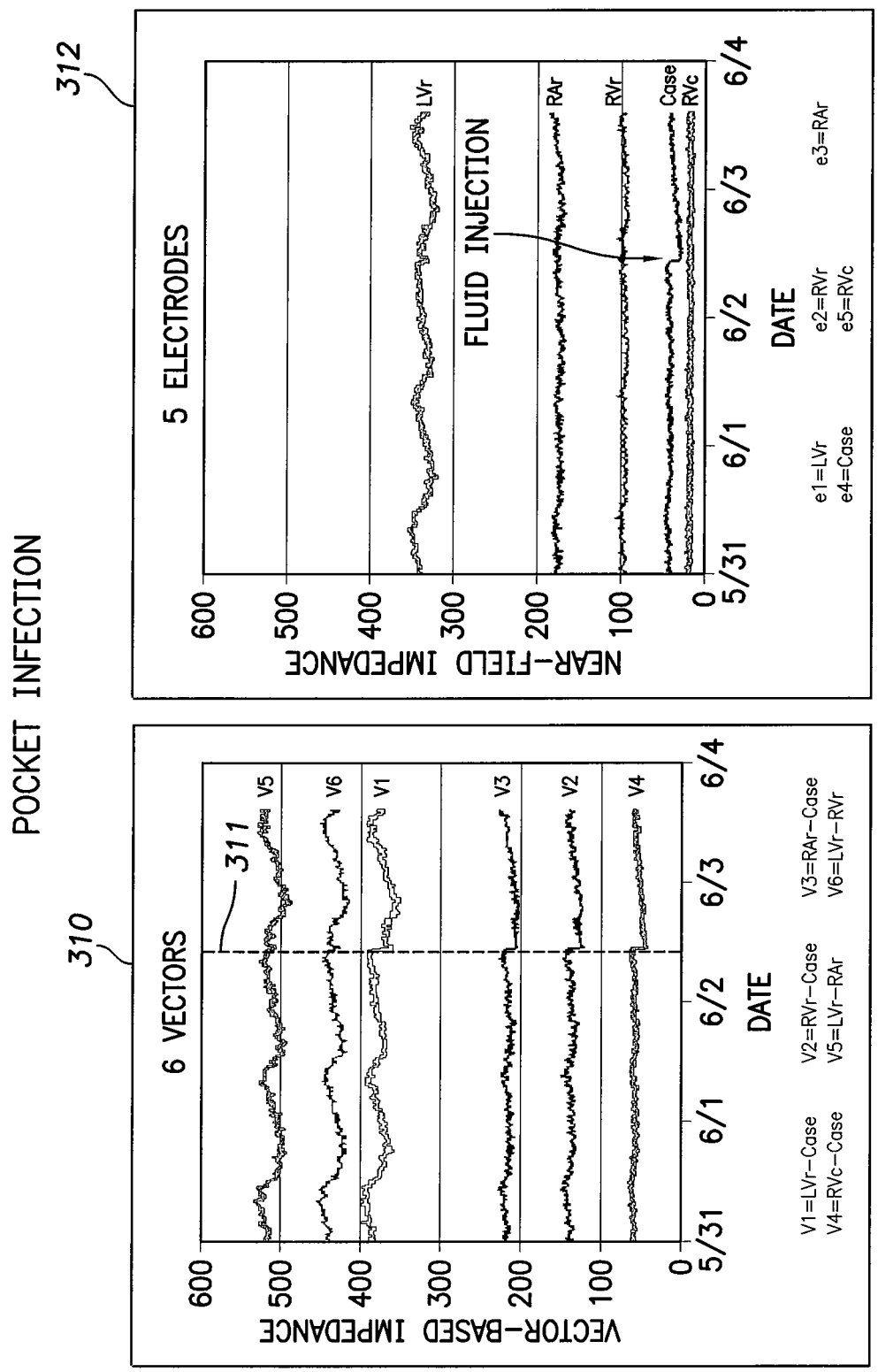
FIG. 13 provides exemplary graphs corresponding to data that can be processed by the procedure of FIG. 11 to detect pocket infections, which particularly illustrate time-varying changes in various near-field impedance signals representative of fluid injection intended to emulate a device pocket infection.
Figure 14:
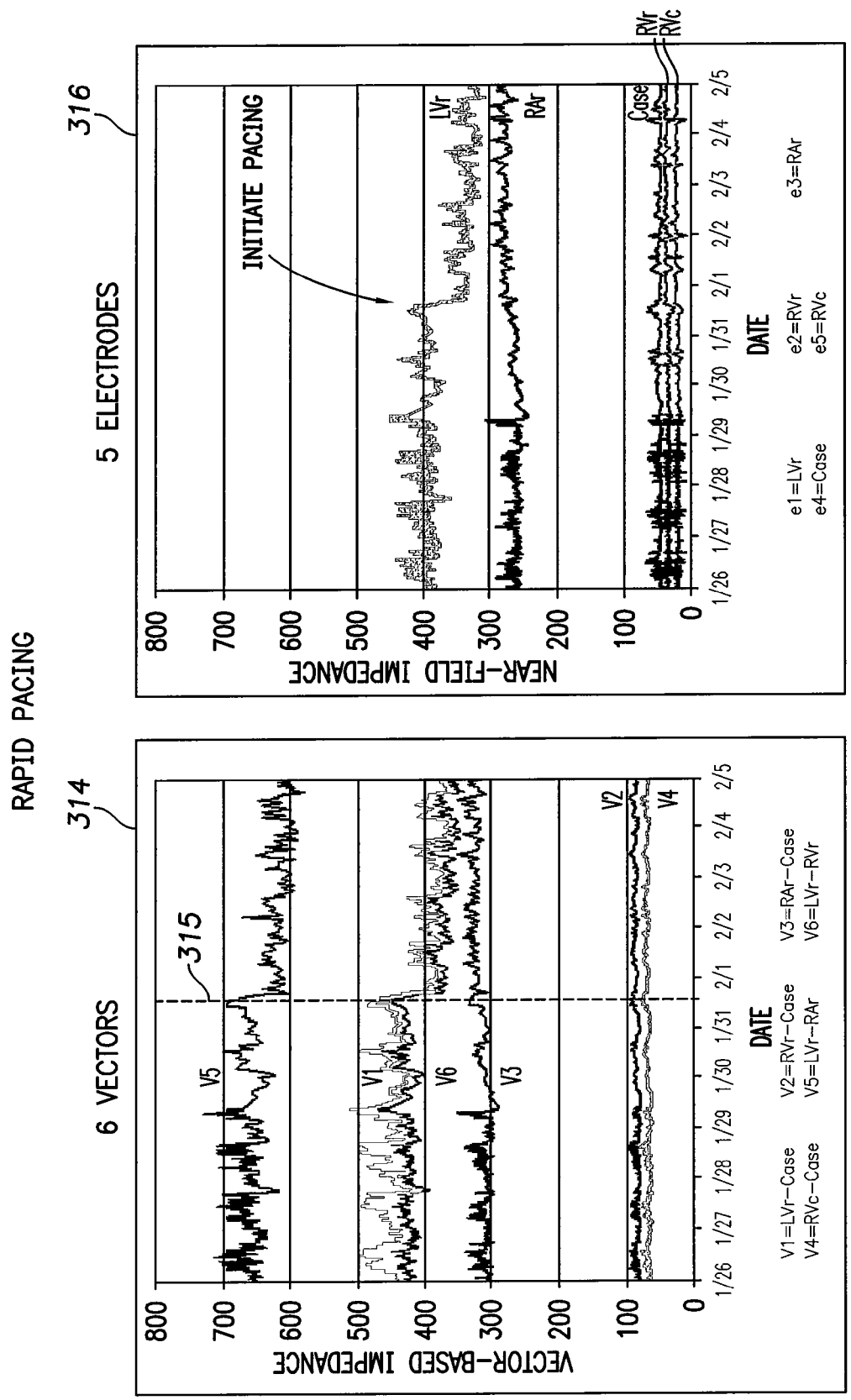
FIG. 14 provides exemplary graphs corresponding to data that can be processed by the procedure of FIG. 11 to confirm the initiation or termination of pacing, which particularly illustrate time-varying changes in various near-field impedance signals representative of the initiation of rapid pacing.
Figure 15:
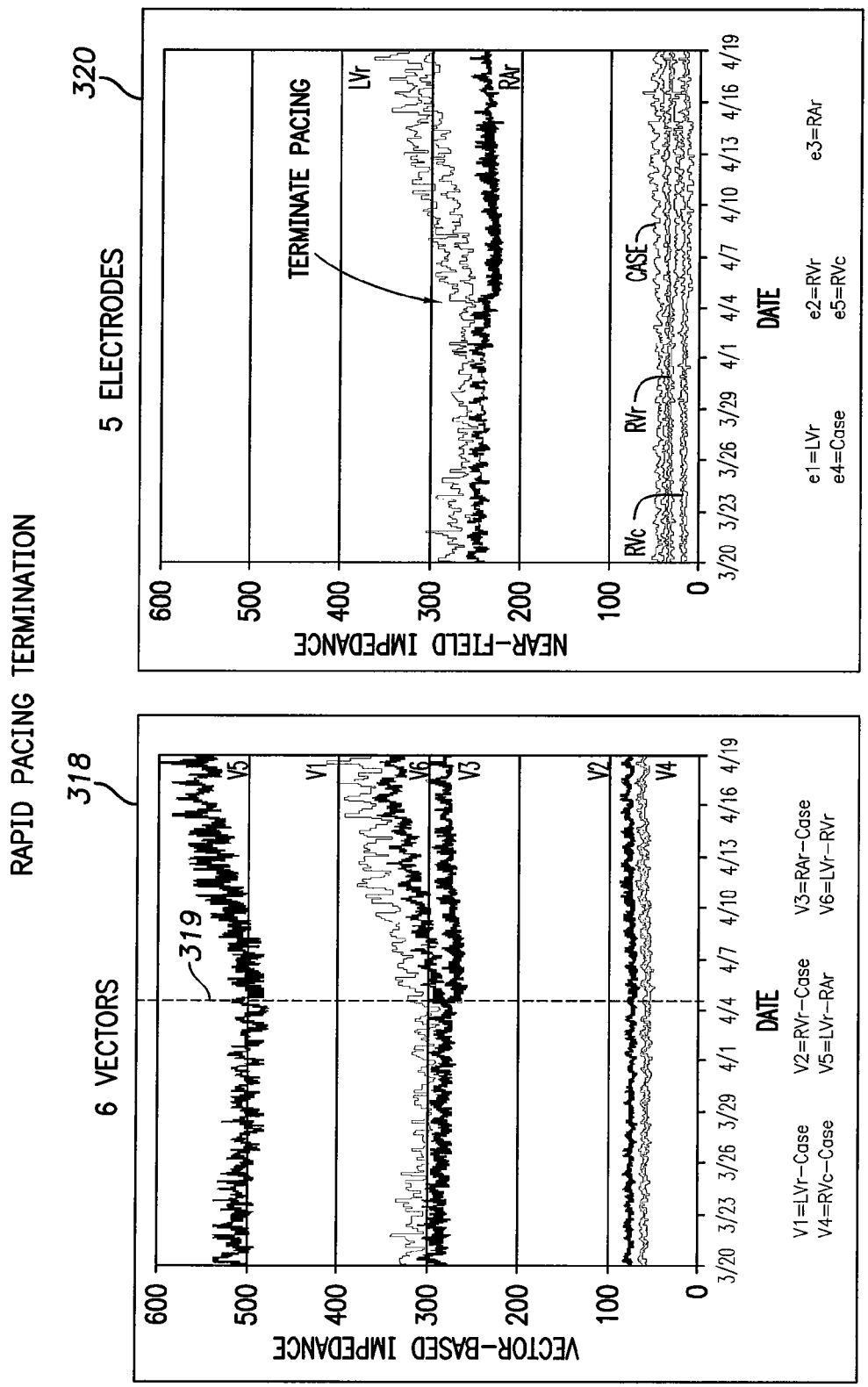
FIG. 15 provides exemplary graphs corresponding to data that can be processed by the procedure of FIG. 11 to detect the initiation or termination of rapid pacing, which particularly illustrate time-varying changes in various near-field impedance signals representative of the termination of rapid pacing.
Figure 16:
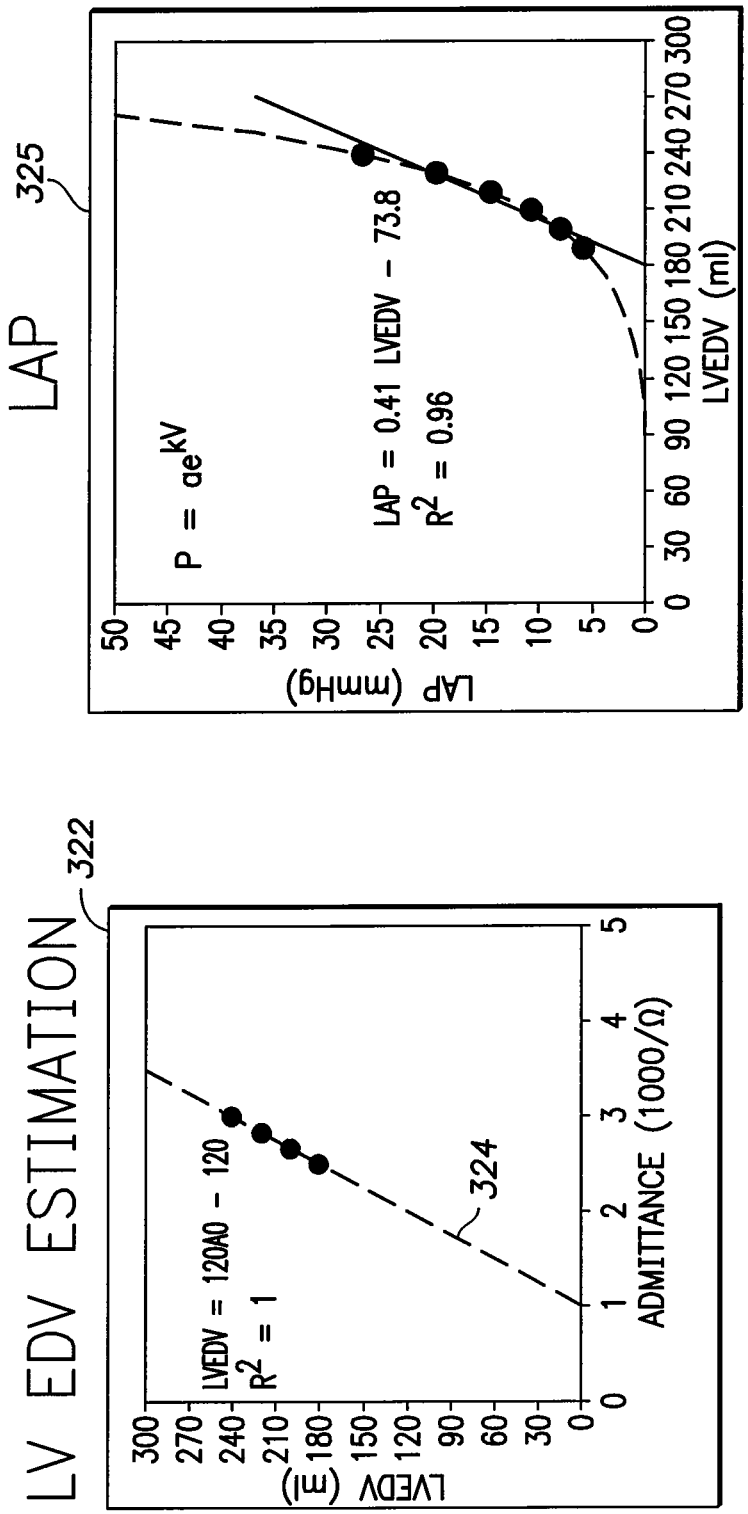
FIG. 16 provides exemplary graphs corresponding to data that can be processed by the procedure of FIG. 11 to detect LV volume, which particularly illustrate a correlation between near-field admittance and LV EDV.
Figure 17:
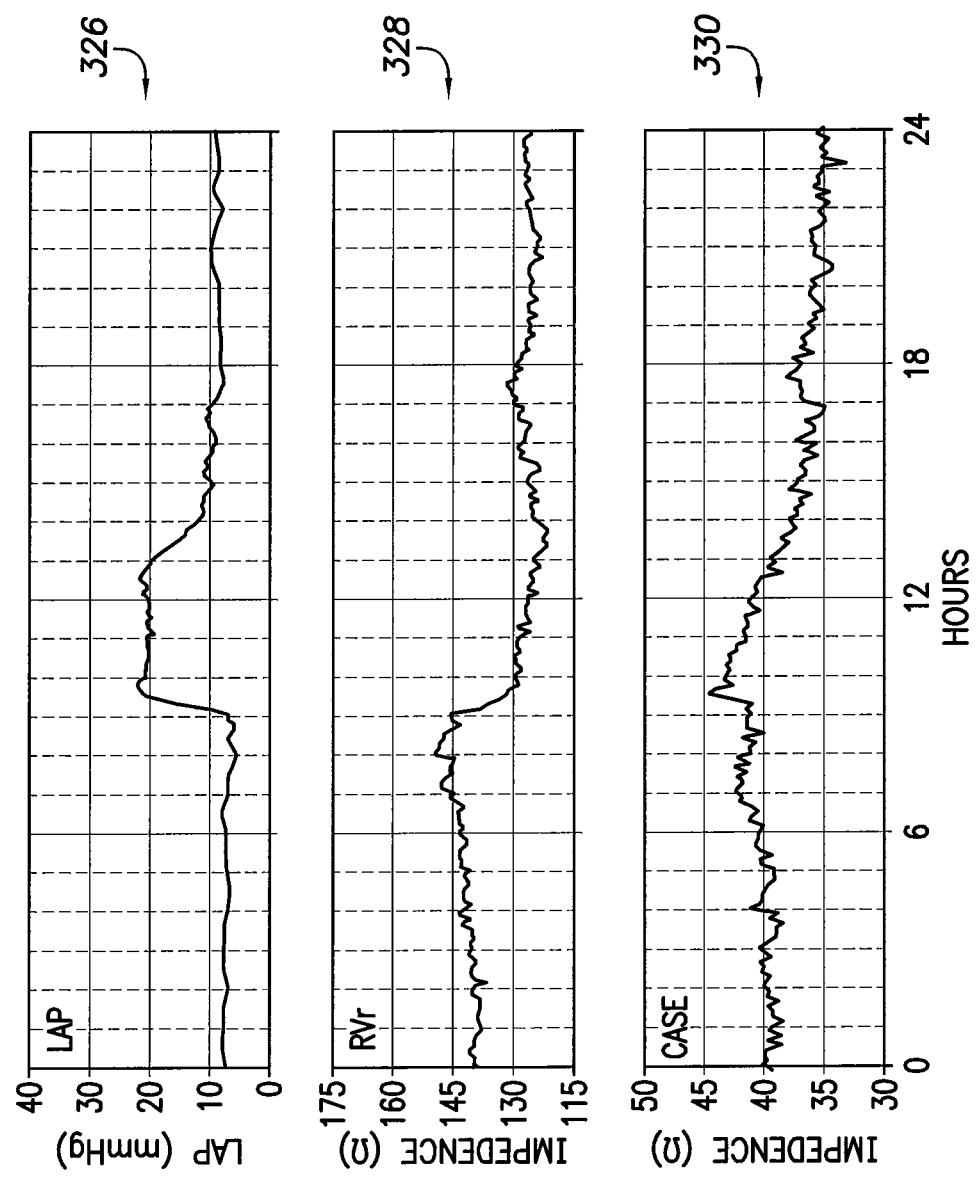
FIG. 17 provides exemplary LAP and impedance graphs corresponding to data that can be processed by the procedure of FIG. 11 to detect changes in fluid volume, which particularly illustrate time-varying changes in various near-field impedance signals representative of an increasing fluid volume status.

FIG. 11 summarizes various applications that exploit near-field impedance or admittance values associated with various electrodes. Beginning at step 300, the pacer/ICD acquires near-field immittance measurements (i.e. near-field impedance or admittance values) associated with individual electrodes coupled to the device, such as the RV ring electrode or the case housing electrode. (These near-field values may be obtained using the techniques of FIGS. 6-8, discussed above.) At step 302, the device then detects one or more of:

lead anomalies, such as lead dislodgement, lead failure, lead infection, cardiac perforation, or lead abrasion (see, FIG. 12);

device pocket infections (see, FIG. 13);

confirmation of the initiation or termination of pacing (see, FIGS. 14 and 15);

Ventricular volume parameters based, e.g., on the near-field impedances of the RVring and the LVring, where the RVring near-field impedance reflects RV volume and the LVring near-field impedance reflects LV volume (see, FIGS. 16 and 17)

Atrial volume parameters based, e.g., on the near-field impedance of an electrode placed in/near the left atria (LA) to reflect LA volume;

HF and/or PE events (see, FIG. 18); and

Figure 19:
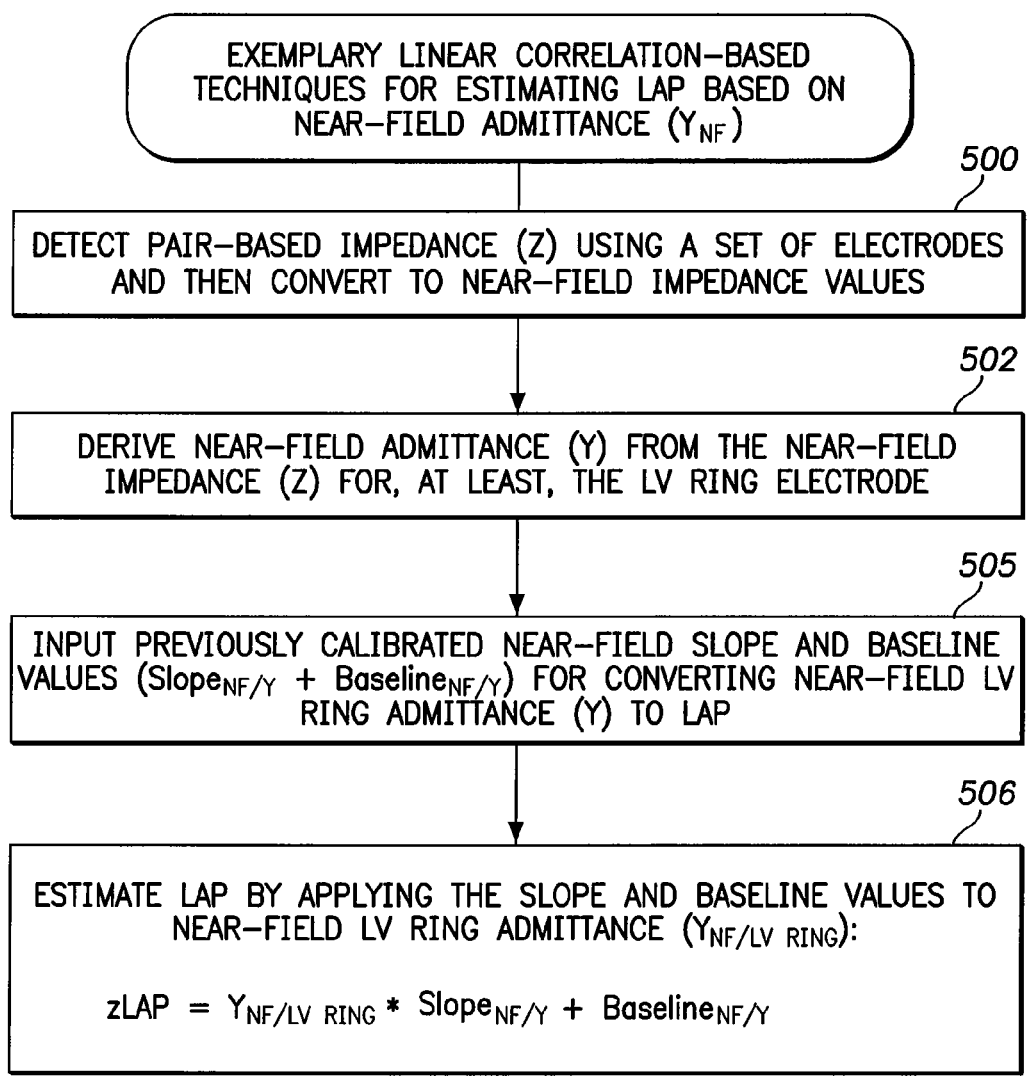
FIG. 19 summarizes an exemplary technique for use with the procedure of FIG. 11 to estimate LAP based on near-field admittance values derived from near-field impedance.

LAP (see, FIG. 19).

At step 304, based on the detected conditions or parameters, the device then selectively controls therapy, titrates medications, generates warnings and/or records diagnostic data. For example, in the case of lead anomalies or pocket infections, warnings are preferably generated to warn the clinician of the problem so that the issue can be addressed.

FIG. 12 provides exemplary time-varying impedance signals during the first several months following implant that illustrate a lead disturbance. More specifically, a first graph 306 illustrates vector-based impedance signals derived from a canine test subject wherein a disturbance in the LV lead has been introduced. A second graph 308 illustrates near-field impedance values associated with the individual electrodes. As can be seen, when examining the near-field impedances of graph 308, it is immediately clear that the disturbance is within the LV lead; whereas when examining the vector-based impedances of graph 306, the source of the disturbance is not easily ascertained. That is, when attempting to detect and isolate lead disturbances using vector-based impedance vectors, the particular lead is not readily identified because the disturbance may affect more than one vector depending on how many vectors utilize the same electrode or the same lead. The near-field immittance measurements derived for each electrode are useful for detecting other lead anomalies, which include but not limited to lead dislodgement, lead failure (e.g., lead fracture), lead infection, lead abrasion, and/or lead perforation. This application of the near-field model is particularly useful in the event multiple anomalies and/or disturbances are occurring at more than one electrode simultaneously such that the interpretation of the vector-based impedance signals becomes too difficult to interpret.

FIG. 13 provides exemplary time-varying impedance signals that illustrate affects caused by a pocket infection emulated via the injection of fluids into the tissue pocket surrounding an implanted device of an animal test subject. A first graph 310 illustrates vector-based impedance signals derived over a several day interval from an ovine test subject in which liquid was injected into the device pocket at time 311 to emulate a pocket infection. A second graph 312 illustrates near-field impedance values associated with the individual electrodes, including a case electrode near-field impedance trace 313. When examining the near-field impedances of graph 312, particularly trace 313, it is immediately clear that there is sudden drop in impedance near the device housing (case) electrode indicative of a possible pocket infection of the type where fluids containing inflammatory and white blood cells surround the device in response to the infection. However, when examining the vector-based impedances of graph 310, the source of the disturbance in impedance is not easily ascertained as it affects several of the traces. It is noted that the fluid was subsequently reabsorbed over the next twenty-four hour period following its introduction, causing the near-field impedance of the device case to return to its prior baseline level.

FIG. 14 provides exemplary time-varying impedance signals that illustrate impedance affects occurring due to the initiation of rapid ventricular pacing within a canine test subject. More specifically, a first graph 314 illustrates vector-based impedance signals derived from a canine test subject over a period of ten days in which rapid pacing was initiated at time 315. Such pacing has the effect of acutely increasing LAP, which causes a corresponding decrease in various vector-based impedance values as shown (and which may be due, in part, to a sudden increase in LV volume.) A second graph 316 illustrates near-field impedance values associated with the individual electrodes, including an LV electrode near-field impedance trace 317. When examining the near-field impedances of graph 316, particularly trace 317, it is immediately clear that there is sudden drop in impedance in or near the LV; whereas when examining the vector-based impedances of graph 314, the source of the disturbance in impedance is not easily ascertained.

Following a prolonged period of rapid ventricular pacing (four to eight weeks) in the canine test subject, a gradual increase in LV volume is expected that coincides with an increase in LAP. Upon cessation in rapid ventricular pacing, an acute decrease in LAP is expected to occur as a result of the elimination of cannon A-waves. However, a corresponding slower change (i.e. a lag) in the impedance associated with the LV ring electrode occurs as the LV volume returns over the subsequent weeks toward baseline. This produces a hysteresis-like behavior between LAP and LV volume. This hysteresis behavior is described more fully in co-pending U.S. patent application Ser. No. 12/853,157, cited above.

FIG. 15 illustrates the changes in impedance over a period of ten days occurring within the canine test subject following cessation of rapid pacing by way of vector-based impedance graph 318 and near-field impedance graph 320. Rapid pacing was terminated at time 319 and subsequent increases in impedance are then observed in several of the pair-based impedance traces of graph 318, but most significantly in the LV trace of the near-field impedances.

Thus, FIGS. 14-15 show that the initiation and termination of rapid ventricular pacing that are associated with acute physiologic changes in pressure and intra-cardiac volume can be readily detected and identified within near-field impedances.

FIG. 16 illustrates in graphical form the relationships between LV EDV and the near-field admittance of the LV ring electrode and LV EDV and LAP. A first graph 322 shows a linear relationship 324 between near-field admittance of the LV ring electrode and LV EDV. Based on this relationship, the device converts near-field LV ring admittance values obtained by the device into LV EDV values. In this regard, by decomposing vector-based impedance vector measurements into near-field values, an indication of LV volume may be obtained using the ring electrode of the LV lead. In one example, a non-invasive echocardiogram study with simultaneous acquisition of impedance signals is used to determine LV EDV and LV ESV values for the patient along with the corresponding impedance measurements. Impedance signals are acquired at a high sampling rate (e.g., 128 Hz) along three lead configuration vectors that form an impedance triangle (e.g., LVring-Case, RVring-LVring, and RVring-Case) in combination with an intra-cardiac electrogram signal. The near-field impedance signal associated with the LV ring electrode is derived and used to determine the minimum and maximum near-field impedance measurements for the LV ring electrode within each cardiac cycle, which are then averaged over multiple cardiac cycles to yield a representative maximum and minimum impedance measurement (Zmin and Zmax). Zmin and Zmax are then converted to corresponding near-field admittance measurements (Ymax and Ymin) that are calibrated to match the LV volume measurements for the patient obtained via the echocardiogram. The near-field impedance associated with the LVring electrode is then used by the implanted device to estimate LV volumes (zVolume) for the patient.

A second graph 325 shows a relationship 327 between LAP and LV EDV that can be characterized using an exponential formula, a polynomial formula or other transformational model or formula. Based on this relationship, the device converts the estimated LV EDV values into LAP values. Estimates of LV EDP or LAP can then be derived. The RV volume can similarly be derived by correlating the near-field RVring admittance with RV EDV and RV ESV.

FIG. 16 includes a graph 325 and equations relating LV EDV to LAP. The relationship between LV EDV and LAP may be non-linear (e.g., exponential), but for practical purposes be modeled with a linear equation over a narrow range of filling volumes and pressures. The relationship between LV EDV and LAP may be determined for each patient individually with use of an echocardiogram to assess LV EDV and the use of a pulmonary capillary wedge pressure measurement obtained using a pulmonary artery catheter to assess LAP. An estimate of LAP based on impedance (zLAP) may subsequently be derived by transforming the previously derived zVolume estimate obtained from the near-field impedance associated with the LV ring electrode into a corresponding LAP estimate. Impedance-based LAP estimation is generally referred to herein as "zLAP." Prior zLAP techniques are discussed in U.S. patent application Ser. No. 11/559,235, filed Nov. 13, 2006, entitled "System and Method for Estimating Cardiac Pressure Using Parameters Derived from Impedance Signals Detected by an Implantable Medical Device", as well as in at least some of the following applications: U.S. Provisional Patent Application Ser. No. 60/787,884, filed Mar. 31, 2006, entitled "Tissue Characterization Using Intracardiac Impedances with an Implantable Lead System." See, also, U.S. patent application Ser. No. 11/558,101, filed Nov. 9, 2006; Ser. No. 11/557,851, filed Nov. 8, 2006; Ser. No. 11/557,870, filed Nov. 8, 2006; Ser. No. 11/557,882, filed Nov. 8, 2006; and Ser. No. 11/558,088, filed Nov. 9, 2006; each entitled "Systems and Methods to Monitor and Treat Heart Failure Conditions." These applications are incorporated by reference herein, particularly with regard to their descriptions of zLAP.

Insofar as the choice of the LVring electrode, the LVring near-field impedance is believed to provide the best correlation with LAP and with LV EDV, particularly in the absence of a significant degree of mitral valve regurgitation and when the LVring electrode is adherent to the pericardial sac, such that changes in posture produce minimal to no change in tissue contact with the pericardial sac. It should be noted, however, that the RVring near-field impedance may also provide a good correlation with LAP, by way of correlating with the RV EDV which indirectly correlates with LAP in a majority of patients, particularly those in whom there is absence of RV dysfunction, pulmonary hypertension, and/or absence of a high pressure gradient across the pulmonary vascular bed. As previously outlined, the near-field impedance associated with the LVring electrode reflects the impedance associated with the bare electrode in combination with the impedance associated with the electrode-tissue interface and the nearby surrounding tissue and fluid within a short distance (~1-2 cm), which include the scar tissue surrounding the LVring electrode within the coronary vein, the adjacent epicardial and myocardial tissues, the adjacent pericardium, the adjacent lung tissue if in close proximity, and any fluids or blood within this near-field region. The measured near-field impedance associated with the LVring electrode will vary throughout the cardiac and respiratory cycles and also in response to changes in posture. Cardiac contraction, respiration and changes in posture all influence the degree of electrode-tissue contact and the amount of fluid and blood within the near-field surrounding the electrode. During systole myocardial contraction causes myocardial wall thickening with an increase in the overlap of actin and myosin filaments in combination with a corresponding reduction in blood content within the myocardial wall as the blood within the coronary veins and the LV cavity is being squeezed out. Contraction of the myocardium during systole causes a corresponding increase in the electrode-tissue contact along with a simultaneous decrease in fluid/blood content within the near-field region surrounding the LVring electrode, both of which result in a proportional increase in the measured near-field impedance. The more LV EDV decreases the more the LVring near-field impedance increases, such that changes in the near-field impedance correlate inversely with changes in the LV EDV.

Similarly, during diastole myocardial relaxation causes myocardial wall to thin with a decrease in the overlap of actin and myosin filaments in combination with a corresponding increase in blood content within the myocardial wall as the blood within the coronary veins and LV cavity is being filled. Relaxation of the myocardium during diastole causes a corresponding decrease in the electrode-tissue contact along with a simultaneous increase in fluid/blood content within the near-field region surrounding the LVring electrode, both of which result in a proportional decrease in the measured near-field impedance. Thus, at least in an indirect way, the near-field admittance for the LVring electrode reflects and correlates with LV volume, such that an inverse relationship exists between the near-field impedance associated with the LVring electrode and LV EDV. Since LV EDV correlates with LAP, LVring near-field impedance thereby also correlates with LAP.

Additional factors such as (1) local edema within the myocardial wall in response to tissue injury following device implant; (2) leakage of fluids from the local vascular beds within the myocardial wall following a sustained period of elevated hydrostatic pressure (myocardial wall edema); and/or (3) a change in the adjacent extra-vascular fluid volume within the surrounding pericardial and pleural spaces may impact the LVring electrode near-field impedance measurements. When changes in the LVring electrode near-field impedance are a consequence of a change in the surrounding fluid volume which are unrelated to changes in the intravascular fluid volume (e.g., tissue injury secondary to device implant) or are indirectly linked to changes in the intravascular fluid volume (e.g., myocardial wall edema or an increase in pericardial/pleural fluid secondary to HF), the correlation between the LVring near-field impedance and the intra-cardiac blood volume (LV EDV) and pressure (LV EDP or LAP) may be reduced. Data has shown that following a HF exacerbation the recovery in the LVring near-field impedance back to baseline may have a lag relative to the observed symptomatic recovery of the patient. The observed lag in the recovery of the LVring near-field impedance may be a consequence of a longer time interval required for local edema within the myocardial wall to resolve, in combination with a longer time interval required for the surrounding pericardial and/or pleural fluid to reabsorb and return back to baseline levels. This delay in recovery of the LVring near-field impedance may be leveraged to determine a suitable time interval for continuing close patient follow-up with intensive medical therapy in the period immediately following discharge of the patient from the hospital. It is not uncommon for patients to be re-admitted soon after being discharged from the hospital, which may be a consequence of reducing the intensity of the medical therapy pre-maturely following hospital discharge. Thus, the near-field impedance for the LVring electrode may be helpful in monitoring the recovery of not only the LV volume, but also the recovery of the LV myocardium and surrounding extra-vascular fluid.

Although the LVring is preferred, an electrode placed within or very close to the left atrium (e.g., within the coronary sinus) may alternatively be used to correlate with Left Atrial (LA) volume and LAP. Still further, note that the RVring near-field impedance has an inverse correlation with RV volume. Beat-to-beat variations between min and max near-field impedance correlate inversely with RV EDV and RV ESV, allowing RV EDV and RV ESV to be estimated based on near-field RVring values. In comparison to the LVring electrode, the RVring electrode has the benefit of being located within the intravascular space, such that the effects of myocardial wall edema, pericardial sac tissue contact, and/or pericardial/pleural fluid volume change have reduced impact on the measured RVring near-field impedance.

FIG. 17 provides a set of graphs of the LAP and near-field impedance associated with the RVring (or RVr) and Case electrodes derived from an ovine study during an acute volume loading experiment. The top graph 326 shows the measured LAP recorded over a time interval of twenty-four hours. Nine hours into the recording, four liters of a colloid solution was administered intravenously over a period of four hours (infusion rate of 1 Liter/hour). In response to acute fluid loading, the LAP increases from a baseline of about 8 mmHg to a peak of 20 mmHg over the first hour. Over the same time course, the administered fluid produces an acute decrease in the near-field impedance of the RVring electrode from 145 to 130 ohms, as shown by way of graph 328. During the next three hours, LAP remains stable at 20 mmHg, while the RVring electrode continues to decrease slightly from 130 to 125 ohms. In contrast to the near-field impedance associated with the RVring electrode, the near-field impedance associated with the Case electrode has a slower time course of response, as shown by way of graph 330. The near-field impedance associated with the case electrode decreases from a peak of 45 ohms to a minimum of 35 ohms over a period of 8 hours. The data also shows differences in the rate of recovery once the fluids are no longer administered. LAP recovers within an hour to a new baseline of 10 mmHg, while the recovery in the near-field impedances for both the RVring and Case electrodes is more subtle and over a longer duration. This difference may be a consequence of impedance reflecting more so a fluid volume rather than a pressure.

Based on the example shown in FIG. 17, it should be noted that the accumulation of fluid around the RVring electrode versus the device Case electrode has different time constants associated with the response to the acute increase in intravascular fluid volume. The acute increase in the intravascular fluid volume produced a fast increase in RV volume, which produced a corresponding fast change in the near-field impedance associated with the RVring electrode. For this substantial increase in intravascular fluid volume, a subsequent increase was produced in the interstitial fluid volume within the subcutaneous device pocket. The increase in the interstitial fluid volume within the device pocket produced a decrease in the near-field impedance associated with the Case electrode. However, as illustrated in this example because the change in the interstitial fluid volume within the device pocket occurred more slowly relative to the change in the RV volume, the change in the near-field impedance for the Case electrode occurred slower than change seen for the near-field impedance for the RVring electrode. This relative delay in the response time to a change in fluid volume makes the device Case electrode a less favorable electrode for monitoring intravascular fluid volume in comparison to the RVring electrode.

Figure 18:
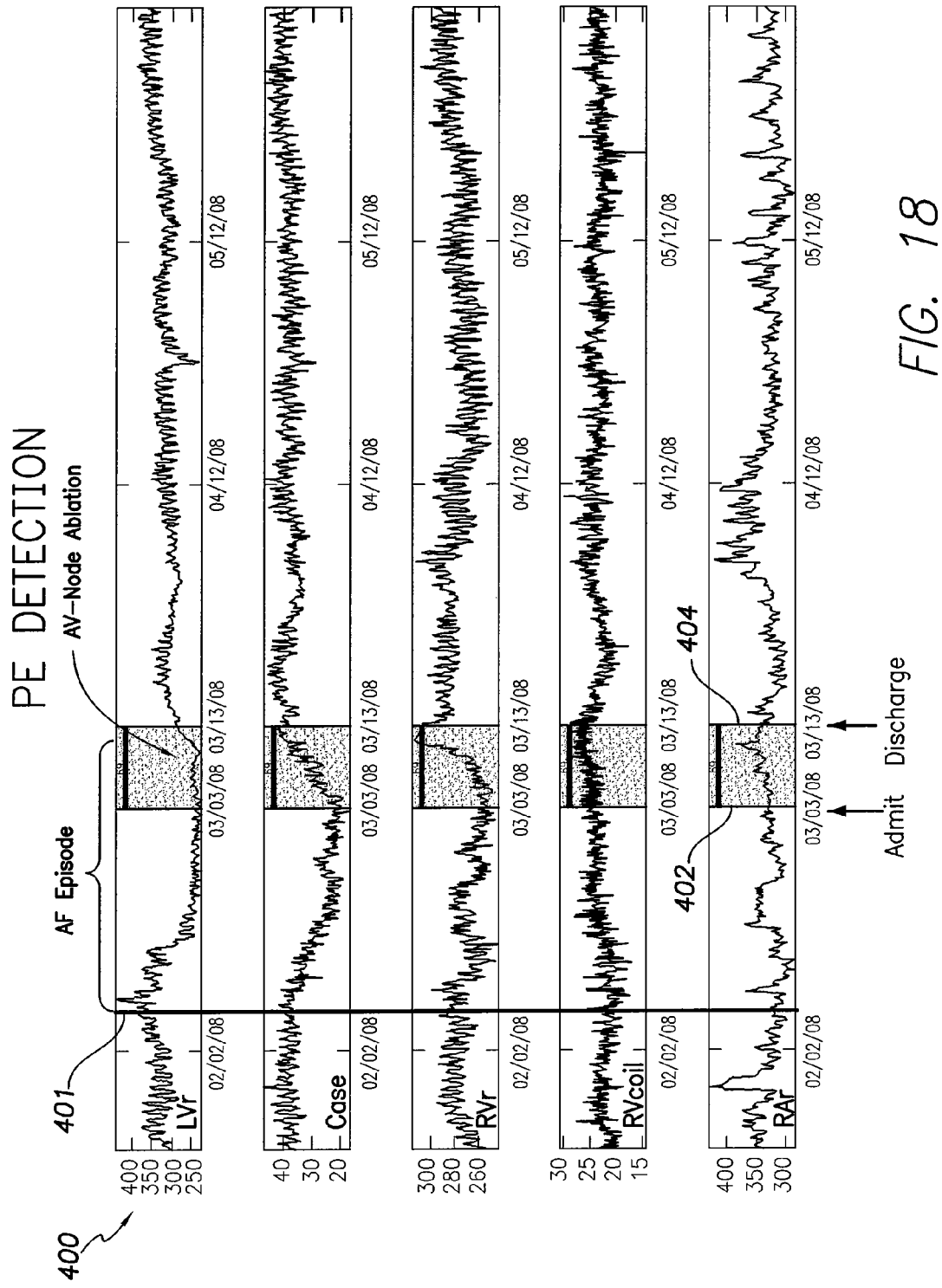
FIG. 18 provides exemplary impedance graphs corresponding to data that can be processed by the procedure of FIG. 11 to detect PE, which particularly illustrate time-varying changes in various near-field impedance signals representative of a PE event.

FIG. 18 provides a set of graphs 400 of near-field impedance traces for the various electrodes from a patient that developed an acute episode of atrial fibrillation (AF) at time 401 that was sustained for several weeks and ultimately led to the development of worsening HF requiring hospitalization secondary to an episode of PE. During the hospitalization, which extended from time 402 to time 404 the patient was treated with intravenous diuretics in combination with an AV-node ablation procedure. The trend data demonstrate variations in the recovery pattern of the near-field impedance signals across the various electrodes in response to the in-hospital diuretic therapy administered. The trend data demonstrate that the RVr electrode has the fastest in-hospital recovery with a slight overshoot, while the LVr electrode has a slower course of recovery extending into the outpatient setting. In comparison, the Case electrode which reflects the interstitial fluid within the device pocket had a recovery pattern that was somewhat slower that for the RVr electrode, but faster than the recovery pattern for the LVr electrode. The much slower recovery pattern for the LVr electrode may be a consequence of the LV myocardial wall edema recovering more slowly than the edema within the device pocket. The RAr and RVcoil (Coil) electrodes do not clearly show consistently declining trends in the near-field impedance measurements in the time period prior to hospitalization, but do show a slight increasing trend in near-field impedance during the hospitalization when intravenous diuretic therapy was being administered. It should also be noted that the near-field impedance associated with the LVring exhibits a marked decrease in value well before the PE event.

Exemplary Near-Field Admittance-Based zLAP Estimation Technique

Turning now to FIG. 19, for the sake of completeness, a technique for calculating zLAP in response to near-field admittance values derived from signals initially detected based on vector-based impedance detection pulses will be described. This particular technique employs linear correlation using near-field admittance values but other correlation techniques can be used as well to calculate zLAP. At step 500, the pacer/ICD detects vector-based electrical impedance (Z) values along various sensing vectors and then converts the vector-based impedance values to near-field impedance values using the techniques discussed above. For example, the aforementioned six impedance vectors can be used to yield near-field impedance values for each of five individual electrodes.

At step 502, the pacer/ICD derives near-field admittance (Y) from the near-field electrical impedance values to obtain, at least, the near-field admittance for the LVring electrode. At step 505, the pacer/ICD inputs predetermined conversion factors from memory for converting near-field LVring admittance values to LAP. The conversion factors may be, e.g., predetermined slope and baseline values obtained during a calibration procedure employing linear regression and exploiting various physiologic maneuvers (e.g., Posture Maneuvers.) See, FIGS. 29-35 discussed below. Note that these near-field conversion factors will generally differ from vector-based conversion factors discussed in the prior applications (cited above) that were used to estimate LAP from vector-based impedance or admittance values.

At step 506, the pacer/ICD then estimates LAP within the patient by applying the conversion factors retrieved from memory (at step 505) to the near-field LVring admittance (obtained at step 502). When using slope and baseline conversion factors, LAP may be generally estimated by using:

$$zLAP = Y_{NF/LV\,RING} * Slope_{NF/Y} + Baseline_{NF/Y}$$

wherein the subscript NF is employed to designate that the relevant values are near-field values.

The formulae assume a linear relationship between LAP and the $Y_{NF/LV\,RING}$, which is an appropriate presumption, at least insofar as estimating LAP is concerned. Routine experimentation may be performed to determine whether a linear relationship is also suitable for use in estimating other particular cardiac pressure values, such as LV pressure, from near-field admittance values associated with other electrodes. Moreover, it should be understood that linear models need not necessarily be used, i.e. more sophisticated correlation models may instead be employed. Linear models are preferred due to their simplicity.

As noted above, LAP is useful in detecting episodes of HF or cardiogenic PE. Reliable estimates of LAP also allow the dosing of heart failure medications (such as diuretics) to be properly titrated so as to minimize the number of episodes of acute heart failure decompensation. That is, accurate LAP monitoring provides for early identification of incipient HF decompensation and guides the adjustment of vasodilator and diuretic dosing.

Steps 500-506 may be repeated in a loop so as to update the estimated LAP. Estimates may be performed substantially in real-time so as to permit the pacer/ICD to continuously, or at least very frequently, calculate new LAP values. That is, in some implementations, a real-time LAP(t) function may be estimated based on near-field values so as to allow the pacer/ICD to track beat-to-beat changes in LAP. In particular, estimates of LAP based on near-field admittance may potentially be performed substantially in real-time based on near-field signals, assuming the pacer/ICD is appropriately configured. This allows the pacer/ICD to respond promptly to changes within the heart of the patient to detect conditions such as HF and cardiogenic PE. Appropriate therapy may then be delivered.

Note that the cardiac pressure value estimated using the techniques described herein is an effective intracardiac pressure ($P_{eff}$) not an absolute pressure. It represents the absolute intracardiac pressure less intrathoracic pressure:

$$P_{eff} = P_{intracardiac} - P_{intrathoracic}$$

That is, the effective pressure is a type of gauge pressure. Unless otherwise noted, all estimated cardiac pressure values discussed herein, particularly estimated LAP, are effective pressure values. In some examples described herein, the term "effective LAP" may be used as a reminder that effective pressures are used. In any case, effective pressure values are typically more useful from a clinical perspective than absolute pressure values.

In some implementations, different sets of conversion factors are stored within the pacer/ICD for use in converting the admittance values into LAP values depending on whether the patient is presently suffering an episode of acute mitral valve regurgitation (MR.) See, for example, the application cited above entitled "Systems and Methods for Estimating Left Atrial Pressure (LAP) in Patients with Acute Mitral Valve Regurgitation for use by an Implantable Medical Device." Still further, in some implementations, the device selectively suspends/cancels the LAP estimation procedure based on an assessment of the reliability of the LAP estimate made based on an analysis of various cardioelectric and cardiomechanical parameters. See U.S. patent application Ser. No. 12/109,304, filed Apr. 25, 2008, of Guffinger et al., entitled "System and Method for Calibrating Cardiac Pressure Measurements Derived from Signals Detected by an Implantable Medical Device", now U.S. Pub. Application No. 20080262361A1.

In addition, in some implementations posture off-sets to the measured impedance signals may be applied in order to compensate for acute changes tissue contact (e.g., pericardial sac tissue contact) that occur secondary to changes in posture independent of changes in fluid volume and/or pressure. See U.S. patent application Ser. No. 12/712,003, filed Feb. 24, 2010, of Guffinger, entitled "Device and Method for Adjusting Impedance Measurements Based on Posture of Patient".

Thus, the use of near-field impedance facilitates estimates of LAP based on impedance/admittance. Note that, in implementations where therapy is automatically delivered in response to an elevated LAP or due to detecting of HF or cardiogenic PE, the pacer/ICD might be equipped to employ at least one other detection technique to corroborate the detection of the medical condition before therapy is delivered. Techniques for detecting or tracking heart failure are set forth in the following patents and patent applications: U.S. Pat. No. 6,328,699 to Eigler et al., entitled "Permanently Implantable System and Method for Detecting, Diagnosing and Treating Congestive Heart Failure"; U.S. Pat. No. 6,970,742 to Mann et al., entitled "Method for Detecting, Diagnosing, and Treating Cardiovascular Disease"; U.S. Pat. No. 7,115,095 to Eigler et al., entitled "Systems and Methods for Detecting, Diagnosing and Treating Congestive Heart Failure"; U.S. patent application Ser. No. 11/100,008, of Kil et al., filed Apr. 5, 2005, entitled "System and Method for Detecting Heart Failure and Pulmonary Edema based on Ventricular End-Diastolic Pressure using an Implantable Medical Device", now U.S. Pat. No. 7,437,192; U.S. patent application Ser. No. 11/014,276, filed Dec. 15, 2004, of Min et al., entitled "System and Method for Predicting Heart Failure based on Ventricular End-Diastolic Volume/Pressure using an Implantable Medical Device," now U.S. Pat. No. 7,272,443; U.S. patent application Ser. No. 10/810,437, filed Mar. 26, 2004, of Bornzin et al., entitled "System and Method for Evaluating Heart Failure Based on Ventricular End-Diastolic Volume Using an Implantable Medical Device," now U.S. Pat. No. 7,505,814; and U.S. patent application Ser. No. 10/346,809, filed Jan. 17, 2003, of Min et al., entitled "System and Method for Monitoring Cardiac Function via Cardiac Sounds Using an Implantable Cardiac Stimulation Device," now U.S. Pat. No. 7,139,609. See also: U.S. Pat. No. 6,572,557, to Tcou et al.; U.S. Pat. No. 6,645,153, to Kroll et al., entitled "System and Method for Evaluating Risk of Mortality Due To Congestive Heart Failure Using Physiologic Sensors"; and U.S. Pat. No. 6,438,408 to Mulligan et al., entitled "Implantable Medical Device for Monitoring Congestive Heart Failure."

Although primarily described with respect to examples having a pacer/ICD, other implantable medical devices may be equipped to exploit the techniques described herein. For the sake of completeness, an exemplary pacer/ICD will now be described, which includes components for performing or controlling the various functions and steps already described.

Exemplary Pacer/ICD

Figure 21:
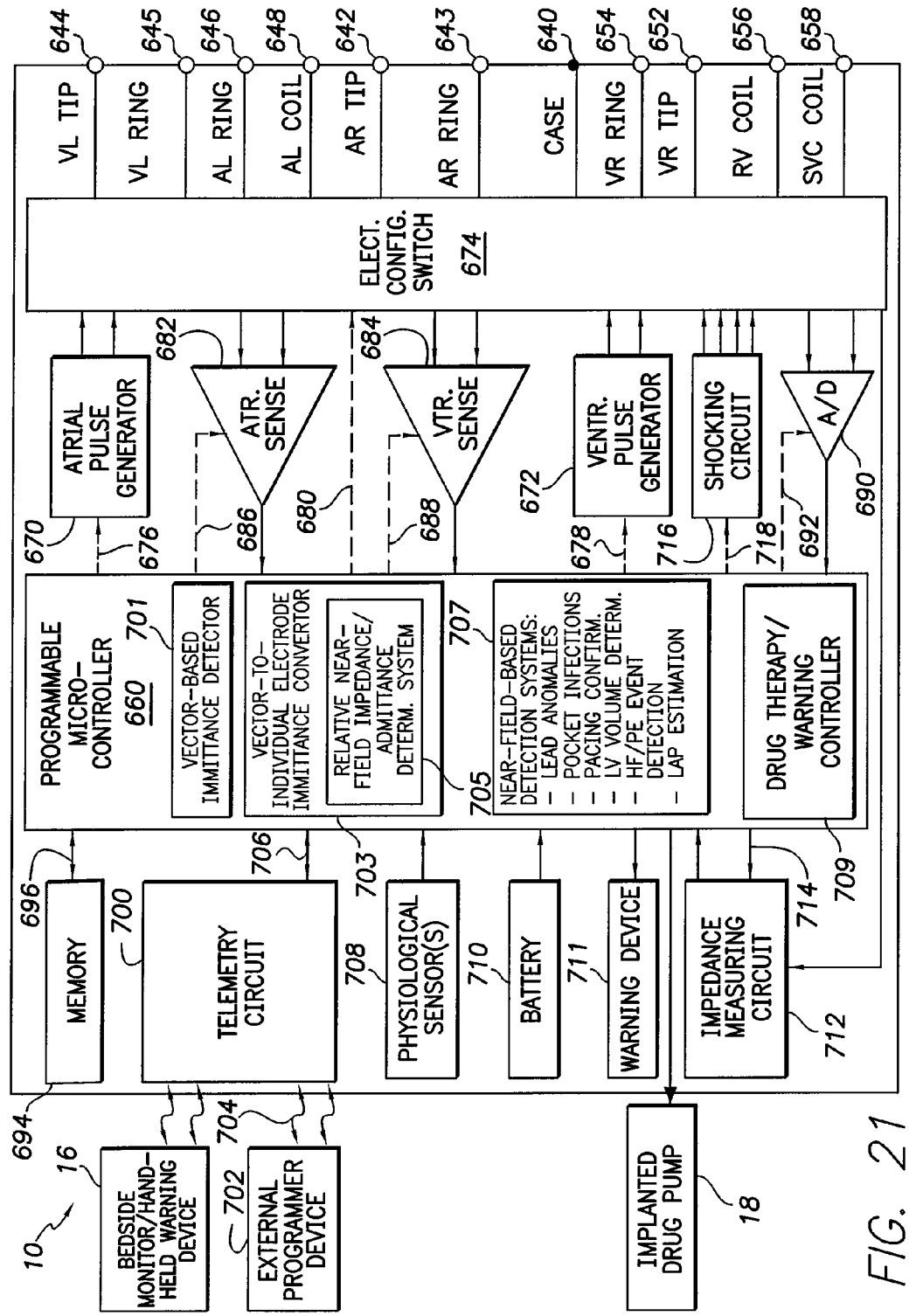
FIG. 21 is a functional block diagram of the pacer/ICD of FIG. 20, illustrating basic circuit elements that provide cardioversion, defibrillation and/or pacing stimulation in the heart and particularly illustrating components for performed the techniques of FIGS. 2-19.

With reference to FIGS. 20 and 21, a description of an exemplary pacer/ICD will now be provided. FIG. 20 provides a simplified block diagram of the pacer/ICD, which is a dual-chamber stimulation device capable of treating both fast and slow arrhythmias with stimulation therapy, including cardioversion, defibrillation, and pacing stimulation, and also capable of assessing near-field impedance or admittance. To provide other atrial chamber pacing stimulation and sensing, pacer/ICD 10 is shown in electrical communication with a heart 612 by way of a right atrial lead 620 having an atrial tip electrode 622 and an atrial ring electrode 623 implanted in the right atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricle, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 624 is designed to receive atrial and ventricular cardiac signals and to deliver left ventricular pacing therapy using at least a left ventricular tip electrode 626 and a LV ring electrode 625, left atrial pacing therapy using at least a left atrial ring electrode 627, and shocking therapy using at least a left atrial coil electrode 628. With this configuration, biventricular pacing can be performed. Although only three leads are shown in FIG. 20, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 21. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 10, shown schematically in FIG. 21, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes at least a left ventricular tip terminal ($V_L$ TIP) 644, a left ventricular ring terminal ($V_L$ RING) 645, a left atrial ring terminal ($A_L$ RING) 646, and a left atrial shocking terminal ($A_L$ COIL) 648, which are adapted for connection to the left ventricular tip electrode 626, left ventricular ring electrode 625, the left atrial ring electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 21, an atrial pulse generator 670 and a ventricular pulse generator 672 generate pacing stimulation pulses for delivery by the right atrial lead 620, the right ventricular lead 630, and/or the CS lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, CS lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 10 utilizes the atrial and ventricular sensing circuits, 682 and 684, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the CS lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor (e.g., three-dimensional accelerometer capable of determining posture and activity) or sensors 708, sometimes referred to as a "rate-responsive" sensor because it is typically used to adjust pacing stimulation rate according to the exercise state of the patient.

However, physiological sensor(s) 708 can be equipped to sense any of a variety of cardiomechanical parameters, such as heart sounds, systemic pressure, etc. As can be appreciated, at least some these sensors may be mounted outside of the housing of the device and, in many cases, will be mounted to the leads of the device. Examples of physiological sensors that might be used with the device are described in: U.S. patent application Ser. No. 11/927,026, filed Oct. 29, 2007, of Nabutovsky et al., entitled "Systems and Methods for Exploiting Venous Blood Oxygen Saturation in combination with Hematocrit or Other Sensor Parameters for use with an Implantable Medical Device."

Moreover, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, V-V delay, etc.) at which the atrial and ventricular pulse generators, 670 and 672, generate stimulation pulses. While shown as being included within pacer/ICD 10, it is to be understood that the physiologic sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc., The pacer/ICD additionally includes a battery 710, which provides operating power to all of the circuits shown in FIG. 21. The battery 710 may vary depending on the capabilities of pacer/ICD 10. If the system only provides low voltage therapy, a lithium iodine or lithium copper fluoride cell typically may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 21, pacer/ICD 10 is shown as having an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 674 so that any desired electrode may be used. The impedance measuring circuit 712 also detects the impedance signals discussed above to use assessing near-field immittance. That is, impedance measuring circuit 712 is an electrical impedance (Z) detector operative to detect a vector-based electrical impedance (Z) signals within the patient along a plurality of sensing vectors from which near-field immittance values can be derived.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as near-field-based systems are concerned, the microcontroller includes a vector-based immittance detector 701 operative to detect impedance, admittance or related immittance signals along vectors between a set of pairs of electrodes and vector-to-individual electrode immittance convertor 703 operative to convert the vector-based immittance measurements into individual electrode-based immittance values using techniques described above. To this end, convertor 703 includes a relative near-field impedance/admittance determination system 705 operative to determine values of relative near-field impedance, admittance (or related parameters) for individual electrodes. Additionally, the microcontroller includes a set of near-field immittance-based detection systems 707, including sub-systems directed to detecting lead anomalies, pocket infections, pacing confirmation, LV/RV volumes, HF/PE events, and LAP or other conditions or parameters, using techniques discussed above.

Diagnostic data pertaining to these or other conditions can be stored in memory 694. Warning and/or notification signals are generated, when appropriate, by a warning controller 709 and then relayed to the bedside monitor 16 or to external programmer 702 (or other external system) via telemetry system 700. Alternatively, if an internal warning device 711 is provided, warnings may be generated using such a device for alerting the patient. Controller 709 is also equipped to control therapy, including controlling an implantable drug pump (if one is provided) to deliver appropriate medications. Terminals for connecting the implanted warning device and the implanted drug pump to the pacer/ICD are not separately shown.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

At least some of the techniques described herein can be performed by (or under the control of) a suitably-equipped external device. For the sake of completeness, an exemplary device programmer will now be described, which includes components for performing or controlling at least some of the functions and steps already described.

Exemplary External Programmer

Figure 22:
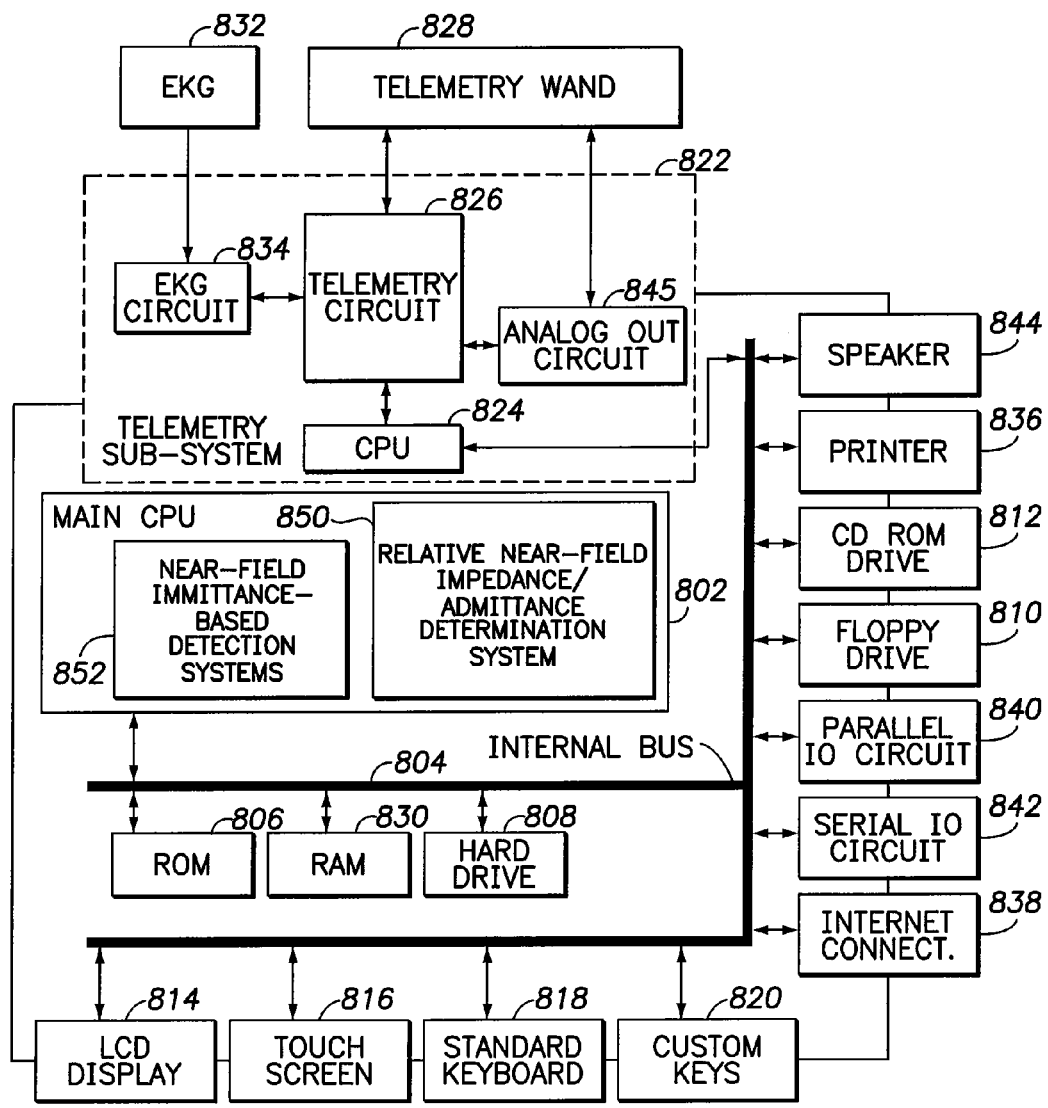
FIG. 22 is a functional block diagram illustrating components of a device programmer of FIG. 21, and in particular illustrating programmer-based components for performing or controlling the techniques of FIGS. 2-19.

FIG. 22 illustrates pertinent components of an external programmer 702 for use in programming the pacer/ICD of FIG. 21 and for performing the above-described calibration techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 702 may also be capable of processing and analyzing data received from the implanted device and from the EKG leads to, for example, render preliminary diagnosis as to medical conditions of the patient or to the operations of the implanted device.

Now, considering the components of programmer 702, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 702 to retrieve data stored within any implanted devices and to also retrieve EKG data from EKG leads, if any, coupled to the patient, along with any stored immittance data. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like, along with any recorded immittance signals. Data retrieved from the pacer/ICD also includes the data stored within the recalibration database of the pacer/ICD (assuming the pacer/ICD is equipped to store that data.) Data retrieved from the implanted devices is stored by external programmer 702 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 702, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 836.

Additionally, CPU 802 can include a relative near-field impedance/admittance determination system 850 operative to input vector-based impedance, admittance or related signals detected by the implanted device (or other devices) along vectors between a set of pairs of electrodes implanted within a patient and further operative to convert the vector-based impedance measurements into individual electrode-based relative near-field impedance values using techniques describe above. Additionally, CPU 802 can include a set of near-field immittance-based detection systems 852, including sub-systems directed to detecting lead anomalies, pocket infections, pacing confirmation, LV volume, HF/PE events, and LAP or other conditions or parameters, using techniques discussed above, which may subsequently be displayed to the physician on a LCD display 814 or sent to a central server via an internet connection 838. Alternatively, the conversion from vector-based impedance measurements to near-field electrode based impedance measurements may be performed on an external computer server after transmitting the vector-based impedance measurements from the implanted device to the external computer server.

Programmer/monitor 702 also includes a modem or other internet connection 838 to permit direct transmission of data to other programmers via the public switched telephone network (PSTN) or other interconnection line, such as a T1 line or fiber optic cable. Depending upon the implementation, the modem may be connected directly to internal bus 804 may be connected to the internal bus via either a parallel port 840 or a serial port 842. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 22 are intended merely to provide an overview of the operation of programmer and are not intended to describe in detail every feature of the hardware and software of the programmer and is not intended to provide an exhaustive list of the functions performed by the programmer.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using ASICs or the like and/or implemented remotely an external computer server.

In the following, supplemental applications of the near-field impedance model will be described. Broadly, and with brief reference once again to FIG. 2, these applications generally involve detecting or acquiring vector-based immittance measurements within tissues of the patient using a plurality of electrodes coupled to the device; converting the vector-based immittance measurements to individual electrode-based immittance values; detecting cardiac parameters and/or device operational parameters based on the individual electrode-based immittance values; and then controlling at least one device function in response to the parameters, such as detecting medical conditions, controlling therapy, titrating medications, generating warnings, recording diagnostic data, etc. As with the preceding examples, these techniques can be performed, where appropriate, by the pacer/ICD (or other implantable medical device) or by an external system based on data provided by the implanted device. In the following examples, the pacer/ICD performs the steps unless otherwise noted.

Exemplary Disequilibrium Assessment

Figure 23:
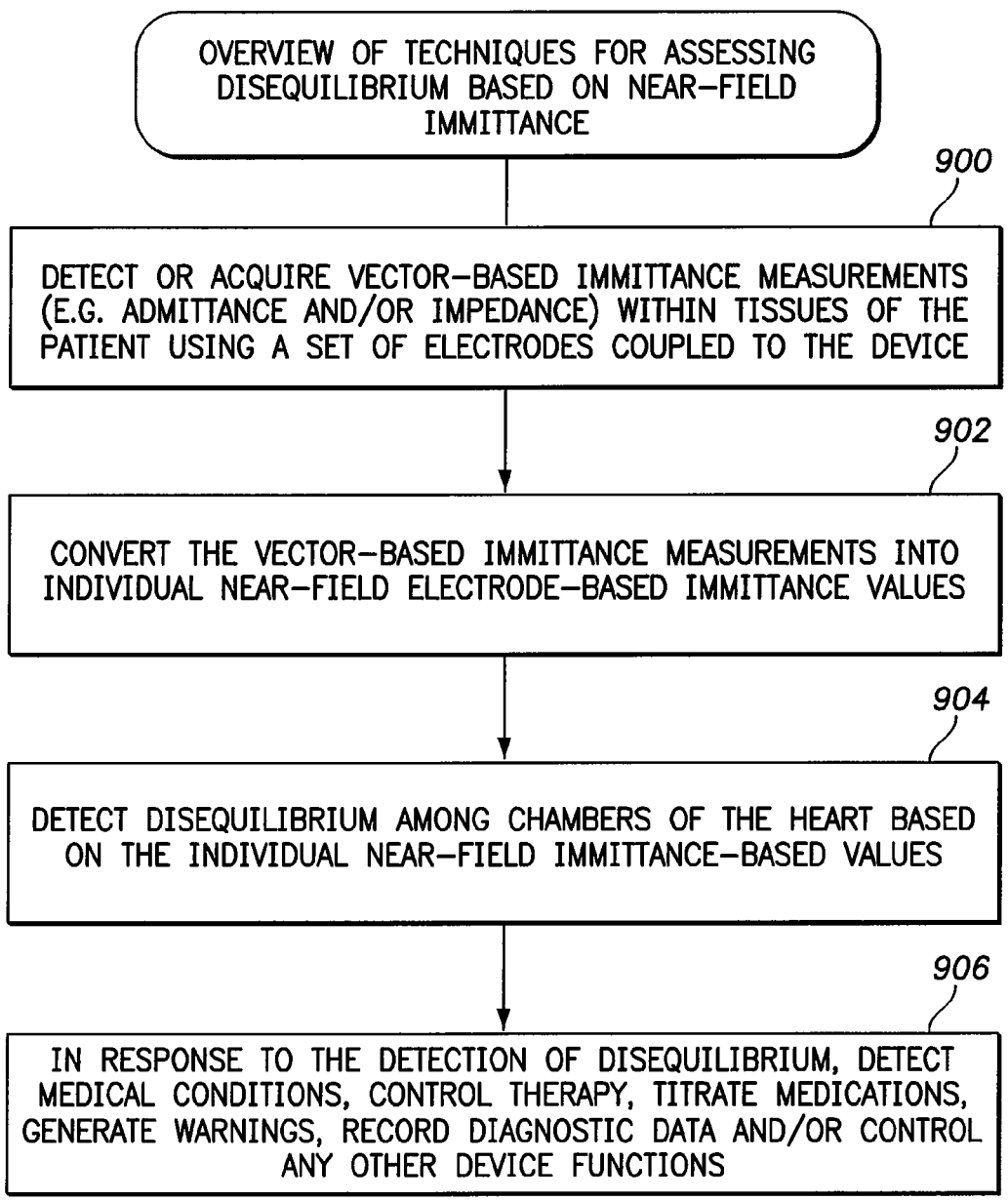
FIG. 23 summarizes an exemplary method in accordance with the general technique of FIG. 2, wherein heart chamber disequilibrium is assessed based on near-field impedance/admittance.

FIG. 23 summarizes the assessment of disequilibrium based on near-field impedance/admittance values. Disequilibrium may arise during—and be indicative of—decompensated HF. Beginning at step 900, the pacer/ICD detects or acquires vector-based immittance measurements (i.e. impedance, admittance or related values such as conductance) and, at step, 902, converts the vector-based measurements into individual near-field electrode-based immittance values using techniques discussed above. At step 904, the pacer/ICD then detects disequilibrium (i.e. lack of equilibrium, lack of concordance or lack of balance) among chambers of the heart based on the near-field immittance values. In response to any significant disequilibrium, the pacer/ICD detects medical conditions (such as acute decompensated HF), generates warnings, controls therapy, titrates medications, and/or performs any other appropriate functions.

With regard to disequilibrium, it is hypothesized that fluid volumes within the various cardiac chambers (LV, RV, and RA) and the lungs remain within equilibrium during periods of clinical stability. This equilibrium has also been observed to be present among the near-field impedance measurements derived for the various electrodes when the patient is clinically stable. During a HF decompensation episode, the equilibrium among the various cardiac chambers and lungs becomes disturbed. For example, this may occur during an acute episode of mitral valve regurgitation (MR), which might not produce an immediate acute change in LV volume but can produce an acute change in RV volume in response to increased afterload particularly in the setting of a dysfunctional RV. A scatter diagram can be utilized to evaluate the relationship between LVr, RVr, and/or RAr near-field admittance measurements and to identify episodes of disequilibrium among the various chambers. Univentricular and biventricular changes in chamber volumes are then used to identify the particular clinical condition.

Figure 24:
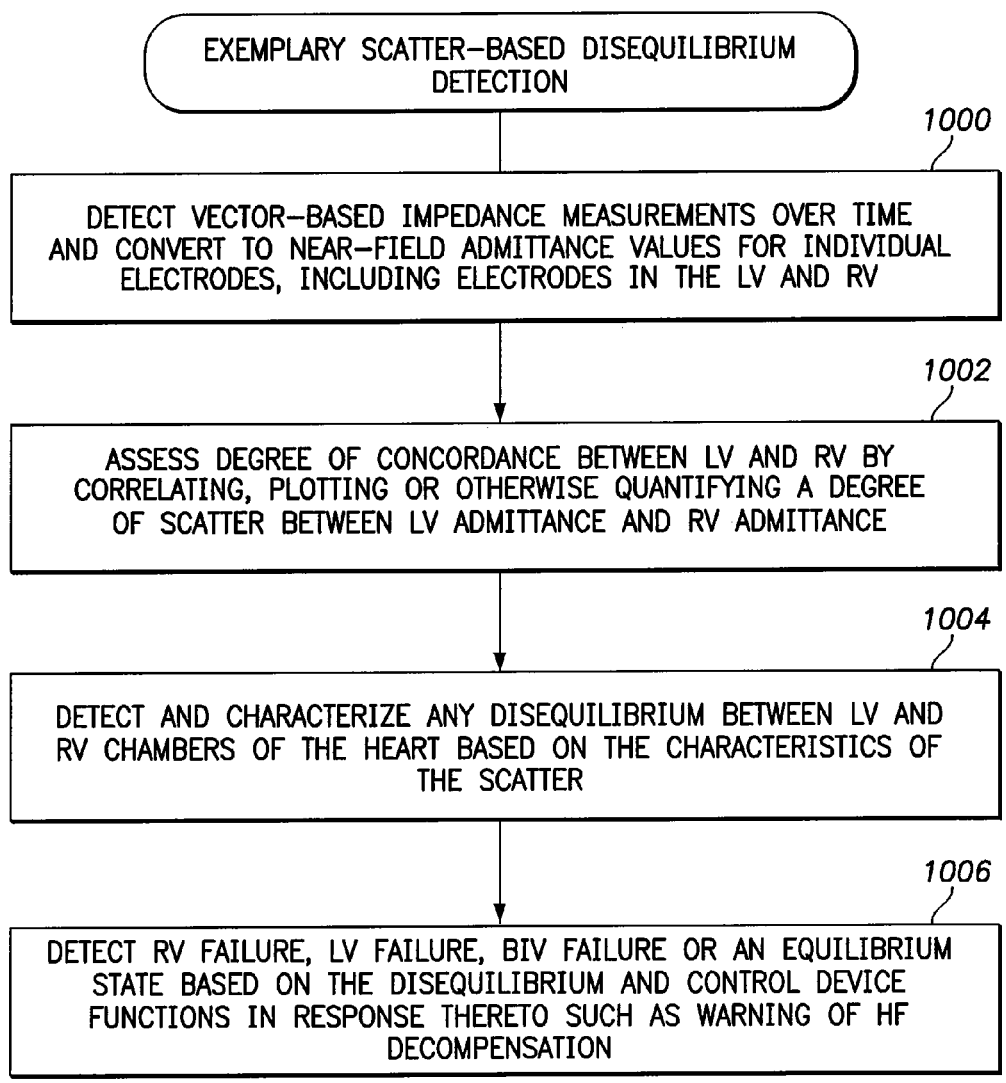
FIG. 24 illustrates an exemplary method performed in accordance with FIG. 23, wherein scatter diagram data is exploited to assess disequilibrium.

FIG. 24 illustrates an exemplary scatter-based technique for assessing disequilibrium. At step 1000, the pacer/ICD detects or acquires vector-based impedance measurements (or related electrical parameters) over some period of time and converts the vector-based measurements to near-field admittance values for the various individual electrodes, including electrodes in the LV and RV, particularly the LVring and RVring electrodes. At step 1002, the pacer/ICD then assesses the degree of concordance between the LV and RV by correlating, plotting or otherwise quantifying a degree of scatter between LV admittance and RV admittance. By "plotting," it is meant that the device records data within its internal memory in a manner analogous to that of graphical plotting so as to generate a digital representation of a scatter plot. This may be achieved, for example, by storing individual LVr and RVr near-field admittance values obtained over a period of time within different memory bins representative of different ranges of LVr and RVr near-field admittance values. Alternatively, this may be performed using common methods for cluster analysis and/or linear regression. At step 1004, the pacer/ICD then detects and characterizes any disequilibrium between the LV and RV chambers of the heart (and potentially among other chambers as well such as the LA or RA) based on the characteristics of the scatter. At step 1006, the pacer/ICD detects RV failure, LV failure, biventricular failure or a state of equilibrium based on disequilibrium, if any, and controls device functions in response thereto, such as warning of HF decompensation.

Figure 25:
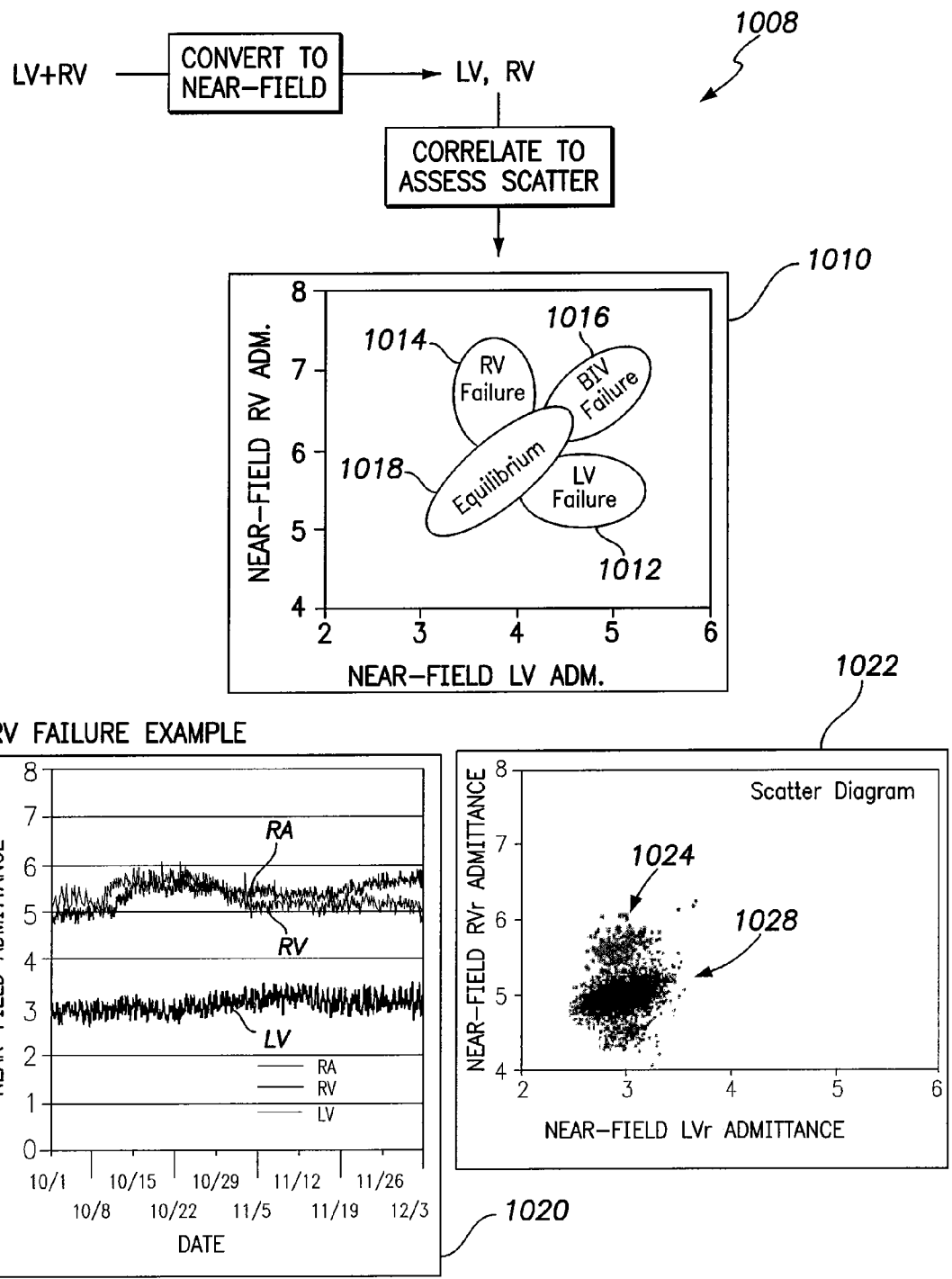
FIG. 25 includes various graphs illustrating the method of FIG. 23 for assessing disequilibrium.

Within FIG. 25, the process of correlating LV and RV admittance data to assess scatter is shown by way of schematic process 1008, which includes an LV vs. RV scatter plot 1010. The scatter plot shows different scatter zones or regimes associated with different types of heart failure, specifically an LV failure zone 1012, an RV failure zone 1014, a biventricular failure zone 1016 and an equilibrium state zone 1018. As can be seen, an increase in the near-field LVr admittance without an increase in near-field RVr admittance is associated with LV failure. This is believed to be the case because an increase in LV volume associated with isolated LV failure typically causes an increase in the near-field LVr admittance, which results in a shift of the measured data into the LV failure regime of the scatter diagram. Conversely, an increase in near-field RVr admittance without an increase in near-field LVr admittance is associated with RV failure. An increase in both indicates is associated with biventricular HF.

Graph 1020 shows admittance values obtained over a period of about two months showing changes in the near-field admittances for the RAr, RVr and LVr within a patient with isolated RV failure. In this example, the data demonstrates a sudden increase in RV volume that may be indicative of univentricular RV failure. The corresponding scatter diagram 1022 reveals a fairly large shift of the data points into in the RV failure zone 1024. Note that, in this real patient example, the time interval corresponding to points 1024 of the scatter diagram occurred when the patient was hospitalized for right-sided HF decompensation. Note also that, for comparison purposes, the diagram also shows data collected for the same patient at other times, most of which is found within the equilibrium state zone 1028.

Any suitable statistical or numerical technique can be used to assess and quantify the characteristics of the scatter to identify the particular condition (RV failure, LV failure, etc.) that is indicated or represented by the collected data. For example, an "average" of the collected data can be calculated and then compared against suitable threshold ranges to identify perturbations from a state of equilibrium and to assess the "directionality" of the scatter data (i.e. whether the perturbation is toward LV failure, RV failure or biventricular failure.)

Additional Pressure/Volume Assessment Techniques

Various techniques are described above for assessing heart chamber pressures and volumes based on near-field impedance/admittance, including techniques for estimating LAP. In the following embodiment, additional near-field-based techniques are described for assessing pressures and volumes that can be exploited as a supplement to, or an alternative to, the aforementioned techniques. These supplemental techniques include "min/max" techniques for estimating LV EDV and LV EDS based on near-field admittance, as well as exponential techniques for estimating LAP based on LV EDV.

Figure 26:
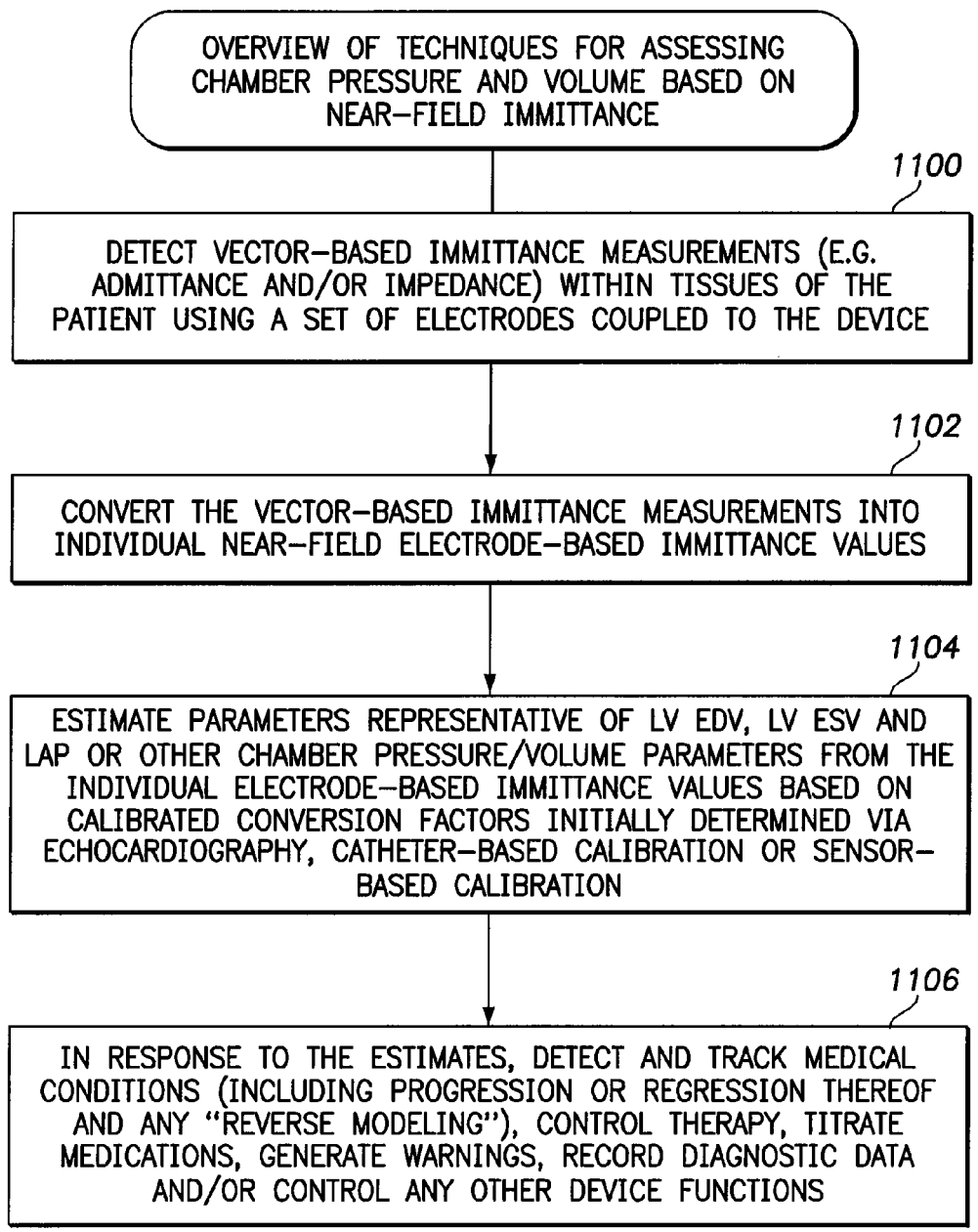
FIG. 26 summarizes an exemplary method in accordance with the general technique of FIG. 2, wherein heart chamber pressures and volumes are assessed based on near-field impedance/admittance.

FIG. 26 broadly summarizes the supplemental volume/pressure assessment techniques. Briefly, beginning at step 1100, the pacer/ICD detects or acquires vector-based immittance measurements and, at step 1102, converts the vector-based measurements into near-field electrode-based immittance values using the techniques discussed above. At step 1104, the pacer/ICD then estimates parameters representative of LV EDV, LV ESV and LAP or other chamber pressure/volume parameters from the near-field immittance values based on calibrated conversion factors initially determined via echocardiography, catheter-based calibration or sensor-based calibration or other suitable sensing modalities. Exemplary calibration techniques are described below. In response to the estimates made at step 1104, the device at step 1106 detects medical conditions, controls therapy, titrates medications, generates warnings, records diagnostic data, etc. Insofar as detecting medical conditions is concerned, the device can track near-field admittance or other measurements over time to identify worsening cardiac volume status (e.g. progression of HF) and/or to assess improvement due to therapy such as CRT (e.g. regression of HF.) Improvement in cardiac volume/pressure parameters due to therapy can be referred to as "reverse remodeling."

In one particular example, the near-field admittance signal derived for the LVr and RVr electrodes is correlated with cardiac chamber volume measurements derived from echocardiography and/or other imaging modality/sensors/catheters under a series of physiologic conditions (e.g., Valsalva maneuver, posture maneuver, handgrip isometric exercise). A similar correlation may also be applied to the near-field admittance signal of the RAr electrode to derive a correlation with RA chamber volume. A linear transformation (or other transformation such as exponential or polynomial) is then utilized to convert near-field admittance measurements into volume measurements that are representative of corresponding cardiac chamber volumes (LV, RV, and RA). In a similar fashion, the derived volume estimate can subsequently be transformed into a corresponding pressure measurement (e.g., LV EDP or LAP.) Note that when deriving the LVr near-field admittance signal at a high sampling rate (128 Hz), the beat-to-beat variations occurring during the cardiac and respiratory cycles can be determined. As previously discussed the peak near-field LVr admittance (herein Ymax) reflects LV EDV and the minimum near-field LVr admittance (herein Ymin) reflects LV ESV.

Figure 27:
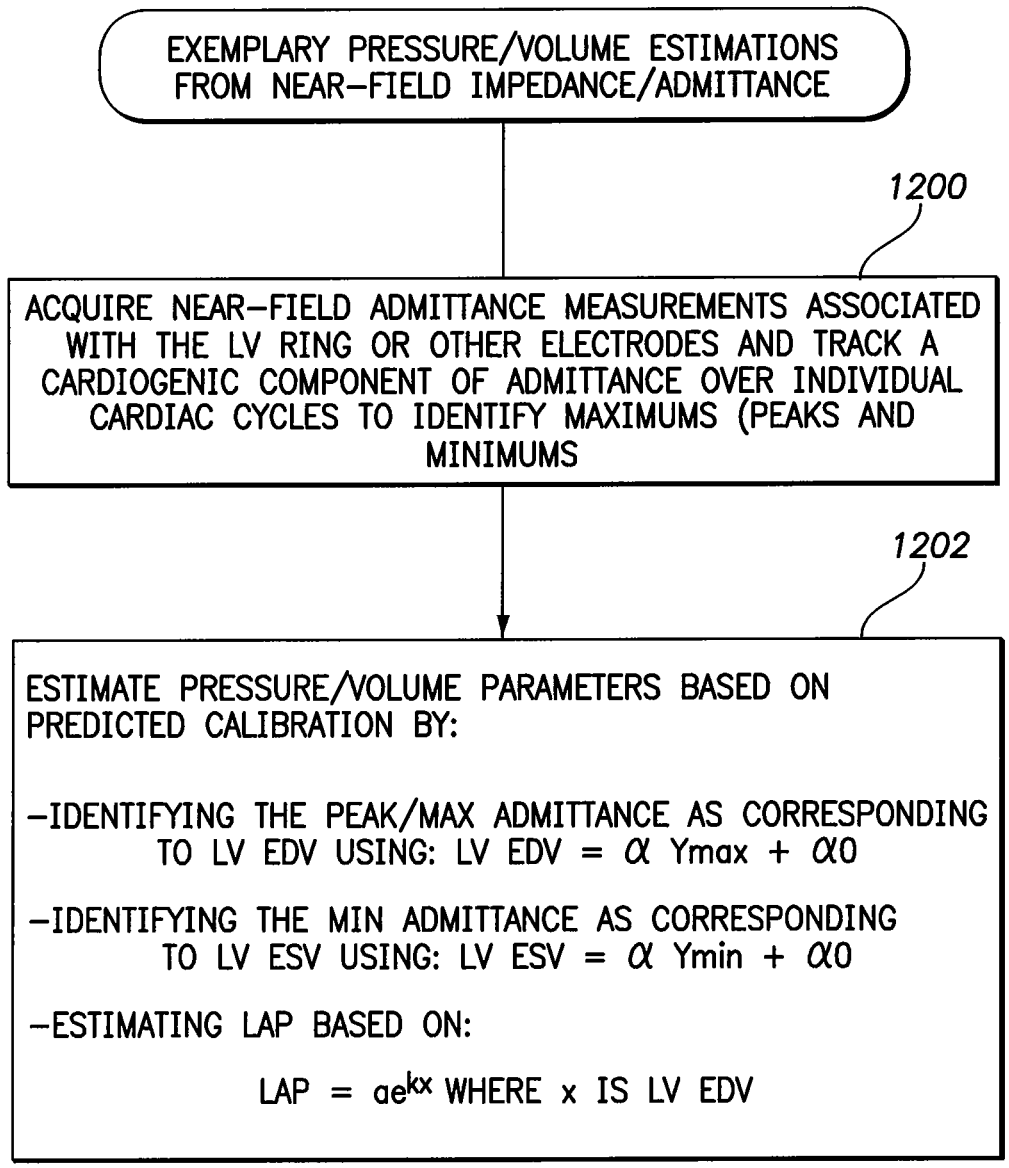
FIG. 27 illustrates an exemplary method in accordance with FIG. 26, wherein maximum and minimum admittance values are exploited to estimate LV EDV and LV ESV and an exponential formula is exploited to estimate LAP.

FIG. 27 illustrates an application of these techniques in greater detail. At step 1200, the pacer/ICD acquires near-field admittance measurements associated with individual electrodes at a high sampling rate (128 Hz) and tracks the admittance values over individual cardiac cycles to identify maximums (peaks) and minimums. That is, during each cardiac cycle, a cardiogenic component of the near-field admittance signal that varies within each heartbeat is detected and examined to identify its max (Ymax) and min (Ymin) values. Preferably, the LVring electrode is used since the near-field LVring values tend to correlate best with LV volume. At step 1202, the device then estimates various pressure/volume parameters based on predetermined calibration coefficients $\alpha$ and $\alpha 0$ that relate admittance to LV volume and predetermined calibration coefficients "a" and "k" that relate the estimated LV EDV to LAP by:

identifying the peak/max near-field admittance as corresponding to LV EDV using: LV EDV=$\alpha$Ymax+$\alpha 0$
identifying the minimum near-field admittance as corresponding to LV ESV using: LV ESV=$\alpha$Ymin+$\alpha 0$
estimating LAP from LV EDV based on: LAP=$ae^{kx}$ where "x" is LV EDV For example, the relationship between LV volume and the beat-to-beat near-field LVr admittance can be ascertained in advance to obtain the coefficients $\alpha$ and $\alpha 0$ that relate Ymax to LV EDV and Ymin to LV ESV. This may be achieved, e.g., by measuring LV EDV and LV ESV within the patient under multiple physiologic states (e.g., supine, Trendelenberg, reverse-Trendelenberg) using known techniques (such as by using "in-clinic" measurement systems, echocardiogram, under clinician supervision) while simultaneously tracking beat-to-beat near-field admittance and then applying linear correlation to determine suitable values for $\alpha$ and $\alpha 0$. More sophisticated correlation equations may instead be used to relate the near-field admittance measurements to LV volume, such as nonlinear correlations. Also, additional factors, such as whether the patient is supine may be taken into account by, for example, applying additional offsets to the measured impedance signal to compensate for posture.

Figure 28:
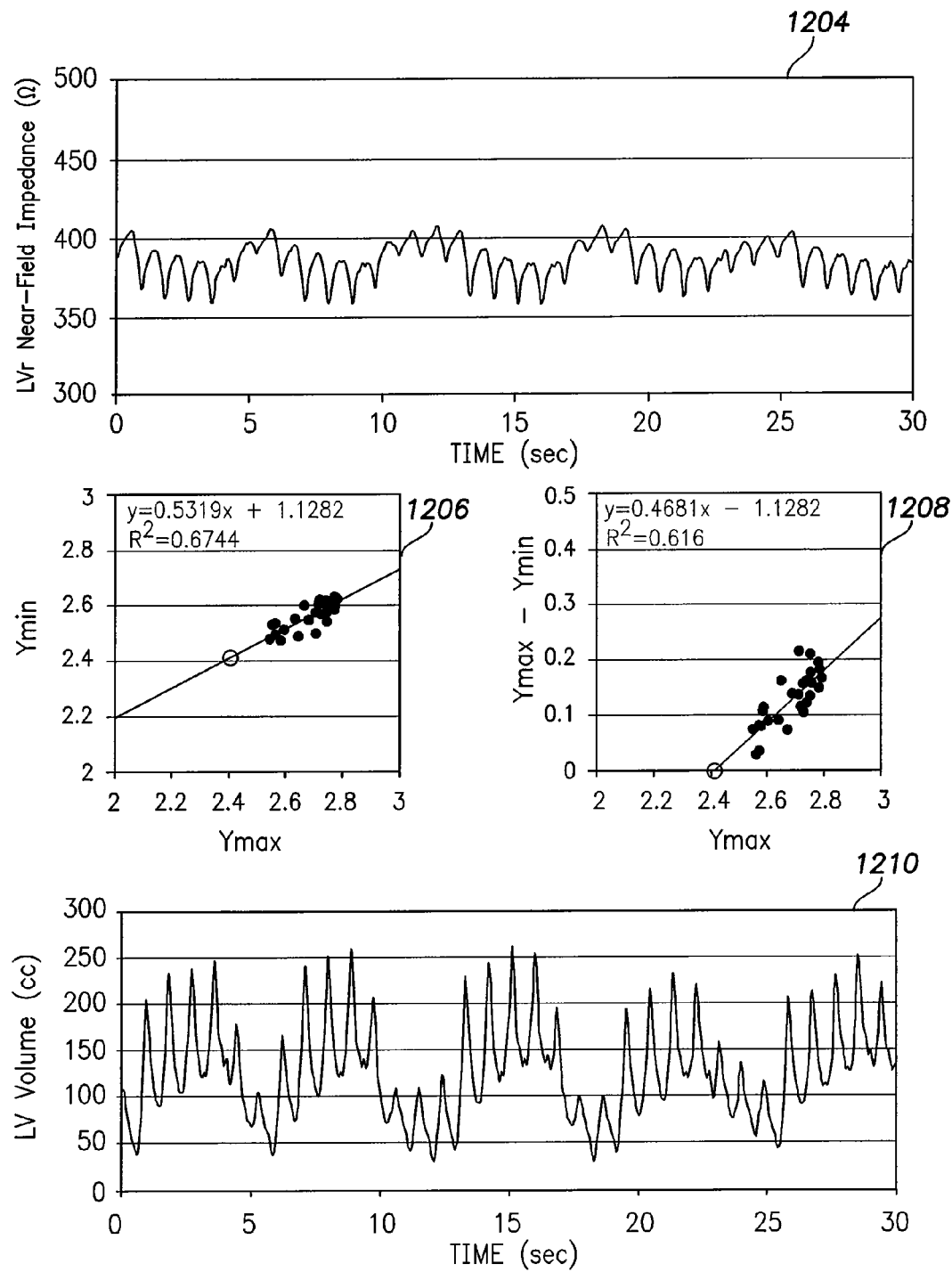
FIG. 28 includes various graphs illustrating the method of FIG. 27 for estimating LV volume.

As an illustrative example, a 30-second recording of the near-field impedance signal for the LV ring electrode acquired at a high sampling rate (128 Hz) is shown in block 1204 of FIG. 28. The recorded signal shows variation in the measured near-field impedance values throughout the cardiac and respiratory cycles as changes occur in the left ventricular volume. Using the recorded impedance signal the max impedance (Zmax) and min impedance (Zmin) are determined within each cardiac cycle and transformed into corresponding min admittance (Ymin) and max admittance (Ymax) values, respectively, using Y=1000/Z. The computed Ymin and Ymax values for each cardiac cycle are plotted against each other in block 1206. A representative average Ymax and Ymin may subsequently be derived and matched to a corresponding representative echocardiogram derived average LV EDV and LV ESV, respectively, to solve for the calibration coefficients $\alpha$ and $\alpha 0$. Alternatively, the pairs of (Ymax, Ymin) measurements may be used to determine the near-field admittance when Ymax=Ymin (or herein Yzero), which corresponds to a state when the LV is empty or when (Ymax−Ymin) equals zero as shown in block 1208. Yzero is represented in blocks 1206 and 1208 with an open circle. This is analogous to common techniques used to determine parallel conductance (Yzero) for a temporarily placed conductance catheter that is placed within the LV and used to acutely record LV volume. Using Ymax, Ymin, and/or Yzero in combination with the LV EDV, LV ESV, and zero LV volume, a set of linear equations are constructed to yield a solution for calibration coefficients $\alpha$ and $\alpha 0$. Once the calibration coefficients $\alpha$ and $\alpha 0$ are determined a continuous LV volume waveform shown in block 1210 may subsequently be generated using the near-field admittance signal using the transformation: LV volume=$\alpha$Y+$\alpha 0$ Insofar as LAP is concerned, the calibration coefficients of the aforementioned exponential conversion formula (a, k) may be calibrated based on a comparison of LV EDV versus LAP, as shown in block 325 of FIG. 16. More specifically, LAP may be estimated using either PCWP or LV EDP measurements derived from an acutely placed catheter, while LV EDV may be derived from a simultaneously acquired echocardiogram. A correlation between LV EDV and the LAP estimates may subsequently be developed to determine the calibration coefficients (a, k).

zLAP Calibration Techniques

Turning now to FIGS. 29-35, various additional or alternative techniques are described for calibrating near-field impedance-based LAP estimates (zLAP Calibration). Whereas the LAP estimation technique of the preceding section involved determining LV EDV first and then estimating LAP from LV EDV, the techniques of FIGS. 29-35 operate to estimate LAP directly from the near-field impedance/admittance values. These techniques are referred to herein as "direct" LAP estimates as the techniques do not require first determining LV volume parameters.

Figure 29:
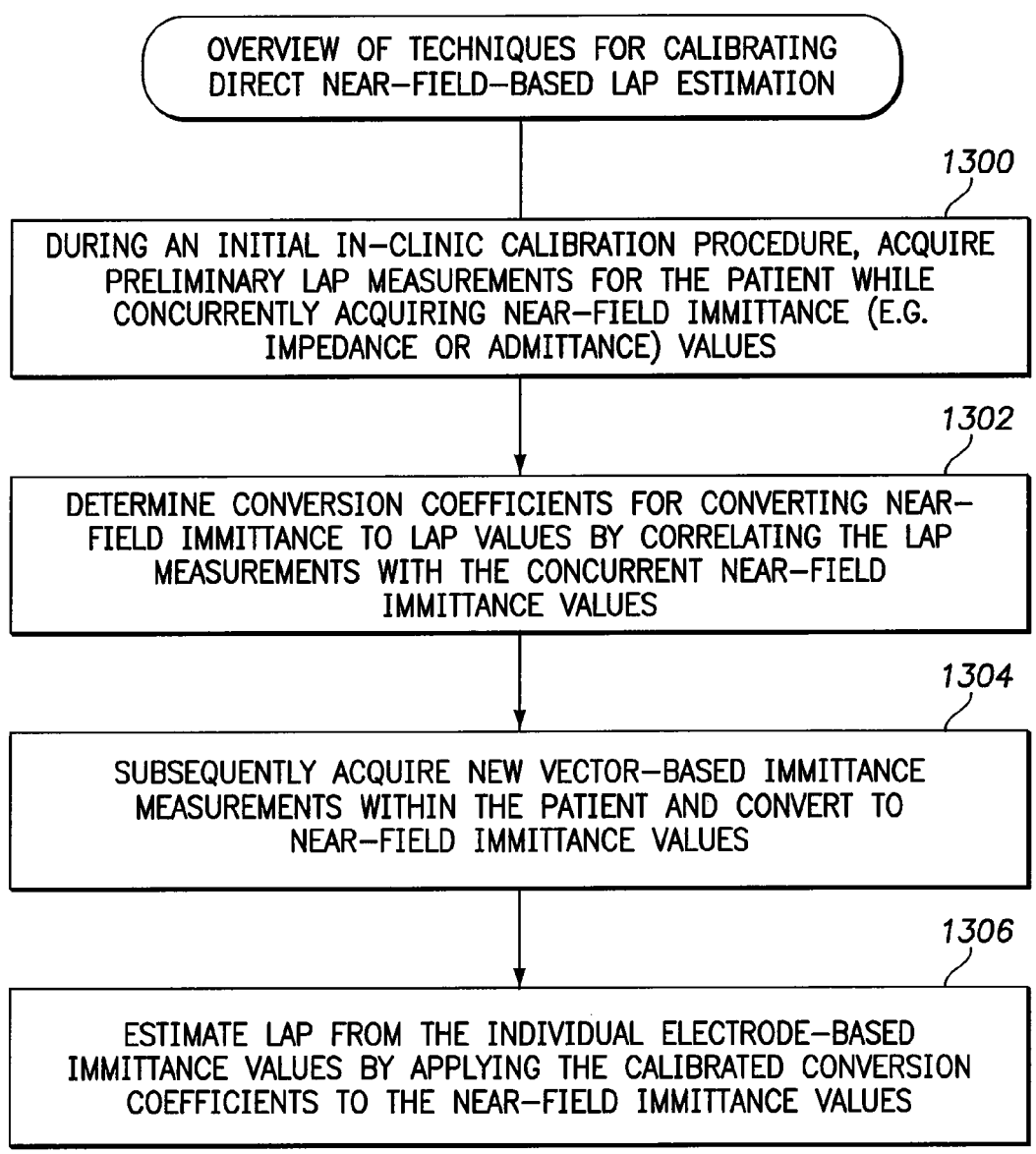
FIG. 29 summarizes an exemplary method performed in accordance with the general technique of FIG. 2 for calibrating near-field-based LAP estimates.

FIG. 29 broadly summarizes the calibration of the direct LAP estimation technique and its subsequent use. Briefly, beginning at step 1300, during an initial in-clinic calibration procedure, the calibration system acquires LAP measurements for the patient while concurrently acquiring near-field immittance (e.g. impedance or admittance) values using the techniques described above. Insofar as acquiring the LAP measurements, any suitable LAP measurement technique might be used including techniques exploiting data acquired under clinician supervision using external hemodynamic evaluation systems and/or invasive techniques using catheters placed inside the heart, such as a pulmonary artery catheter. At step 1302, the calibration system determines conversion coefficients for converting near-field immittance to LAP values by correlating the LAP measurements with concurrent near-field immittance values. Note that, in some embodiments, the calibration system is an external system, such as a device programmer, that determines calibration coefficients and then transmits the coefficients to the pacer/ICD for use therein. In other embodiments, the implanted device performs the calibration based on LAP data acquired by the device. For example, LAP data can be acquired from an external system or, if the implanted device is equipped with an alternative on-board non-impedance-based LAP detection system, the device can use data from that on-board detector to calibrate the impedance-based LAP estimation system.

Having completed the preliminary calibration procedure, the direct near-field-based LAP estimation system of the pacer/ICD is then activated to estimate LAP within the patient based on newly-acquired impedance/admittance data. That is, at step 1304, the implanted device acquires new vector-based immittance measurements within the patient and converts to near-field immittance values (e.g. impedance and/or admittance.) At step 1306, the device then estimates LAP from the near-field immittance values by applying the calibrated conversion coefficients to the near-field immittance values. Thereafter, as already explained, the device can control various device functions based on LAP, such as by detecting and responding to HF, recording diagnostics, titrating medications, etc.

Figure 30:
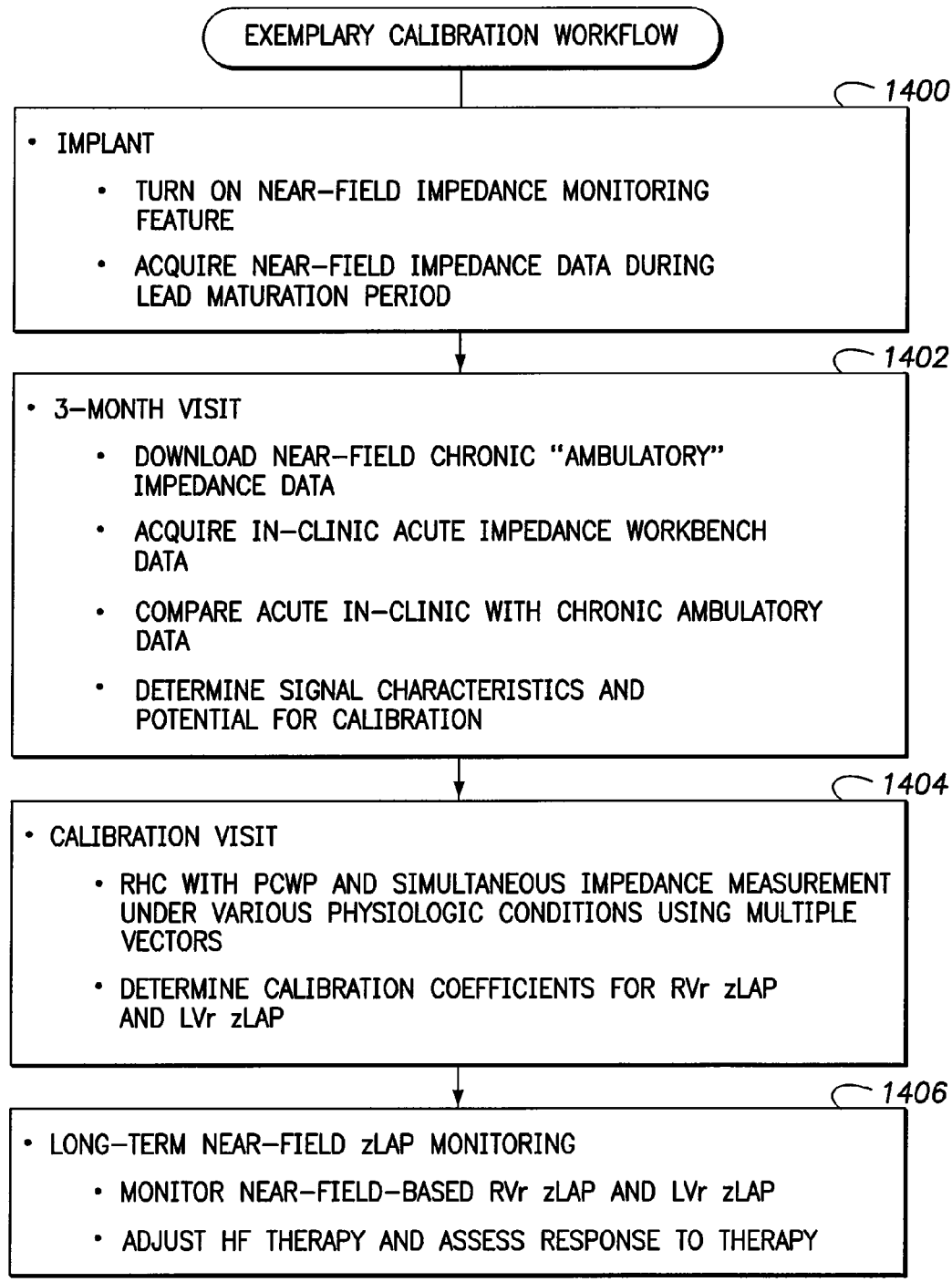
FIG. 30 illustrates an exemplary method performed in accordance with the technique of FIG. 29 for calibrating and exploiting LAP estimates based on near-field impedance/admittance.

FIG. 30 summarizes a suitable calibration workflow. Beginning at step 1400, the device is implanted within the patient and the on-board near-field impedance-monitoring feature is activated to acquire ambulatory near-field impedance data at a measurement interval of every 2 hours. At step 1402, during an in-clinic follow-up session three months after implant, the calibration system under clinician supervision downloads the ambulatory near-field impedance data acquired by the device during the first three months, acquires additional in-clinic near-field impedance data at a high sampling rate (128 Hz) under various physiologic conditions, and compares the in-clinic data with the ambulatory data to determine signal characteristics and assess the potential for reliable calibration. That is, the calibration system determines whether the data is sufficiently reliable and stable to proceed with calibration. For example, the amount of noise in the data can be assessed and the calibration aborted if there is too much noise; or the stability of the impedance signals over time can be assessed and the calibration aborted if there is too much drift in the measured near-field impedance signals that cannot be corrected; or the influence of posture on the measured near-field impedance signals may be assessed and the calibration aborted if changes in posture produce large magnitude impedance changes that are unrelated to changes in fluid volume and which cannot be corrected. Additionally, the near-field impedance data acquired during the first 3-months can be analyzed during periods of clinical stability (i.e., equilibrium) to determine the degree of concordance (herein correlation) among the near-field impedance measured for the various electrodes (e.g., between the near-field impedance for the RVr electrode and the near-field impedance for the LVr electrode), or to determine the correlation between the supine and upright near-field impedance measured for a specific electrode (e.g., RVr and LVr). As will be illustrated in subsequent embodiments such correlations (i.e., concordance) may be exploited for the purpose of deriving zLAP estimates using near-field impedance measurements obtained from alternative electrodes and/or alternative physiologic states (e.g., alternative postures).

Assuming that calibration is appropriate, calibration is performed during a subsequent calibration visit to the clinic at step 1404, where a right heart catheterization (RHC) is performed using a catheter equipped with a PCWP detector, which may be a pulmonary artery catheter. Simultaneously, near-field impedance measurements are obtained under various physiologic conditions for the electrodes selected to be utilized for estimating LAP, such as the RVring and LVring electrodes. The simultaneously acquired PCWP and near-field impedance data are then used to derive a set of calibration coefficients that may subsequently be used to convert near-field impedance measurements into zLAP estimates. Separate sets of calibration coefficients are obtained for converting RVring near-field impedance/admittance to LAP and for converting LVring near-field impedance/admittance to LAP. The LAP estimates derived from the near-field immittance measurements associated with the RVring electrode are denoted herein as RVr zLAP, and those derived from the near-field immittance measurements associated with the LVring electrode are denoted herein as LVr zLAP. If drift is present in the impedance signals, additional steps may preferably be taken to correct for drift (as discussed below.) At step 1406, long-term near-field zLAP monitoring is performed within the patient using the pacer/ICD to monitor RVr zLAP and LVr zLAP and to adjust HF therapy and assess response to therapy based on newly collected zLAP data.

Figure 31:
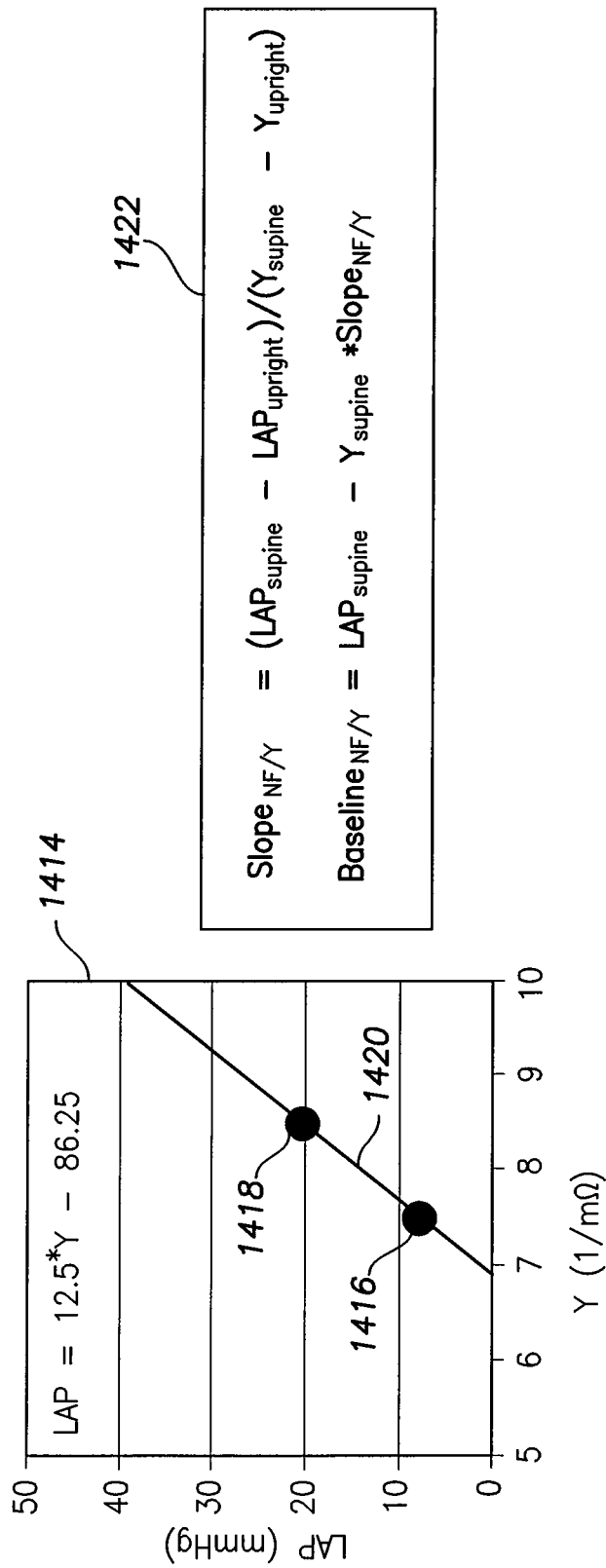
FIG. 31 includes graphs illustrating a two-point calibration technique for use with the method of FIG. 30.

FIG. 31 illustrates a two-point calibration technique by way of graph 1414, which shows two data points with differing LAP and admittance values obtained at two differing physiologic conditions. In this example, the first data point 1416 corresponds to the measurements of LAP and near-field admittance (Y) obtained in a standing upright condition, and the second data point 1418 corresponds to the measurements of LAP and Y obtained in a resting supine condition. The LAP is estimated for each of the data points with use of a PCWP measurement obtained from a pulmonary artery catheter during a RHC procedure or any other available technique. The near-field admittance measurement for each of the data points is derived in this example from a simultaneous recording of vector-based impedance measurements from which the near-field impedance for a selected electrode (e.g., RVr or LVr) is derived using the previously discussed techniques. Alternatively, the upright and supine near-field admittance measurements for the selected electrode may be determined from the ambulatory impedance data during the week(s) preceding the RHC procedure by averaging multiple near-field admittance measurements obtained in the upright standing and supine resting states. When averaging multiple ambulatory impedance measurements in the period preceding the RHC procedure it is assumed that the patient remains clinically stable such that there is little variation between the ambulatory data and similar data acquired within an in-clinic setting. This can be verified by requiring the standard deviation for the ambulatory measurements being averaged to be relatively small. As demonstrated with the equations shown in block 1422, the two data points 1416 and 1418 allow the slope and baseline of a linear relationship 1420 to be determined, which is then used to relate near-field admittance values to LAP. As noted, separate relationships can be determined for different electrodes, such as the LVring and the RVring. As can be appreciated, although only two data points are needed to determine the slope and baseline of the linear relationship 1420, more data points obtained at additional physiologic conditions (e.g., Trendelenberg position or following the administration of a high dose of intravenous diuretics or following the administration of a bolus of intravenous fluids) are preferred to provide a more robust determination.

As previously mentioned the correlation among the near-field impedance measured for the various electrodes may be exploited for the purposes of zLAP estimation using alternative electrodes. Analysis of the near-field impedance data during periods of clinical stability (i.e., equilibrium) demonstrates a strong correlation among the near-field impedance measured in the ambulatory setting for the various electrodes, particularly among the RVr, LVr, and Case electrodes. Once the zLAP calibration coefficients are determined for the near-field impedance measurements associated with one electrode (e.g., RVr), it becomes possible to leverage the correlation between the near-field impedance measurements of a pair of electrodes (e.g., RVr and LVr) to derive a zLAP estimate based on the near-field impedance associated with an alternative electrode (e.g., the LVr electrode). The benefit of this approach is that acute in-clinic near-field impedance measurements for an intra-cardiac electrode (e.g., RVr or RAr) tend to respond faster with minimal lag to acute changes in physiologic conditions in comparison to the near-field impedance measurements associated with an epicardial (e.g., LVr) or an extra-cardiac electrodes (e.g., Case), such that the calibration procedure may be easier and more reliably be conducted for an intra-cardiac electrode when relying on acute in-clinic impedance measurements.

Figure 32:
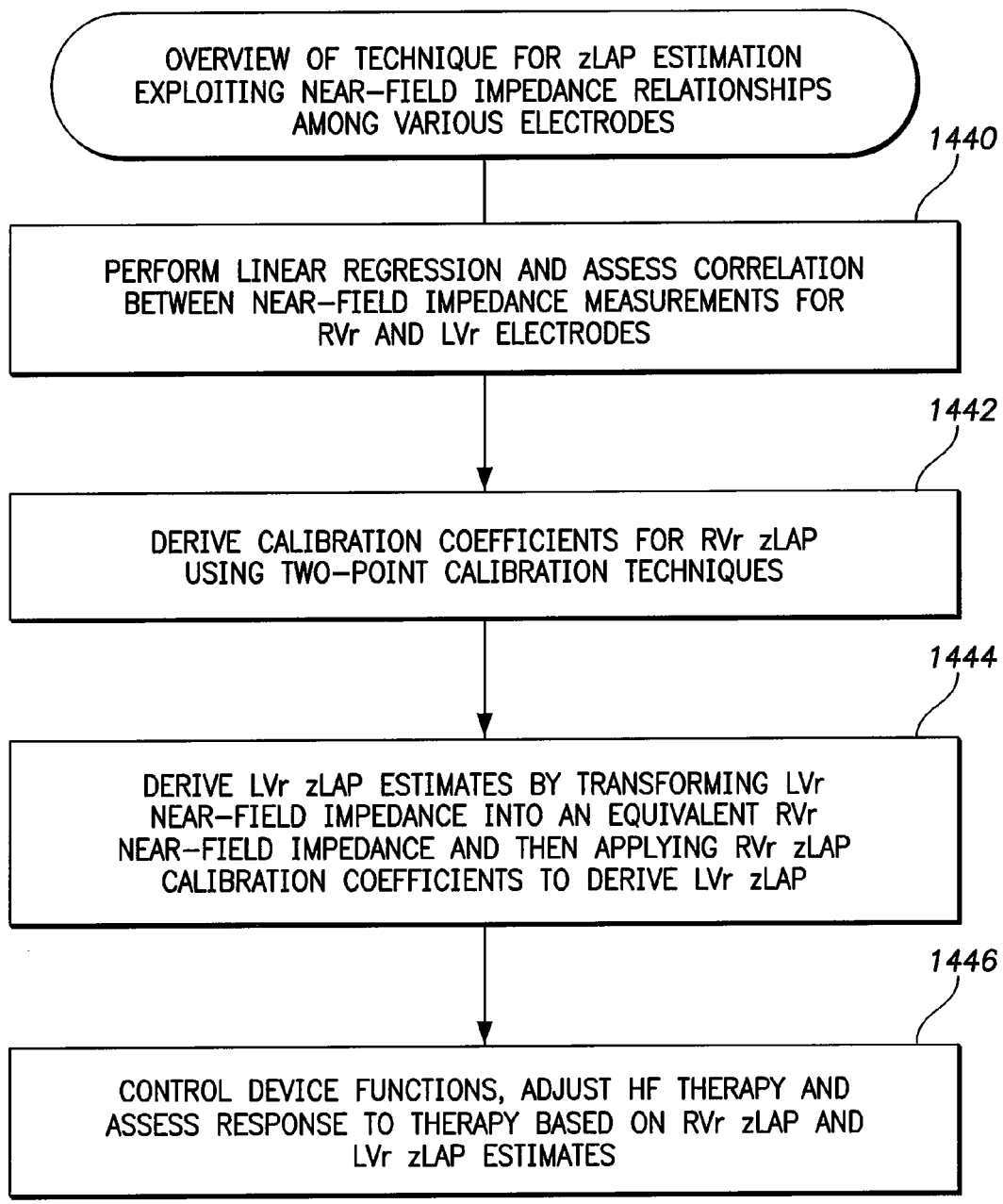
FIG. 32 summarizes an exemplary method performed for exploiting the correlation among the near-field impedance of various electrodes for calibrating near-field-based LAP estimates.

An overview of the approach for exploiting the relationship among the near-field impedance measured for the various electrodes for the purpose of zLAP estimation using an alternative electrode is provided in FIG. 32. In step 1440 the near-field impedance data measured from the various electrodes is analyzed to determine the presence or absence of correlation using linear regression. More specifically a linear regression analysis is performed using the LVr and RVr near-field impedance measurements acquired in the ambulatory setting during a period of clinical stability when equilibrium is expected to be present among the various chambers of the heart and lungs. The derived linear regression equation provides a linear transformation equation relating LVr near-field impedance measurements to equivalent RVr near-field impedance measurements. If there is inadequate correlation between the LVr and RVr near-field impedance measurements, then subsequent steps of this approach are aborted. In step 1442 the calibration coefficients for deriving RVr zLAP estimates are determined using the two-point techniques previously discussed. In step 1444 LVr zLAP estimates are derived by transforming LVr near-field impedance measurements into equivalent RVr near-field impedance measurements using the linear regression equation from step 1440 followed by application of the RVr zLAP calibration coefficients. In step 1446 RVr zLAP and LVr zLAP estimates acquired over time are utilized to control various device functions and to adjust HF therapy and assess response to therapy, as previously outlined.

From a clinical perspective, it is helpful to generate zLAP estimates in the same physiologic state (e.g., supine resting state) so that data may be easily interpreted and treatment decisions can be made more easily. The pacer/ICD acquiring the impedance signals may be equipped with activity and posture sensors that can indicate whether the impedance measurements are acquired in the supine resting state. In many patients, the minimum impedance recorded in the night-time corresponds to a resting supine physiologic state, while the maximum impedance recorded in the day-time corresponds to a standing upright physiologic state. Thus, the night-time minimum impedance data can generally be used to derive a supine zLAP estimate, while the day-time maximum impedance data can generally be used to derive an upright zLAP estimate in the absence of a posture sensor. Alternatively, the activity and posture sensor may be used to determine a representative night-time supine impedance measurement and a representative day-time standing upright impedance measurement.

Figure 33:
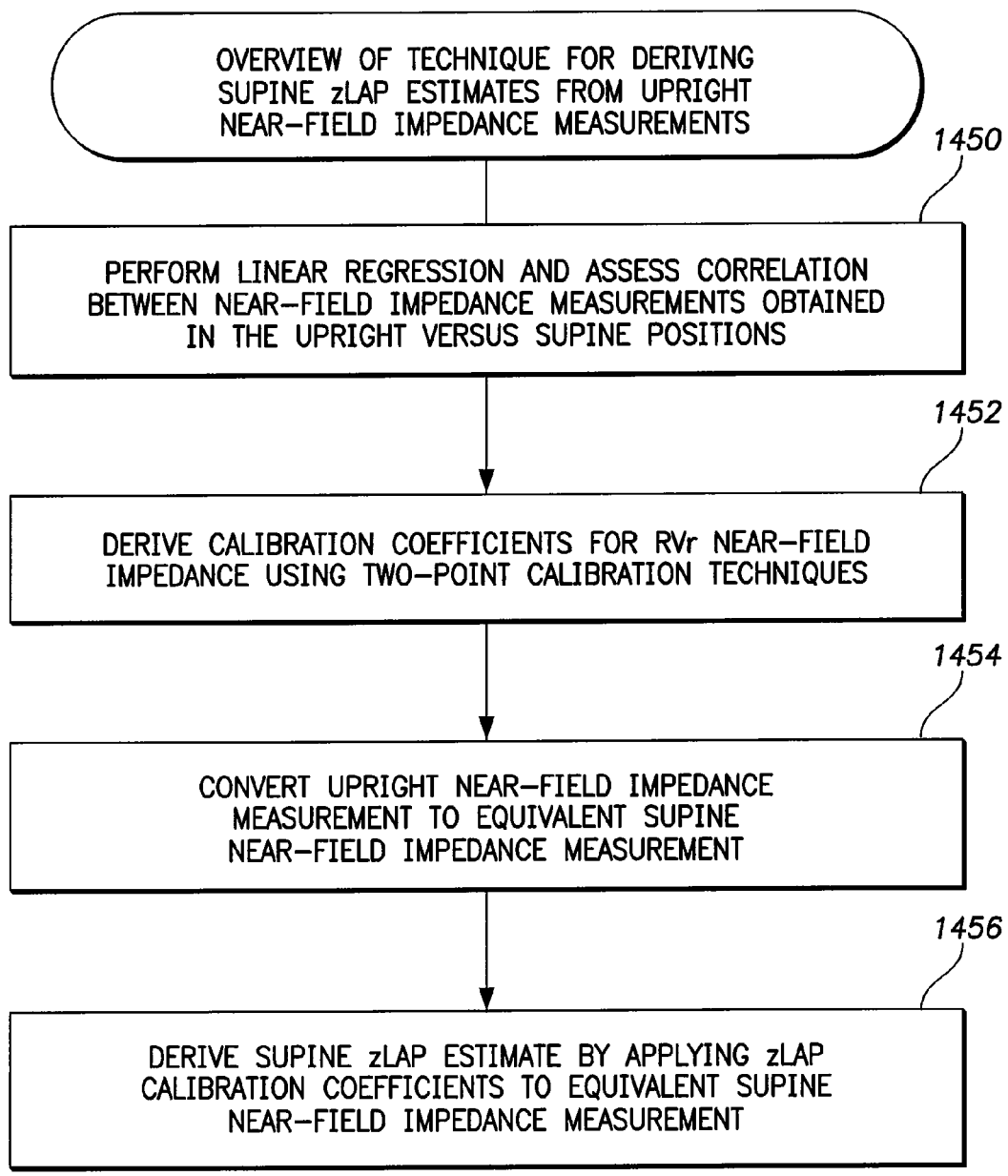
FIG. 33 summarizes an exemplary method performed for exploiting the correlation upright and supine near-field impedance measurements for calibrating near-field-based LAP estimates.

An overview of an approach for deriving supine zLAP estimates from near-field impedance measurements obtained in the upright standing state is provided in FIG. 33. In step 1450 the near-field impedance data associated with a specific electrode (e.g., LVr or RVr electrode) is analyzed to determine the presence or absence of a correlation between near-field impedance measurements obtained in the supine resting state and the upright standing state using linear regression. More specifically the impedance data acquired over each 24 hour period are analyzed to determine a representative near-field impedance measurement for the supine resting state which is then paired with a representative near-field impedance measurement for the upright standing state during the same 24 hour time window. A linear regression analysis is then performed using paired supine and upright near-field impedance measurements acquired over a period of multiple weeks when the patient is clinically stable. The derived linear regression equation provides a linear transformation equation relating upright near-field impedance measurements to equivalent supine near-field impedance measurements. If there is inadequate correlation between the upright and supine near-field impedance measurements, then subsequent steps of this approach are aborted. In step 1452 the calibration coefficients for deriving zLAP estimates are determined using the two-point techniques previously discussed. In step 1454 supine near-field impedance measurements are derived by transforming upright near-field impedance measurements into equivalent supine near-field impedance measurements using the linear regression equation from step 1450. In step 1456 a supine zLAP estimate is obtained by applying the zLAP calibration coefficients to the converted supine near-field impedance measurement.

Figure 34:
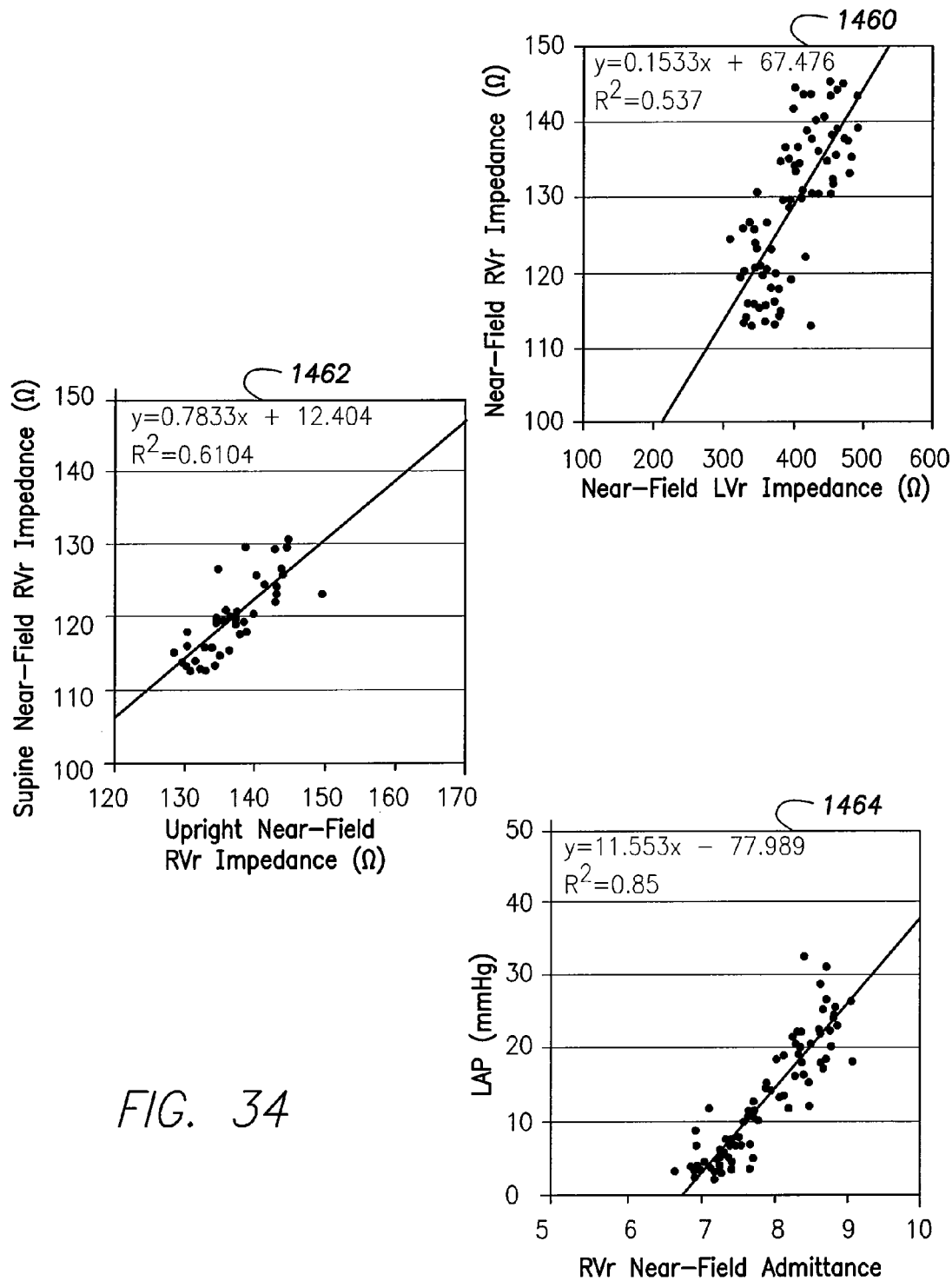
FIG. 34 illustrates the correlation between the near-field impedance for various electrodes and various postures in conjunction with the correlation with LAP.

FIG. 34 provides a graph 1460 showing an exemplary linear regression analysis performed between the RVr and LVr near-field impedance measurements collected for a patient with a history of HF during a period of clinical stability. Graph 1462 shows the linear regression analysis performed between the supine and upright RVr near-field impedance measurements for the same patient. The linear regression analysis performed in graphs 1460 and 1462 shows a good correlation coefficient ($R^2 > 0.5$). Graph 1464 shows a linear regression analysis between RVr near-field impedance and LAP using multiple paired measurements obtained at various postures (supine and upright) and over a wide range of filling pressures. The filling pressures were varied with usage of a high dose of diuretics. The linear regression equation in graph 1464 provides the calibration coefficients for deriving zLAP from the measured RVr near-field impedance. The linear regression equation in graph 1462 provides a linear transformation for converting an upright RVr near-field impedance measurement into an equivalent supine RVr near-field impedance measurement. The linear regression equation in graph 1460 provides a linear transformation for converting an LVr near-field impedance measurement into an equivalent RVr near-field impedance measurement. As previously described equivalent RVr near-field impedance measurements may be converted into zLAP estimates using the RVr zLAP calibration coefficients from graph 1464.

Figure 35:
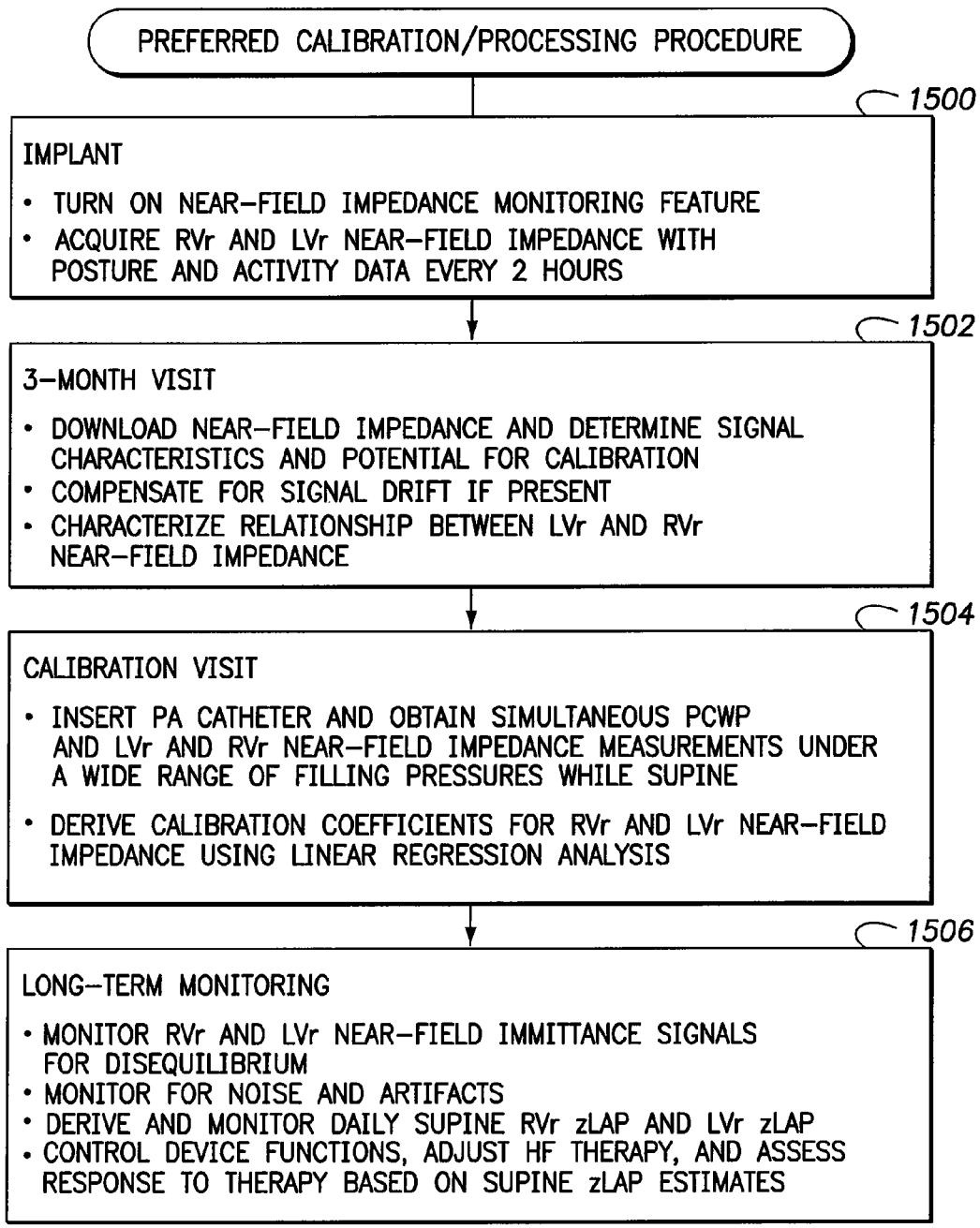
FIG. 35 illustrates a preferred calibration method performed in accordance with the technique of FIG. 29 wherein the technique additionally exploits PCWP pressure measurements obtained via right heart catheterization.

FIG. 35 illustrates the preferred or "ideal" zLAP calibration procedure. Beginning at step 1500 of FIG. 35, the near-field impedance monitoring feature is turned-ON at the time of device implant. The implanted device is equipped with a posture and activity sensor that may be in the form of a three-dimensional accelerometer, which can provide posture and activity measurements simultaneous to the near-field impedance measurements. The impedance monitoring feature is programmed to acquire every two hours the near-field impedance associated with the RVr and LVr electrodes, along with a simultaneous posture and activity measurement. Following three-months of data collection in the ambulatory setting the patient returns for a follow-up visit at step 1502. During the three-month visit the acquired near-field impedance data are retrieved from the implanted device and the potential for zLAP calibration is assessed using the techniques previously described. The near-field impedance trends for the RVr and LVr electrodes are reviewed for the presence of noise, artifacts, and/or drift. During the first several months following implant it is not uncommon to have drift in the measured near-field impedance signal that is related to the formation of scar tissue at the implant site. As will be illustrated in a subsequent example the drift rate during the first month following implant is relatively steep, but during the subsequent months becomes more gradual and ultimately dissipates within three months following implant. If the patient is clinically stable during the first three months following implant, the drift rate may be estimated from the slope of a straight-line fit to the near-field impedance signal and subsequently used to compensate for on-going drift. The relationship between the LVr and RVr near-field impedance measurements is also assessed during the three-month visit using linear regression analysis as previously described.

Once the near-field impedance signals are deemed suitable for undergoing zLAP calibration, the patient is brought back for a calibration visit. During the calibration visit shown in step 1504, a pulmonary artery catheter is inserted and used to record PCWP measurements in conjunction with LVr and RVr near-field impedance measurements under a wide range of filling pressures while keeping the patient in a supine resting state. During the calibration visit, the device is temporarily programmed to acquire the near-field impedance measurements at a higher sampling rate (e.g., every 7.5 minutes) with PCWP measurements acquired simultaneously. A wide range of filling pressures is produced by initially administering intravenous fluids over a course of several hours to achieve a maximal filling pressure (PCWP ~25 mmHg), followed by the administration of a high dose of intravenous diuretics to achieve a minimal filling pressure (PCWP ~5 mmHg). Repeat dosing of diuretics may be performed in order to achieve the target filling pressure. If at the onset of the calibration session the baseline filling pressure is already at the maximal filling pressure, then there is no need to administer intravenous fluids. The entire calibration session may extend up to a period of 12 to 24 hours in order to achieve the desired range of filling pressures and to permit a sufficient amount of time for the near-field impedance measurements of both the RVr and LVr electrodes to appropriately respond to the changes in the intra-vascular fluid volume since changes in impedance track changes in pressure with a time-lag, particularly for the LVr electrode. Alternatively, the entire calibration session may be performed over a shorter time course using the RVr electrode alone, and the correlation between the LVr and RVr near-field impedances may be exploited as described in reference to FIG. 32 when determining zLAP estimates based on LVr near-field impedance measurements. To minimize any effect of posture on electrode-tissue contact the patient is kept as much as possible in a resting supine state during the entire calibration session. The acquired calibration data is subsequently analyzed using linear regression to derive the zLAP calibration coefficients for the RVr and LVr near-field impedance data.

Following the calibration visit the long-term monitoring period shown in step 1506 is entered. The device is programmed to acquire RVr and LVr near-field immittance measurements every two hours in the ambulatory setting. The RVr and LVr near-field immittance signals are monitored for the presence of disequilibrium between the RV and LV using the techniques previously described in reference to FIG. 25. The acquired immittance signals are monitored for the presence of noise and/or artifact that may be indicative of a pacing lead disturbance and/or an anomaly, and to ensure that it is appropriate to proceed with deriving zLAP estimates based on the measured near-field immittance measurements. In the absence of noise and artifacts the near-field immittance data acquired over a 24-hour interval are analyzed to provide a representative daily supine near-field RVr and LVr immittance measurements that are then utilized in conjunction with the previously derived zLAP calibration coefficients to compute a representative daily supine RVr zLAP and LVr zLAP estimate. The derived daily supine RVr zLAP and LVr zLAP estimates are then used to control device functions, adjust HF therapy, and assess response to therapy.

Thus, various calibration techniques are provided for correlating near-field impedance/admittance with LAP. It should be noted that the concept of near-field impedance/admittance does not necessarily improve the best correlation between impedance/admittance and LAP (as compared to the correlation that might be achieved between a vector-based impedance/admittance and LAP), but the separation of impedance vectors into near-field components associated with each electrode provides improved insight to improve calibration, which is exploited by the calibration techniques described herein. Moreover, separating impedance vectors into individual electrodes makes it possible to associate each electrode's near-field impedance with a corresponding anatomical location, thereby making it easier to interpret impedance/admittance changes during clinical events: such as LV Failure (LVr) and/or RV Failure (RVr).

Techniques for Assessing the Recovery of the Electrode-Tissue Interface

With reference to FIGS. 36-40, various techniques are described for assessing the recovery from tissue injury at the electrode-tissue interface. The techniques can be used, in some examples, to track the healing response at the implant site and to detect disturbances at the electrode-tissue interface that may be indicative of various physical phenomenon occurring at the implant site, such as a lead dislodgement, perforation, and/or infection. In other cases, the information provided is useful in assessing the recovery of the electrode-tissue interface from a physiologic phenomenon (e.g., myocardial edema) back to a baseline state. These techniques are broadly summarized with reference to FIG. 36. At step 1600, the pacer/ICD detects or acquires vector-based near-field immittance measurements and, at step 1602, converts the vector-based measurements into individual near-field electrode-based immittance values using techniques already described. At step 1604, the device establishes a baseline reference near-field immittance value for each electrode-tissue interface. The device at step 1606 monitors the status of the electrode-tissue interface via the measured immittance measurements and detects and warns of physical disturbances in the electrode-tissue interface whenever there is significant perturbation of the measured near-field immittance from the baseline reference value. Once a physical disturbance is detected, the device at step 1608 tracks the recovery pattern of the measured near-field immittance relative to the established baseline reference near-field immittance value. The benefit of being able to track the recovery pattern is that it may provide a useful guide for determining how long intensive therapy and follow-up is needed. Once the near-field immittance measurements of the affected electrode-tissue interface return to baseline, routine therapy and/or routine follow-up may be reinstituted.

Figure 37:
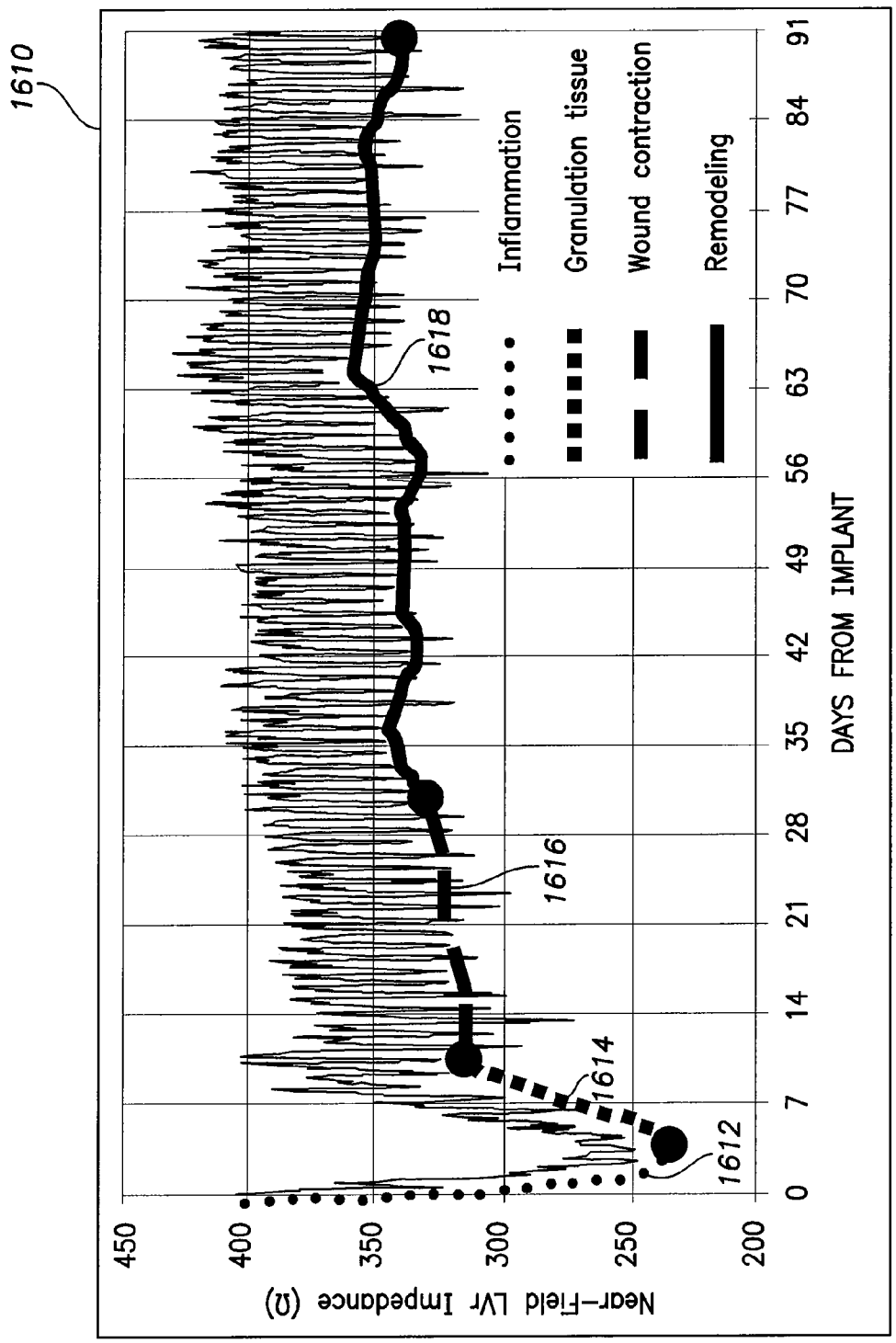
FIG. 37 includes a graph illustrating the various phases of electrode-tissue interface maturation following implant.

FIG. 37 illustrates in block 1610 the near-field impedance associated with the LVr electrode acquired over the first three months following implant from a patient implanted with a biventricular pacemaker. Following the implant procedure, an inflammatory response to tissue injury at the implant site develops which produces edema within the local tissues surrounding the electrode during the first 24 hours with the subsequent infiltration of neutrophils followed by monocytes and macrophages over the next several days (graph 1612). This acute inflammatory phase lasts ~3 days and transitions into: (1) a granulation tissue formation phase over the subsequent ~7 days (graph 1614); (2) a wound contraction phase over the subsequent ~3 weeks (graph 1616); and (3) a collagen accumulation and remodeling phase over the subsequent ~2 months (graph 1618). During this entire healing period the near-field impedance associated with the formation of scar tissue and the remodeling of the surrounding tissues containing the local interstitial fluid varies significantly and produces a characteristic maturation period in the near-field impedance trend data, which typically lasts ~3 months to completion. As the local tissue edema varies, there are significant changes in the surrounding tissue conductivity, which produce significant changes in the measured near-field impedance. An electrode that has a prolonged maturation period (>3 months) signifies the presence of increased injury at the implant site and is associated with greater formation of scar tissue, which results in higher near-field impedance measurements.

For the data shown in block 1610, the baseline reference near-field impedance acquired during the first several hours following implant is between 350 and 400Ω. The injury to local tissues at the implant site produces an acute inflammatory response with edema forming within the local tissues surrounding the electrode. The local edema causes the near-field impedance to decrease to a minimum of 250Ω within several days. Over the subsequent weeks, there is recovery back to the reference baseline near-field impedance value as the edema within the local tissue resolves and as granulation tissue is formed and the scar tissue at the implant site contracts. In the example shown there is recovery of the near-field impedance back to the baseline reference value of 350 to 400Ω within ~30 days. In this example there are no physical disturbances affecting the recovery period. However, any physical disturbance at the electrode-tissue interface could easily be detected and used to trigger a warning signal indicative of a potential clinical issue, such as a lead dislodgement, perforation, and/or infection. An example of such a disturbance was shown in reference to graph 308 in FIG. 12.

Once the maturation period is completed a stability period is entered during which the patient is clinically stable and there is equilibrium as previously described among the near-field impedance measured for the various electrodes (e.g., LVr and RVr). During the stability period, there are variations in the measured near-field impedance, which are a consequence of normal variations due to the cardiac and respiratory cycles in combination with diurnal variations in posture. Variations in the measured near-field impedance occur within each cardiac and respiratory cycle as a consequence of acute changes in the tissues contacting the electrode and the volume of fluid surrounding the electrode. Variations in the near-field impedance may occur in response to a change in posture as a result of a change in tissue contact and the surrounding fluid distribution. As previously discussed the measured near-field impedance remains relatively stable during the stability period (i.e., equilibrium) unless a disruption occurs at the electrode-tissue interface secondary to electrode migration/dislodgement, perforation, and/or an infection at the implant site, a change in electrode characteristics and/or a lead failure (e.g., lead abrasion or lead fracture), and/or a clinical decompensation that produces disequilibrium with a change in the surrounding fluid volume.

Figure 38:
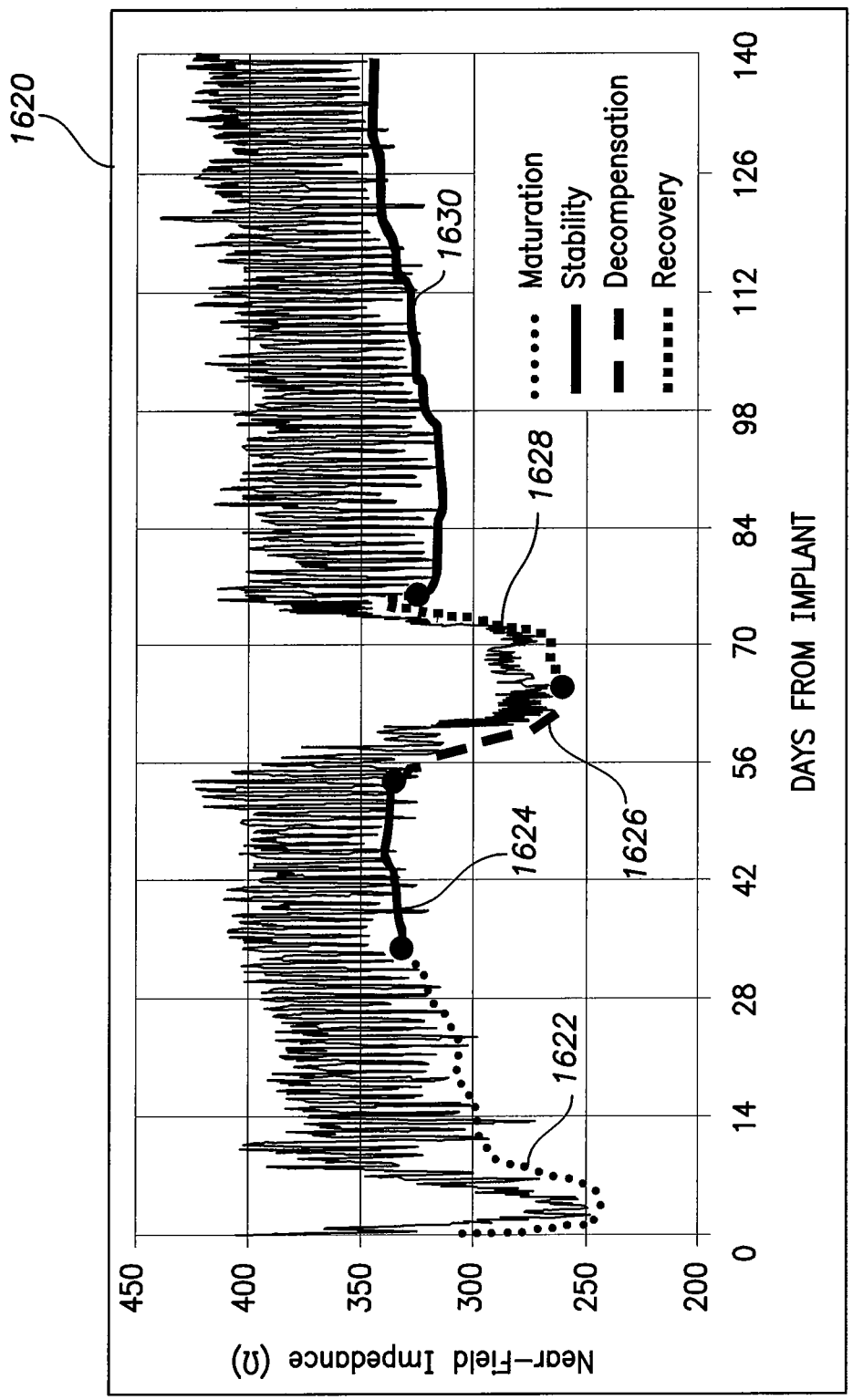
FIG. 38 includes a graph illustrating the decompensation and recovery of the near-field impedance measurements.

FIG. 38 provides an illustrative example with block 1620 of the near-field impedance associated with the LVr electrode acquired from a patient with HF. The baseline reference near-field impedance is again 350 to 400Ω. In this particular example the stability period (graph 1624) is entered ~30 days following implant after the maturation period (graph 1622) is completed. This is subsequently followed by a HF decompensation period (graph 1626) that begins at ~56 days following implant. During the HF decompensation period, fluids become retained with worsening cardiac function and hydrostatic pressure within veins tends to increase, such that the fluid volume within the tissues surrounding the electrode increases and causes an increase in the local tissue conductivity and produces a reduction in the measured near-field impedance. During the decompensation period, there is generally a loss of diurnal variations in the measured near-field impedance as a result of decreased activity and/or difficulty lying supine for a prolonged period of time. The decompensated patient is generally treated with diuretics causing excess fluids within the tissues surrounding the electrode to be removed, which causes the near-field impedance to increase back to the reference baseline near-field and produces a characteristic recovery period (graph 1628). Differences in the response and recovery patterns of the measured near-field impedance are present among the various electrodes during the decompensation and recovery periods as previously discussed in reference to FIG. 18. Once the patient is fully recovered and the near-field impedance values return to the baseline the patient re-enters the stability period (graph 1630).

Figure 36:
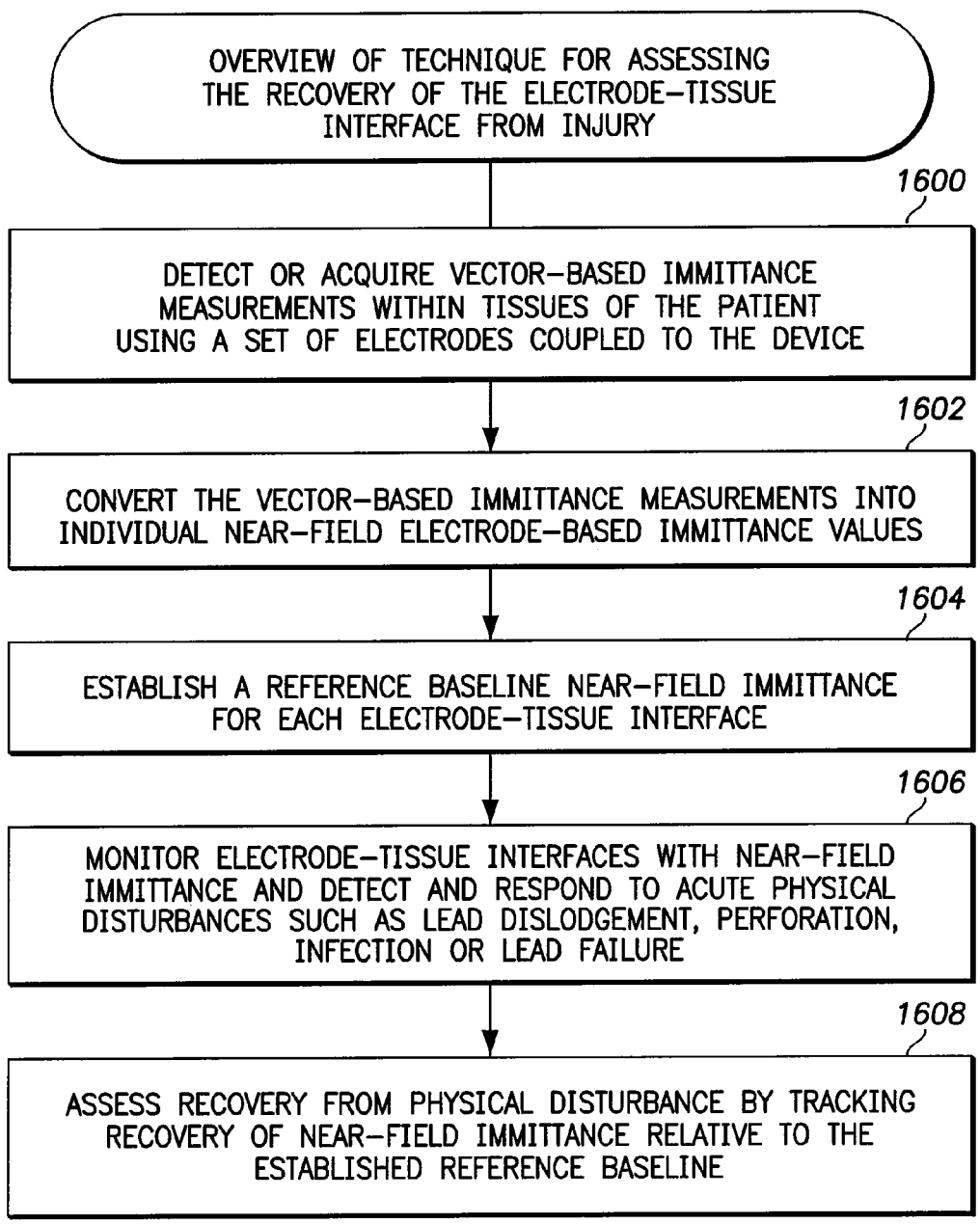
FIG. 36 illustrates an exemplary method performed in accordance with the technique of FIG. 2 for assessing the recovery of the electrode-tissue interface from injury based on near-field impedance/admittance.

FIG. 39 shows the application of the technique outlined in FIG. 36 for the purpose of guiding the intensity of therapy and duration of follow-up in a patient once hospitalized for a HF decompensation. Patients hospitalized for acute decompensated HF receive high dose diuretics. Monitoring the response to high-dose diuretic therapy with near-field impedance measurements may be useful for guiding the duration for high dose diuretics and for monitoring the stability in fluid volume once the patient is discharged in order to minimize the risk for re-hospitalization. At the time the patient is hospitalized (timeline 1642) the near-field impedance measurements associated with the LVr and RVr electrodes are to be reviewed on the programmer and utilized to establish the baseline impedance corresponding to the time when patient was previously in the stability period. In the example shown in FIG. 39 this assessment is shown in block 1640, which corresponds to the time when the patient presents to the hospital with shortness of breath at timeline 1642. The baseline near-field impedance (375Ω) is then utilized to generate a reference line 1652 for determining when there is recovery to the nominal fluid volume status. Once the in-hospital near-field impedance measurements recover back to the baseline impedance indicated by the reference line nominal dosing of diuretics may be resumed and the patient may be considered for discharge as illustrated in block 1650. When simultaneously tracking the recovery of the near-field impedance associated with the RVr and LVr electrodes there may be differences in the recovery pattern between the two electrodes. Experimental data shows that the recovery pattern for the near-field of the RVr electrode parallels the recovery of the RV volume, while the recovery pattern for the near-field impedance of the LVr electrode lags relative to the RVr electrode and parallels the recovery of the LV myocardial tissue edema. Once the patient is discharged from the hospital the clinician may choose to continue to monitor the near-field impedance measurements in the early post-discharge period to ensure that the recovery is sustained in the outpatient setting. This may be accomplished via remote monitoring. In the event the remotely monitored near-field impedance measurements show evidence of re-decompensation, the managing clinician may elect to intensify the outpatient diuretic therapy prior to the patient redeveloping symptoms that lead to re-hospitalization. Thus, monitoring the recovery pattern of the electrode-tissue interface following an episode of a HF decompensation at more than one electrode (e.g., RVr and LVr) may provide complimentary information indicative of intra-cardiac chamber volume (RV) recovery in combination with myocardial function (LV) recovery.

Exemplary Pacer/ICD with Additional Components

Figure 40:
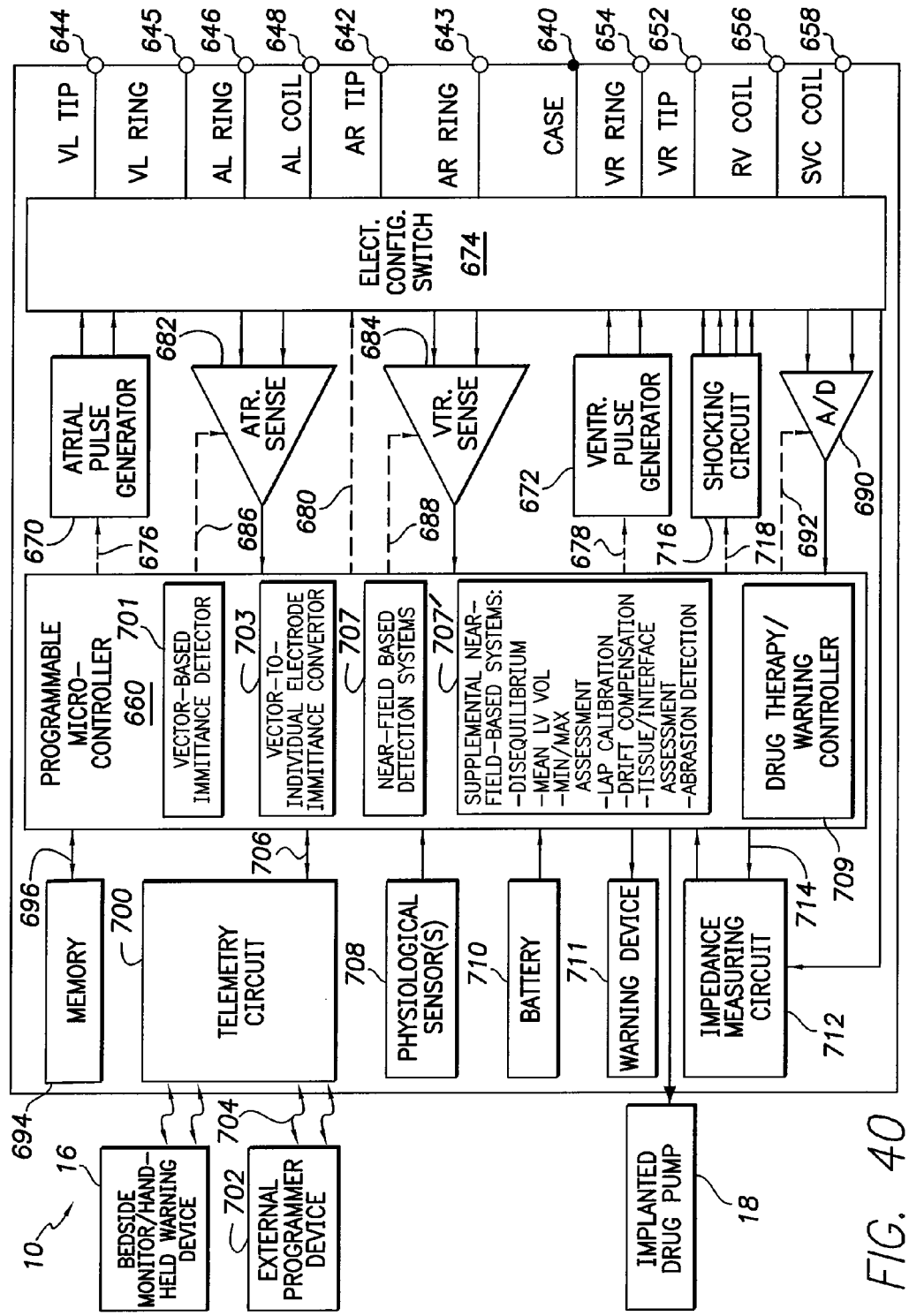
FIG. 40 is a functional block diagram of the pacer/ICD of FIG. 20, particularly illustrating additional components for performing the supplemental techniques of FIGS. 23-39.

FIG. 40 illustrates a pacer/ICD 10' similar to that of pacer/ICD 10 described above but modified to additionally include components operative to perform the functions of FIG. 23. To this end, the device additionally or alternatively includes additional near-field-based systems 707', which include components for detecting or controlling chamber disequilibrium, min/max-based LV EDV and LV EDS estimates, LAP calibration, drift compensation, electrode-tissue interface assessment, including the detection of lead abrasion.

Depending upon the implementation, these additional components of the microcontroller may be implemented as separate software modules or the modules may be combined to permit a single module to perform multiple functions. In addition, although shown as being components of the microcontroller, some or all of these components may be implemented separately from the microcontroller, using ASICs or the like.

At least some of the supplemental techniques described herein can be performed by (or under the control of) a suitably-equipped external device. For example, the near-field immittance-based detection systems 852 of device programmer of FIG. 22 can be configured to include all or some of the components of system 707' of FIG. 40, such as chamber disequilibrium detection, LAP calibration components, drift compensation components, electrode-tissue interface assessment components, etc.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. A method for use with an implantable medical device for implant within a patient, the method comprising:
    detecting vector-based immittance measurements within tissues of the patient using a plurality of electrodes coupled to the device;
    converting the vector-based immittance measurements to individual electrode-based immittance values, wherein the individual electrode-based immittance measurements are relative near-field immittance values;
    detecting one or more cardiac parameters based on the individual electrode-based immittance values, wherein detecting one or more cardiac parameters includes detecting cardiac parameters representative of disequilibrium among the chambers of the heart from the near-field immittance values; and
    controlling at least one device function in response to the parameters.

2. The method of claim 1 wherein the relative near-field immittance values are representative of the immittance of tissues in sufficiently close proximity to the electrode to exclude substantially all far-field immittance contributions.

3. The method of claim 1 wherein detecting parameters representative of disequilibrium among the chambers of the heart includes:
    acquiring relative near-field immittance values from the individual electrode-based immittance values corresponding to chambers of the heart;
    converting near-field immittance values to relative near-field admittance values;
    assessing a degree of concordance between the relative near-field admittance values; and
    identifying a poor degree of concordance as being indicative of disequilibrium between the heart chambers.

4. The method of claim 3 wherein assessing a degree of concordance between the relative near-field field admittance values is performed to assess the degree of concordance between the left ventricle (LV) and the right ventricle (RV) by quantifying characteristics of scatter between near-field LV field admittance values and near-field RV field admittance values.

5. The method of claim 4 wherein an increase in RV near-field admittance is indicative of RV failure, an increase in LV near-field field admittance is indicative of LV failure, and an increase in both LV and RV near-field field admittance is indicative of biventricular failure.

6. The method of claim 1 wherein controlling at least one device function in response to the detected parameters includes one or more of: recording information representative of disequilibrium; generating warnings representative of disequilibrium; and controlling cardioelectric stimulation based on disequilibrium.

7. The method of claim 1 wherein detecting parameters includes detecting cardiac parameters representative of one or more of chamber pressure and chamber volume from the near-field immittance values.

8. The method of claim 7 further comprising:
    estimating one or more of chamber volume and pressure, wherein estimating one or more of chamber volume and pressure includes estimating one or more of LV end diastolic volume (LV EDV), LV end systolic volume (LV ESV) and left atrial pressure (LAP) from the near-field immittance values.

9. The method of claim 8 wherein estimating LV volume includes calibrating the LV volume estimates using one or more of echocardiography, catheter-based calibration and sensor-based calibration.

10. The method of claim 8 wherein estimating LV EDV includes:
    converting the near-field immittance values corresponding to the LVring electrode into corresponding near-field admittance values;
    tracking the near-field admittance values over at least one cardiac cycle to identify a maximum near-field admittance; and
    identifying the maximum near-field admittance as corresponding to LV EDV.

11. The method of claim 10 wherein estimating LV ESV includes:
- converting the near-field immittance values corresponding to the LVring electrode into corresponding near-field admittance values;
- tracking the near-field admittance values over at least one cardiac cycle to identify a minimum near-field admittance; and
- identifying the minimum near-field admittance as corresponding to LV ESV.

12. The method of claim 11 further including estimating left atrial pressure (LAP) based on LV EDV using an exponential conversion formula.

13. The method of claim 12 wherein the exponential conversion formula is expressed as $a*e^{kx}$ where a and k are constants and wherein x represents LV EDV.

14. The method of claim 1 further comprising:
- preliminarily calibrating estimation of LAP; and
- estimating LAP from the near-field immittance values.

15. The method of claim 14 wherein calibrating the estimation of LAP from near-field immittance values includes acquiring pulmonary capillary wedge pressure (PCWP) measurements along with immittance measurements under various physiological conditions, along various vectors, and under different filling pressures, postures and levels of activity and calibrating the estimation procedure based on the measurements.

16. The method of claim 15 wherein calibrating the estimation of LAP from near-field immittance values includes determining calibration coefficients for estimating an RV LAP value from the near-field immittance measurements of at least one RV electrode and for estimating an LV LAP value from the near-field immittance measurements of at least one LV electrode.

17. The method of claim 16 further including acquiring trend data over time for RV LAP corresponding to LAP estimates without time lag.

18. The method of claim 17 further including acquiring trend data over time for LV LAP corresponding to myocardial status with a time lag.

19. The method of claim 15 wherein calibrating the estimation of LAP from near-field immittance values includes determining calibration coefficients for estimating an RV LAP value from the near-field immittance measurements of at least one RV electrode and for estimating an LV LAP value by converting LV near-field immittance values into equivalent RV near-field immittance values and applying calibration coefficients for RV LAP to derive LV LAP.

20. The method of claim 15 wherein calibrating the estimation of LAP from near-field immittance values includes determining calibration coefficients for estimating an LV LAP value from the near-field immittance measurements obtained in the supine posture of at least one LV electrode and for estimating an LV LAP value by converting LV near-field immittance values obtained in the upright standing posture into equivalent supine LV near-field immittance values and applying calibration coefficients to derive LV LAP.

21. The method of claim 1 wherein detecting parameters includes assessing an electrode-tissue interface based on near-field immittance measurements.

22. The method of claim 21 wherein assessing the electrode-tissue interface based on near-field immittance measurements includes determining a representative baseline reference near-field immittance.

23. The method of claim 22 including assessing a recovery pattern of tissue injury at the electrode-tissue interface based on a recovery of the near-field immittance relative to the representative baseline reference near-field immittance.

24. The method of claim 22 wherein assessing the electrode-tissue interface based on near-field immittance measurements includes assessing a recovery of myocardial wall edema and one or more of the cardiac chamber volumes following an episode of heart failure decompensation.

25. The method of claim 22 wherein assessing electrode-tissue interface based on near-field immittance measurements includes detecting a significant physical disturbance.

26. The method of claim 25 wherein the significant physical disturbance includes one or more of lead dislodgement, perforation, infection, and lead failure.

27. A system for use with an implantable medical device for implant within a patient, the system comprising:
- a vector-based detector operative to detect vector-based immittance measurements within tissues of the patient using a plurality of electrodes coupled to the device;
- a converter operative to convert the vector-based immittance measurements to individual electrode-based immittance values, wherein the individual electrode-based immittance measurements are relative near-field immittance values;
- a detector operative to detect one or more cardiac parameters based on the individual electrode-based immittance values, wherein the detector detects cardiac parameters representative of disequilibrium among the chambers of the heart from the near-field immittance values; and
- a controller operative to control at least one device function in response to the detection of disequilibrium.

28. A system for use with an implantable medical device for implant within a patient, the system comprising:
- means for detecting vector-based immittance measurements within tissues of the patient using a plurality of electrodes coupled to the device;
- means for converting the vector-based immittance measurements to individual electrode-based immittance values, wherein the individual electrode-based immittance measurements are relative near-field immittance values; and
- means for detecting one or more cardiac parameters based on the individual electrode-based immittance values, wherein the means for detecting detects cardiac parameters representative of disequilibrium among the chambers of the heart from the near-field immittance values.

* * * * *